United States Patent [19]
Cripe et al.

[11] Patent Number: 6,153,577
[45] Date of Patent: *Nov. 28, 2000

[54] POLYOXYALKYLENE SURFACTANTS

[75] Inventors: Thomas Anthony Cripe, Loveland; Daniel Stedman Connor, Cincinnati; Phillip Kyle Vinson, Fairfield; James Charles Theophile Roger Burckett-St. Laurent, Cincinnati; Kenneth William Willman, Fairfield, all of Ohio

[73] Assignee: The Procter & Gamble Company, Cincinnati, Ohio

[*] Notice: This patent is subject to a terminal disclaimer.

[21] Appl. No.: 09/426,594

[22] Filed: Oct. 26, 1999

Related U.S. Application Data

[63] Continuation of application No. 09/170,424, Oct. 13, 1998, which is a continuation of application No. PCT/US97/21160, Nov. 19, 1997.
[60] Provisional application No. 60/031,917, Nov. 26, 1996.
[51] Int. Cl.[7] .......................................................... C11D 1/66
[52] U.S. Cl. ........................... 510/356; 510/505; 510/506
[58] Field of Search ..................................... 510/505, 506, 510/356

[56] References Cited

U.S. PATENT DOCUMENTS

| | | | |
|---|---|---|---|
| 6,015,781 | 1/2000 | Vison et al. | 510/302 |
| 6,020,303 | 2/2000 | Cripe et al. | 510/503 |
| 6,046,152 | 4/2000 | Vinson et al. | 510/428 |

FOREIGN PATENT DOCUMENTS

| | | | |
|---|---|---|---|
| 1086178 | 9/1980 | Canada | C11D 1/02 |

*Primary Examiner*—Yogendra Gupta
*Assistant Examiner*—Christine Ingersoll
*Attorney, Agent, or Firm*—Ian S. Robinson; Kim William Zerby; Steven W. Miller

[57] ABSTRACT

Mid-chain branched primary alkyl polyoxyalkylene surfactants useful in laundry and cleaning compositions, especially granular and liquid detergent compositions. These surfactants are also suitable for formulation with other surfactants for the purpose of providing improved surfactant systems, especially for use in detergent compositions which will be used in laundry processes involving low water temperature wash conditions. The present invention also relates to novel mid-chain branched primary alkyl polyoxyalkylene surfactants suitable for use in the surfactant mixtures.

14 Claims, No Drawings

POLYOXYALKYLENE SURFACTANTS

CROSS REFERENCE

This is a continuation of application Ser. No. 09/170,424, filed Oct. 13, 1998; which is a continuation of PCT International Application Ser. No. PCT/US97/21160, filed Nov. 19, 1997; which claims priority to Provisional Application Ser. No. 60/031,917, filed Nov. 26, 1996.

FIELD OF THE INVENTION

The present invention relates to mid-chain branched primary alkyl polyoxyalkylene surfactants useful in laundry and cleaning compositions, especially granular and liquid detergent compositions. These surfactants are also suitable for formulation with other surfactants, giving improved surfactant systems, especially for use in detergent compositions which will be used in laundry processes involving low water temperature wash conditions. The present invention also relates to novel mid-chain branched primary alkyl polyoxyalkylene surfactants suitable for use in the surfactant mixtures.

BACKGROUND OF THE INVENTION

Conventional detersive surfactants comprise molecules having a water-solubilizing substituent (hydrophilic group) and an oleophilic substituent (hydrophobic group). Such surfactants typically comprise hydrophilic groups such as carboxylate, sulfate, sulfonate, amine oxide, polyoxyethylene, and the like, attached to an alkyl, alkenyl or alkaryl hydrophobe usually containing from about 10 to about 20 carbon atoms. Accordingly, the manufacturer of such surfactants must have access to a source of hydrophobe groups to which the desired hydrophile can be attached by chemical means. The earliest source of hydrophobe groups comprised the natural fats and oils, which were converted into soaps (i.e., carboxylate hydrophile) by saponification with base. Coconut oil and palm oil are still used to manufacture soap, as well as to manufacture the alkyl sulfate ("AS") class of surfactants. Other hydrophobes are available from petrochemicals, including alkylated benzene which is used to manufacture alkyl benzene sulfonate surfactants ("LAS").

The literature asserts that certain branched hydrophobes can be used to advantage in the manufacture of alkyl sulfate detersive surfactants; see, for example, U.S. Pat. No. 3,480,556 to deWitt, et al., Nov. 25, 1969. However, it has been determined that the beta-branched surfactants described in the '556 patent are inferior with respect to certain solubility parameters, as evidenced by their Krafft temperatures. It has further been determined that surfactants having branching towards the center of carbon chain of the hydrophobe have much lower Krafft temperatures. See: "The Aqueous Phase Behavior of Surfactants", R. G. Laughlin, Academic Press, N.Y. (1994) p. 347.

Generally, alkyl sulfates are well known to those skilled in the art of detersive surfactants. Alkyl sulfates were developed as a functional improvement over traditional soap surfactants and have been found to possess improved solubility and surfactant characteristics. Linear alkyl sulfates are the most commonly used of the alkyl sulfate surfactants and are the easiest to obtain. For example, long-chain linear alkyl sulfates, such as tallow alkyl sulfate, have been used in laundry detergents. However, these have significant cleaning performance limitations, especially with the trend to lower wash temperatures.

Also, as noted hereinbefore, the 2-alkyl or "beta" branched alkyl sulfates are known. In addition to U.S. Pat. No. 3,480,556 discussed above, more recently EP 439,316, published Jul. 31, 1991, and EP 684,300, published Nov. 29, 1995, describe these beta-branched alkyl sulfates. Other recent scientific papers in the area of branched alkyl sulfates include R. Varadaraj et al., J. Phys. Chem., Vol. 95, (1991), pp 1671–1676 which describes the surface tensions of a variety of "linear Guerbet" and "branched Guerbet"-class surfactants including alkyl sulfates. "Linear Guerbet" types are essentially "Y-shaped", with 2-position branching which is a long straight chain as in:

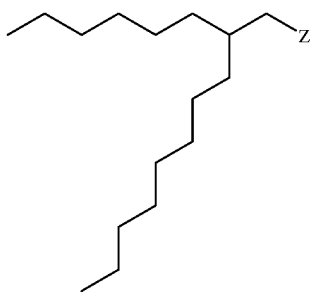

wherein Z is, for example, OSO3Na. "Branched Guerbet" types are likewise 2-position branched, but also have additional branching substitution, as in:

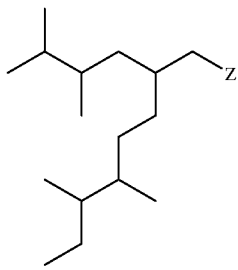

wherein Z is, for example, OSO3Na. See also Varadaraj et al., J. Colloid and Interface Sci., Vol. 140, (1990), pp 31–34 relating to foaming data for surfactants which include C12 and C13 alkyl sulfates containing 3 and 4 methyl branches, respectively (see especially p. 32).

Known alkyl sulfates also include:
1. Primary akyl sulfates derived from alcohols made by Oxo reaction on propylene or n-butylene oligomers, for example as described in U.S. Pat. No. 5,245,072 assigned to Mobil Corp.
2. Primary alkyl sulfates derived from oleic-containing lipids, for example the so-called "isostearyl" types; see EP 401,462 A, assigned to Henkel, published Dec. 12, 1990, which describes certain isostearyl alcohols and ethoxylated isostearyl alcohols and their sulfation to produce the corresponding alkyl sulfates such as sodium isostearyl sulfate.
3. Primary alkyl sulfates, for example the so-called "tridecyl" types derived from oligomerizing propylene with an acid catalyst followed by Oxo reaction;
4. Primary alkyl sulfates derived from "Neodol" or "Dobanol" process alcohols: these are Oxo products of linear internal olefins or are Oxo products of linear alpha-olefins. The olefins are derived by ethylene oligomerization to form alpha-olefins which are used directly or are isomerized to internal olefins and metathesized to give internal olefins of differering chain-lengths;

5. Primary alkyl sulfates derived from the use of "Neodol" or "Dobanol" type catalysts on internal olefins derived from feedstocks which differ from those normally used to make "Neodol" or "Dobanol" alcohols, the internal olefins being derived from dehydrogenation of paraffins from petroleum;
6. Primary alkyl sulfates derived from conventional (e.g., high-pressure, cobalt-catalyzed) Oxo reaction on internal olefins, the internal olefins being derived from dehydrogenation of paraffins from petroleum;
7. Primary alkyl sulfates derived from conventional (e.g., high-pressure, cobalt-catalyzed) Oxo reaction on alpha-olefins;
8. Primary alkyl sulfates derived from natural linear fatty alcohols such as those commercially available from Procter & Gamble Co.;
9. Primary alkyl sulfates derived from Ziegler alcohols such as those commercially available from Albemarle;
10. Primary alkyl sulfates derived from reaction of normal alcohols with a Guerbet catalyst (the function of this well-known catalyst is to dehydrogenate two moles of normal alcohol to the corresponding aldehyde, condense them in an aldol condensation, and dehydrate the product which is an alpha, beta- unsaturated aldehyde which is then hydrogenated to the 2-alkyl branched primary alcohol, all in one reaction "pot");
11. Primary alkyl sulfates derived from dimerization of isobutylene to form 2,4,4'-trimethyl-1-pentene which on Oxo reaction to the aldehyde, aldol dimerization, dehydration and reduction gives alcohols;
12. Secondary alkyl sulfates derived from sulfuric acid addition to alpha- or internal-olefins;
13. Primary alkyl sulfates derived from oxidation of paraffins by steps of (a) oxidizing the paraffin to form a fatty carboxylic acid; and (b) reducing the carboxylic acid to the corresponding primary alcohol;
14. Secondary alkyl sulfates derived from direct oxidation of paraffins to form secondary alcohols;
15. Primary or secondary alkyl sulfates derived from various plasticizer alcohols, typically by Oxo reaction on an olefin, aldol condensation, dehydration and hydrogenation (examples of suitable Oxo catalysts are the conventional Co, or more recently, Rh catalysts); and
16. Primary or Secondary alkyl sulfates other than of linear primary type, for example phytol, farnesol, isolated from natural product sources.

Beyond such known alkyl sulfates, however, is a vast array of other possible alkyl sulfate compounds and mixtures whose physical properties may or may not make them useful as laundry detergent surfactants. (I)–(XI) display just some of the possible variations (the salts are depicted only as the common sodium salts).

I

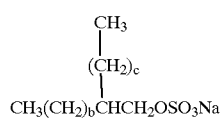

II

III

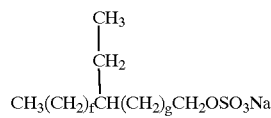

IV

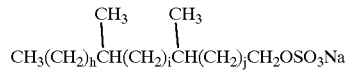

V

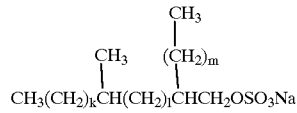

VI

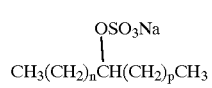

VII

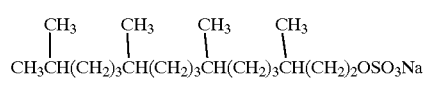

VIII

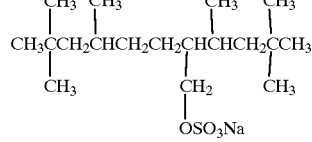

IX

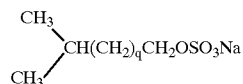

X

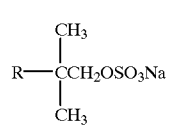

XI

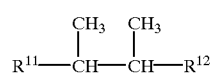

XII

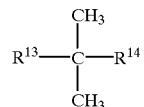

XIII

These structures are also useful to illustrate terminology in this field: thus, (I) is a "linear" alkyl sulfate. (I) is also a "primary" alkyl sulfate, in contrast with (VII) which is a "secondary" alkyl sulfate. (II) is also a "primary" alkyl sulfate—but it is "branched". The branching is exclusively in the "2-position" as in the so-called "linear Guerbet" alkyl sulfates: carbon-counting by convention starts with C1, which is the carbon atom covalently attached to the sulfate moiety. (III) can be used to represent any one of a series of branched alkyl sulfates which, when e is an integer having the value 1 or greater, have only "non-2-position branching". According to conventional wisdom, at least for linear surfactant compounds, the hydrocarbon portion needs to have at least 12 carbon atoms, preferably more, to acquire good detergency. The indices a,b,c,d,e,f,g,h,i,j,k,l,m,n,o,p,q can, in principle, be adjusted to accommodate this need. Compound (VIII) is the alkyl sulfate derived from a naturally occurring branched alcohol, phytol. Compound (IX) is a highly branched alkyl sulfate, which can, for example, be made by sulfating an alcohol derived from dimerizing isobutylene and performing an Oxo reaction on the product followed by Guerbet or Aldol condensation. Compound (X), when q=14, is an isostearyl alkyl sulfate; another so-called "isostearyl" alkyl sulfate has the general structure (III)— such compounds can be made by sulfating an alcohol derived from a monomeric by-product of the dimerization of oleic acid having 18 carbon atoms, i.e., d+e=14 in (III). Compound (XI) is a "neo" alkyl sulfate. (XII) and (XIII) are substructures depicting "vicinal" (XII) and "geminal" or "gem" (XIII) dimethyl branching, respectively. Such substructures can, in principle, occur in alkyl sulfates and other surfactants. Conventional alkyl sulfates can, moreover, be either saturated or unsaturated. Sodium oleyl sulfate, for example, is an unsaturated alkyl sulfate. Unsaturated alkyl sulfates such as oleyl sulfate can be relatively expensive and/or relatively incompatible with detergent formulations, especially those containing bleach.

In addition to the above structural variations, complex, highly branched primary alkyl sulfate mixtures having quaternary carbon atoms in the hydrophobe are producible, for example by sulfation of Oxo alcohol made via acid-catalyzed polygas reaction; moreover stereoisomerism, possible in many branched alkyl sulfates, further multiplies the number of species; and commercial alkyl sulfates can contain impurities including the corresponding alcohols, inorganic salts such as sodium sulfate, hydrocarbons, and cyclic byproducts of their synthesis.

One known material is sodium isostearyl sulfate which is a mixture of methyl and/or ethyl branches distributed along an otherwise linear alkyl backbone wherein the total number of carbons in the entire molecule are about 18. This isostearyl "mixture" is prepared in low yield from natural source feedstocks (i.e. tall oil, soy, etc.) via a process which results in branching which occurs in an uncontrolled manner, and which can vary depending upon the source of the feedstock. EP 401,462, assigned to Henkel, published Dec. 12, 1990 describes certain isostearyl alcohols and ethoxylated isostearyl alcohols and their sulfation to produce the corresponding alkyl sulfates such as "sodium isostearyl sulfate" (CAS 34481-82-8, sometimes referred to as "sodium isooctadecyl sulfate").

Again, while R. G. Laughlin in "The Aqueous Phase Behavior of Surfactants", Academic Press, N.Y. (1994) p. 347 describes the observation that as branching moves away from the 2-alkyl position towards the center of the alkyl hydrophobe there is a lowering of Krafft temperatures (for a 15% solution), such solubility observations teach nothing about the surfactancy of these compounds or their utility for incorporation into detergent compositions. In fact, both commercial practice and the published literature are equivocal on the desirability of branching in the mid-chain region. This includes the above-noted patent publications describing the beta-branched alkyl sulfates as the desired branching, as well as Finger et al., "Detergent alcohols—the effect of alcohol structure and molecular weight on surfactant properties", J. Amer. Oil Chemists' Society, Vol. 44, p. 525 (1967) or Technical Bulletin, Shell Chemical Co., SC: 364–80. These references assert, with respect to deleterious structural changes possible in alcohol sulfates that "moving a CH3 has a small effect". Data presented in a table shows a decrease in cotton detergency of 29% and a decrease in foaming of 77% relative to unbranched primary alcohol sulfate at the C13 chainlength. Moreover JP 721232 describes a detergency negative for the replacement of C11 linear primary alkyl sulfate with branched primary alkyl sulfate of unspecified branching.

In addition, K. R. Wormuth and S. Zushma, Langmuir, Vol. 7, (1991), pp 2048–2053 describes technical studies on a number of branched alkyl sulfates, especially the "branched Guerbet" type, derived from the highly branched "Exxal" alcohols made by Exxon. Phase studies establish a lipophile ranking, that is a hydrophobe ranking, as follows: highly branched≈double tail>methyl branched>linear. Assertedly, branched surfactants mix oil and water less effectively than linear surfactants. The efficiency ranking is linear>double tail>>methyl branched≈highly branched. From these results, it is not immediately evident which direction to take in the development of further improvements in branched alkyl sulfates.

Thus, going beyond simple technical theories of how to achieve cleaning superiority of one pure surfactant compound versus another, the developer and formulator of surfactants for laundry detergents must consider a wide variety of possibilities with limited (sometimes inconsistent) information, and then strive to provide overall improvements in one or more of a whole array of criteria, including performance in the presence of complex mixtures of surfactants, trends to low wash temperatures, formulation changes including builders, enzymes and bleaches, various changes in consumer habits and practices, and the need for biodegradability. In the context provided by these preliminary remarks, the development of improved surfactants for use in laundry detergents and cleaning products is clearly a complex challenge. The present invention relates to improved alkyl polyoxyalkylene surfactants.

As will be seen from the disclosures hereinafter, it has now unexpectedly been determined that certain alkyl polyoxyalkylene compositions containing mid-chain branching are preferred for use in cleaning products, especially laundry compositions used under cool or cold water washing conditions (e.g., 20° C.–5° C.). Preferred are the combination of two or more of these mid-chain branched primary alkyl polyoxyalkylene surfactants which provide a surfactant mixture that is higher in surfactancy and has better low temperature water solubility. These mixtures as produced comprise the mid-chain branching desirable for use in the surfactants of the present invention, or the surfactant mixtures disclosed herein can be formulated by mixing the desired amounts of individual mid-chain branched surfactants. Such superior mixtures are not limited to combinations with other mid-chain branched surfactants but (preferably) they can be suitably combined with one or more other traditional detergent surfactants (e.g., primary alkyl sulfates; linear alkyl benzene sulfonates; linear alkyl ethoxylated sulfates; nonionic surfactants; etc.) to provide improved surfactant systems.

These mid-chain branched surfactants are obtainable in relatively high purity making their commercialization cost effective for the formulator. Suitable product mixtures can be obtained from processes which utilize fossil-fuel sources. (The terms "derived from fossil fuels" or "fossil-fuel derived" herein are used to distinguish coal, natural gas, petroleum oil and other petrochemical derived, "synthetic" surfactants from those derived from living natural resources such as livestock or plants such as coconut palms).

One such process is designed to provide branched reaction products which are primarily (85%, or greater) alpha-olefins, and which are then converted into hydrophobes in an Oxo-reaction sequence. Such branched alpha-olefins contain from about 11 to about 18 (avg.) total carbon atoms and comprise a linear chain having an average length in the 10–18 region. The branching is predominantly monomethyl, but some di-methyl and some ethyl branching may occur. Advantageously, such process results in little (1%, or less) geminal branching, i.e., little, if any, "quaternary" carbon substitution. Moreover, little (less than about 20%) vicinal branching occurs. Of course, some (ca. 20%) of the overall feedstock used in the subsequent Oxo-process may remain unbranched. Typically, and preferably from the standpoint of cleaning performance and biodegradability, this process provides alpha-olefins with: an average number of branches (longest chain basis) in the 0.4–2.5 range; of the branched material, there are essentially no branched moieties attached to carbons 1, 2 or on the terminal (omega) carbon of the longest chain of the branched material.

Following the formation and purification of the branched-chain alpha-olefin, the feedstock is subjected to an Oxo carbonylation process. In this Oxo-step, a catalyst (e.g., conventional cobalt carbonyl) which does not move the double bond from its initial position is used. This avoids the formation of vinylidene intermediates (which ultimately yield less favorable surfactants) and allows the carbonylation to proceed at the #1 and #2 carbon atoms.

It is therefore an object of the present invention to provide mid-chain branched primary alkyl polyoxyalkylene nonionic surfactants with greater than 14.5 carbon atoms useful in cleaning compositions. It is also an object of the present invention to provide mixtures of the mid-chain branched primary alkyl polyoxyalkylene surfactants which are formulatable with other surfactants to provide cleaning compositions having one or more advantages, including greater surfactancy at low use temperatures, increased resistance to water hardness, greater efficacy in surfactant systems, improved removal of greasy or body soils from fabrics, improved compatibility with detergent enzymes, and the like.

BACKGROUND ART

U.S. Pat. No. 3,480,556 to deWitt, et al., Nov. 25, 1969, EP 439,316, published by Lever Jul. 31, 1991, and EP 684,300, published by Lever Nov. 29, 1995, describe beta-branched alkyl sulfates. EP 439,316 describes certain laundry detergents containing a specific commercial C14/C 15 branched primary alkyl sulfate, namely LIAL 145 sulfate. This is believed to have 61% branching in the 2-position; 30% of this involves branching with a hydrocarbon chain having four or more carbon atoms. U.S. Pat. No. 3,480,556 describes mixtures of from 10 to 90 parts of a straight chain primary alkyl sulfate and from 90 to 10 parts of a beta branched (2-position branched) primary alcohol sulfate of formula:

wherein the total number of carbon atoms ranges from 12 to 20 and R1 is a straight chain alkyl radical containing 9 to 17 carbon atoms and R2 is a straight chain alkyl radical containing 1 to 9 carbon atoms (67% 2-methyl and 33% 2-ethyl branching is exemplified).

As noted hereinbefore, R. G. Laughlin in "The Aqueous Phase Behavior of Surfactants", Academic Press, N.Y. (1994) p. 347 describes the observation that as branching moves away from the 2-alkyl position towards the center of the alkyl hydrophobe there is a lowering of Krafft temperatures. See also Finger et al., "Detergent alcohols—the effect of alcohol structure and molecular weight on surfactant properties", J. Amer. Oil Chemists' Society, Vol. 44, p. 525 (1967) and Technical Bulletin, Shell Chemical Co., SC: 364–80.

EP 342,917 A, Unilever, published Nov. 23, 1989 describes laundry detergents containing a surfactant system in which the major anionic surfactant is an alkyl sulfate having an assertedly "wide range" of alkyl chain lengths (the experimental appears to involve mixing coconut and tallow chain length surfactants).

U.S. Pat. No. 4,102,823 and GB 1,399,966 describe other laundry compositions containing conventional alkyl sulfates.

G.B. Patent 1,299,966, Matheson et al., published Jul. 2, 1975, discloses a detergent composition in which the surfactant system is comprised of a mixture of sodium tallow alkyl sulfate and nonionic surfactants.

Methyl- substituted sulfates include the known "isostearyl" sulfates; these are typically mixtures of isomeric sulfates having a total of 18 carbon atoms. For example, EP 401,462 A, assigned to Henkel, published Dec. 12, 1990, describes certain isostearyl alcohols and ethoxylated isostearyl alcohols and their sulfation to produce the corresponding alkyl sulfates such as sodium isostearyl sulfate. See also K. R. Wormuth and S. Zushma, Langmuir, Vol. 7, (1991), pp 2048–2053 (technical studies on a number of branched alkyl sulfates, especially the "branched Guerbet" type); R. Varadaraj et al., J. Phys. Chem., Vol. 95, (1991), pp 1671–1676 (which describes the surface tensions of a variety of "linear Guerbet" and "branched Guerbet"-class surfactants including alkyl sulfates); Varadaraj et al., J. Colloid and Interface Sci., Vol. 140, (1990), pp 31–34 (relating to foaming data for surfactants which include C12 and C13 alkyl sulfates containing 3 and 4 methyl branches, respectively); and Varadaraj et al., Langmuir, Vol. 6 (1990), pp 1376–1378 (which describes the micropolarity of aqueous micellar solutions of surfactants including branched alkyl sulfates).

"Linear Guerbet" alcohols are available from Henkel, e.g., EUTANOL G-16.

Primary akyl sulfates derived from alcohols made by Oxo reaction on propylene or n-butylene oligomers are described in U.S. Pat. No. 5,245,072 assigned to Mobil Corp. See also: U.S. Pat. No. 5,284,989, assigned to Mobil Oil Corp. (a method for producing substantially linear hydrocarbons by oligomerizing a lower olefin at elevated temperatures with constrained intermediate pore siliceous acidic zeolite), and U.S. Pat. Nos. 5,026,933 and 4,870,038, both to Mobil Oil Corp. (a process for producing substantially linear hydrocarbons by oligomerizing a lower olefin at elevated temperatures with siliceous acidic ZSM-23 zeolite).

See also: Surfactant Science Series, Marcel Dekker, N.Y. (various volumes include those entitled "Anionic Surfactants" and "Surfactant Biodegradation", the latter by R. D. Swisher, Second Edition, publ. 1987 as Vol. 18; see especially p. 20–24 "Hydrophobic groups and their sources"; pp 28–29 "Alcohols" , pp 34–35 "Primary Alkyl Sulfates" and pp 35–36 "Secondary Alkyl Sulfates"); and literature on "higher" or "detergent" alcohols from which alkyl sulfates are typically made, including: CEH Marketing Research Report "Detergent Alcohols" by R. F. Modler et al., Chemical Economics Handbook, 1993, 609.5000–609.5002; Kirk Othmer's Encyclopedia of Chemical Technology, 4th Edition, Wiley, N.Y., 1991, "Alcohols, Higher Aliphatic" in Vol. 1, pp 865–913 and references therein.

SUMMARY OF THE INVENTION

The present invention relates to surfactant compositions comprising from about 0.001% to about 100% of one or more (preferably a mixture of two or more) mid-chain branched primary alkyl polyoxyalkylenes having the formula:

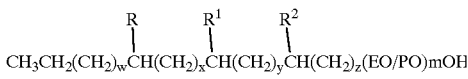

wherein the total number of carbon atoms in the branched primary alkyl moiety of this formula (including the R, $R^1$, and $R^2$ branching, but not including the carbon atoms in the EO/PO alkoxy moiety) is from 14 to 20, and wherein further for this surfactant mixture the average total number of carbon atoms in the branched primary alkyl moieties having the above formula is within the range of greater than 14.5 to about 17.5 (preferably from about 15 to about 17); R, $R^1$, and $R^2$ are each independently selected from hydrogen and $C_1$–$C_3$ alkyl (preferably methyl), provided R, $R^1$, and $R^2$ are not all hydrogen and, when z is 1, at least R or $R^1$ is not hydrogen; w is an integer from 0 to 13; x is an integer from 0 to 13; y is an integer from 0 to 13; z is an integer of at least 1; w+x+y+z is from 8 to 14; and EO/PO are alkoxy moieties including for example ethoxy (from about 0 to about 30), propoxy (from about 0 to about 30), butoxy (from about 0 to about 30), etc, preferably selected from ethoxy, propoxy, and mixed ethoxy/propoxy groups, most preferably ethoxy, wherein m is at least about 1, preferably within the range of from about 3 to about 30, more preferably from about 5 to about 20, and most preferably from about 5 to about 15. It is to be recognized that the (EO/PO)m moiety may be either a distribution with average degree of alkoxylation corresponding to m, or it may be a single specific chain with alkoxylation (e.g., ethoxylation and/or propoxylation) of exactly the number of units corresponding to m.

The present invention preferably further encompasses a detergent composition, for example one useful for laundering fabrics, washing dishes and cleaning hard surfaces, comprising:

(a) from about 0.001% to about 99% of one or more mid-chain branched primary alkyl polyoxyalkylene surfactants having the formula herein; and (b) from about 1% to about 99.999% by weight of one or more detergent adjunct ingredients.

Preferably, said detergent compositions comprise a mixture of mid-chain branched primary alkyl polyoxyalkylene surfactants, said mixture comprising at least about 2% by weight of two or more mid-chain branched primary alkyl polyoxyalkylenes having the formula:

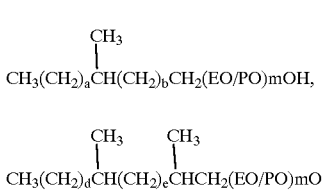

or mixtures thereof; wherein a, b, d, and e are integers, a+b is from 10 to 16, d+e is from 8 to 14 and wherein further when a+b=10, a is an integer from 2 to 9 and b is an integer from 1 to 8;

when a+b=11, a is an integer from 2 to 10 and b is an integer from 1 to 9;

when a+b=12, a is an integer from 2 to 11 and b is an integer from 1 to 10;

when a+b=13, a is an integer from 2 to 12 and b is an integer from 1 to 11;

when a+b=14, a is an integer from 2 to 13 and b is an integer from 1 to 12;

when a+b=15, a is an integer from 2 to 14 and b is an integer from 1 to 13;

when a+b=16, a is an integer from 2 to 15 and b is an integer from 1 to 14;

when d+e=8, d is an integer from 2 to 7 and e is an integer from 1 to 6;

when d+e=9, d is an integer from 2 to 8 and e is an integer from 1 to 7;

when d+e=10, d is an integer from 2 to 9 and e is an integer from 1 to 8;

when d+e=11, d is an integer from 2 to 10 and e is an integer from 1 to 9;

when d+e=12, d is an integer from 2 to 11 and e is an integer from 1 to 10;

when d+e=13, d is an integer from 2 to 12 and e is an integer from 1 to 11;

when d+e=14, d is an integer from 2 to 13 and e is an integer from 1 to 12;

wherein for this surfactant mixture the average total number of carbon atoms in the branched primary alkyl moieties having the above formulas is within the range of greater than 14.5 to about 17.5; and wherein EO/PO are alkoxy moieties, preferably selected from ethoxy, propoxy, and mixed ethoxy/propoxy groups, wherein m is at least about 1, preferably within the range of from about 3 to about 30, more preferably from about 5 to about 20, and most preferably from about 5 to about 15.

It is also an object of the present invention to provide novel mid-chain branched primary alkoxylated surfactants for use in the surfactant mixtures described herein. The invention therefore also preferably relates to novel polyoxyalkylene compounds of formula:

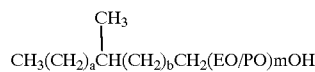

wherein: a is an integer from 2 to 11, b is an integer from 1 to 10, and a+b is 12 or 13; and EO/PO are alkoxy moieties, preferably selected from ethoxy, propoxy, and mixed ethoxy/propoxy groups, wherein m is at least about 1, preferably within the range of from about 3 to about 30, more preferably from about 5 to about 20, and most preferably from about 5 to about 15.

Also preferred herein are polyoxyalkylene compounds of formula:

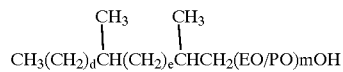

wherein:

d and e are integers and d+e is 10 or 1; and wherein further when d+e=10, d is an integer from 2 to 9 and e is an integer from 1 to 8;

when d+e=11, d is an integer from 2 to 10 and e is an integer from 1 to 9;

and EO/PO are alkoxy moieties, preferably selected from ethoxy, propoxy, and mixed ethoxy/propoxy groups, wherein m is at least about 1, preferably within the range of from about 3 to about 30, more preferably from about 5 to about 20, and most preferably from about 5 to about 15.

All percentages, ratios and proportions herein are by weight, unless otherwise specified. All temperatures are in degrees Celsius (° C) unless otherwise specified. All documents cited are in relevant part, incorporated herein by reference.

DETAILED DESCRIPTION OF THE INVENTION

The present invention relates to mid-chain branched primary alkyl polyoxyalkylene surfactants. The branched surfactant compositions comprise one or more mid-chain branched primary alkyl polyoxyalkylene surfactants having the formula

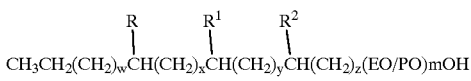

The surfactant mixtures of the present invention comprise molecules having a linear primary polyoxyalkylene chain backbone (i.e., the longest linear carbon chain which includes the alkoxylated carbon atom). These alkyl chain backbones comprise from 12 to 19 carbon atoms; and further the molecules comprise a branched primary alkyl moiety having at least a total of 14, but not more than 20, carbon atoms. In addition, the surfactant mixture has an average total number of carbon atoms for the branched primary alkyl moieties within the range of from greater than 14.5 to about 17.5. Thus, the present invention mixtures comprise at least one polyoxyalkylene compound having a longest linear carbon chain of not less than 12 carbon atoms or more than 19 carbon atoms, and the total number of carbon atoms including branching must be at least 14, and further the average total number of carbon atoms for the branched primary alkyl chains is within the range of greater than 14.5 to about 17.5.

For example, a C16 total carbon (in the alkyl chain) primary polyoxyalkylene surfactant having 15 carbon atoms in the backbone must have a methyl branching unit (either R, $R^1$ or $R^2$ is methyl) whereby the total number of carbon atoms in the molecule is 16.

R, $R^1$, and $R^2$ are each independently selected from hydrogen and $C_1$–$C_3$ alkyl (preferably hydrogen or $C_1$–$C_2$ alkyl, more preferably hydrogen or methyl, and most preferably methyl), provided R, $R^1$, and $R^2$ are not all hydrogen. Further, when z is 1, at least R or $R^1$ is not hydrogen.

Although for the purposes of the present invention surfactant compositions the above formula does not include molecules wherein the units R, $R^1$, and $R^2$ are all hydrogen (i.e., linear non-branched primary polyoxyalkylenes), it is to be recognized that the present invention compositions may still further comprise some amount of linear, non-branched primary polyoxyalkylene. Further, this linear non-branched primary polyoxyalkylene surfactant may be present as the result of the process used to manufacture the surfactant mixture having the requisite mid-chain branched primary polyoxyalkylenes according to the present invention, or for purposes of formulating detergent compositions some amount of linear non-branched primary polyoxyalkylene may be admixed into the final product formulation.

Further it is to be similarly recognized that non-alkoxylated mid-chain branched alcohol may comprise some amount of the present invention polyoxyalkylene-containing compositions. Such materials may be present as the result of incomplete alkoxylation of the alcohol used to prepare the polyoxyalkylene surfactant, or these alcohols may be separately added to the present invention detergent compositions along with a mid-chain branched polyoxyalkylene surfactant according to the present invention.

Further regarding the above formula, w is an integer from 0 to 13; x is an integer from 0 to 13; y is an integer from 0 to 13; z is an integer of at least 1; and w+x+y+z is an integer from 8 to 14.

EO/PO are alkoxy moieties, preferably selected from ethoxy, propoxy, and mixed ethoxy/propoxy groups, wherein m is at least about 1, preferably within the range of from about 3 to about 30, more preferably from about 5 to about 20, and most preferably from about 5 to about 15. The (EO/PO)m moiety may be either a distribution with average degree of alkoxylation (e.g., ethoxylation and/or propoxylation) corresponding to m, or it may be a single specific chain with alkoxylation (e.g., ethoxylation and/or propoxylation) of exactly the number of units corresponding to m.

Certain points of branching (i.e., the location along the chain of the R, $R^1$, and/or $R^2$ moieties in the above formula) are preferred over other points of branching along the backbone of the surfactant. The formula below illustrates the mid-chain branching range (i.e., where points of branching occur), preferred mid-chain branching range, and more preferred mid-chain branching range for mono-methyl substituted linear alkyl polyoxyalkylenes of the present invention.

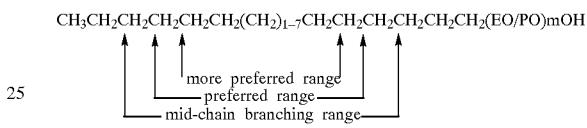

It should be noted that for the mono-methyl substituted surfactants these ranges exclude the two terminal carbon atoms of the chain and the two carbon atoms immediately adjacent to the EO/PO moiety. For surfactant mixtures comprising two or more of R, $R^1$, or $R^2$ being other than hydrogen, alkyl branching at the 2-carbon atom is within the scope of the present invention surfactants. Surfactants having chains longer than ethyl (i.e. $C_3$ alkyl substitutents) on the 2-carbon atom, however, are less preferred.

The formula below illustrates the mid-chain branching range, preferred mid-chain branching range, and more preferred mid-chain branching range for di-methyl substituted linear alkyl polyoxyal-kylenes of the present invention.

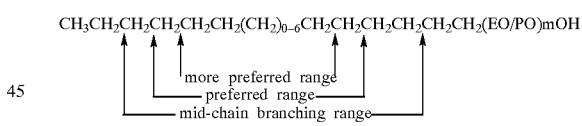

When di-alkyl substituted primary alkyl polyoxyalkylenes are combined with mono-substituted mid-chain branched primary alkyl polyoxyalkylenes, the di-alkyl substituted primary polyoxyalkylenes having one methyl substitution on the 2-carbon position and another methyl substitution in the preferred range as indicated above, are within the present composition surfactants.

The preferred surfactant mixtures of the present invention have at least 0.001%, more preferably at least 5%, most preferably at least 20% by weight, of the mixture one or more mid-chain branched primary alkyl polyoxyalkylenes having the formula

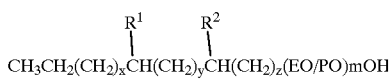

wherein the total number of carbon atoms (in the lipophilic portion of this molecule), including branching, is from 15 to 18, and wherein further for this surfactant mixture the average total number of carbon atoms in the branched primary alkyl moieties having the above formula is within the range of greater than 14.5 to about 17.5; $R^1$ and $R^2$ are each independently hydrogen or $C_1$–$C_4$ (preferably $C_1$–$C_3$) alkyl; x is from 0 to 1; y is from 0 to 11; z is at least 2; and x+y+z is from 9 to 13; provided $R^1$ and $R^2$ are not both hydrogen; and EO/PO are alkoxy moieties selected from ethoxy, propoxy, and mixed ethoxy/propoxy groups, wherein m is at least about 1, preferably within the range of from about 3 to about 30, more preferably from about 5 to about 20, and most preferably from about 5 to about 15.

Preferably, the mixtures of surfactant comprise at least 5%, preferably at least about 20%, of a mid chain branched primary alkyl polyoxyalkylene having $R^1$ and $R^2$ independently hydrogen or methyl, provided $R^1$ and $R^2$ are not both hydrogen; x+y is equal to 8, 9 or 10 and z is at least 2.

Preferred detergent compositions according to the present invention, for example one useful for laundering fabrics, comprise from about 0.001% to about 99% of a mixture of mid-chain branched primary alkyl polyoxyalkylene surfactants, said mixture comprising at least about 2% by weight of one or more mid-chain branched alkyl polyoxyalkylenes having the formula:

$$CH_3(CH_2)_a\overset{\underset{|}{CH_3}}{CH}(CH_2)_bCH_2(EO/PO)_mOH, \quad (I)$$

$$CH_3(CH_2)_d\overset{\underset{|}{CH_3}}{CH}(CH_2)_e\overset{\underset{|}{CH_3}}{CH}CH_2(EO/PO)_mOH, \quad (II)$$

or mixtures thereof; wherein a, b, d, and e are integers, a+b is from 10 to 16, d+e is from 8 to 14 and wherein further
when a+b=10, a is an integer from 2 to 9 and b is an integer from 1 to 8;
when a+b=11, a is an integer from 2 to 10 and b is an integer from 1 to 9;
when a+b=12, a is an integer from 2 to 11 and b is an integer from 1 to 10;
when a+b=13, a is an integer from 2 to 12 and b is an integer from 1 to 11;
when a+b=14, a is an integer from 2 to 13 and b is an integer from 1 to 12;
when a+b=15, a is an integer from 2 to 14 and b is an integer from 1 to 13;
when a+b=16, a is an integer from 2 to 15 and b is an integer from 1 to 14;
when d+e 8, d is an integer from 2 to 7 and e is an integer from 1 to 6;
when d+e=9, d is an integer from 2 to 8 and e is an integer from 1 to 7;
when d+e=10, d is an integer from 2 to 9 and e is an integer from 1 to 8;
when d+e=11, d is an integer from 2 to 10 and e is an integer from 1 to 9;
when d+e 12, d is an integer from 2 to 11 and e is an integer from 1 to 10;
when d+e=13, d is an integer from 2 to 12 and e is an integer from 1 to 11;
when d+e=14, d is an integer from 2 to 13 and e is an integer from 1 to 12;
and wherein further for this surfactant mixture the average total number of carbon atoms in the branched primary alkyl moieties having the above formulas is within the range of greater than 14.5 to about 17.5; and EO/PO are alkoxy moieties selected from ethoxy, propoxy, and mixed ethoxy/propoxy groups, wherein m is at least about 1, preferably within the range of from about 3 to about 30, more preferably from about 5 to about 20, and most preferably from about 5 to about 15.

Further, the present invention surfactant composition may comprise a mixture of branched primary alkyl polyoxyalkylenes having the formula $$CH_3CH_2(CH_2)_w\overset{\underset{|}{R}}{CH}(CH_2)_x\overset{\underset{|}{R^1}}{CH}(CH_2)_y\overset{\underset{|}{R^2}}{CH}(CH_2)_z(EO/PO)_mOH$$

wherein the total number of carbon atoms per molecule, including branching, is from 14 to 20, and wherein further for this surfactant mixture the average total number of carbon atoms in the branched primary alkyl moieties having the above formula is within the range of greater than 14.5 to about 17.5; R, $R^1$, and $R^2$ are each independently selected from hydrogen and $C_1$–$C_3$ alkyl, provided R, $R^1$, and $R^2$ are not all hydrogen; w is an integer from 0 to 13; x is an integer from 0 to 13; y is an integer from 0 to 13; z is an integer of at least 1; w+x+y+z is from 8 to 14; EO/PO are alkoxy moieties, preferably selected from ethoxy, propoxy, and mixed ethoxy/propoxy groups, wherein m is at least about 1, preferably within the range of from about 3 to about 30, more preferably from about 5 to about 20, and most preferably from about 5 to about 15; provided that when $R^2$ is $C_1$–$C_3$ alkyl the ratio of surfactants having z equal to 2 or greater to surfactants having z of 1 is at least about 1:1, preferably at least about 1.5:1, more preferably at least about 3:1, and most preferably at least about 4:1. Also preferred are surfactant compositions when $R^2$ is $C_1$–$C_3$ alkyl comprising less than about 50%, preferably less than about 40%, more preferably less than about 25%, most preferably less than about 20%, of branched primary alkyl polyoxyalkylene having the above formula wherein z equals The present invention further relates to novel mid-chain branched primary alkyl polyoxyalkylene surfactants having the formula $$CH_3CH_2(CH_2)_x\overset{\underset{|}{R^1}}{CH}(CH_2)_y\overset{\underset{|}{R^2}}{CH}(CH_2)_z(EO/PO)_mOH$$

wherein $R^1$ and $R^2$ are each independently hydrogen or $C_1$–$C_3$ alkyl; x is from 0 to 14; y is from 0 to 14; z is at least 2; x+y+z is from 7 to 17; and EO/PO are alkoxy moieties selected from ethoxy, propoxy, and mixed ethoxy/propoxy groups, wherein m is at least about 1, preferably within the range of from about 3 to about 30, more preferably from about 5 to about 20, and most preferably from about 5 to about 15; provided $R^1$ and $R^2$ are not both hydrogen.

$R^1$ and $R^2$ units are selected independently from hydrogen or $C_1$–$C_3$ alkyl (preferably hydrogen or $C_1$–$C_2$ alkyl; more preferably hydrogen or methyl) provided $R^1$ and $R^2$ are not both hydrogen.

For mid-chain branched primary polyoxyalkylenes of the present invention having more than one alkyl branch chain, the alkyl chain backbones comprise from 12 to 18 carbon atoms. The maximum number of carbons that comprise the mid-chain branched primary polyoxyalkylenes of the present invention, including all branches, is 20 carbon atoms.

Preferred novel polyoxyalkylene compounds have the formula:

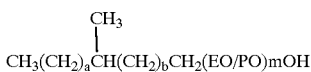

wherein: a and b are integers and a+b is 12 or 13, a is an integer from 2 to 11, b is an integer from 1 to 10, and EO/PO are alkoxy moieties, preferably selected from ethoxy, propoxy, and mixed ethoxy/propoxy groups, wherein m is at least about 1, preferably within the range of from about 3 to about 30, more preferably from about 5 to about 20, and most preferably from about 5 to about 15.

Also preferred novel mid-chain branched primary alkyl polyoxyalkylene compounds have the formula:

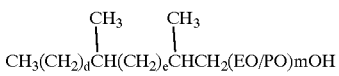

wherein:
d and e are integers and d+e is 10 or 11; and wherein further
  when d+e=10, d is an integer from 2 to 9 and e is an integer from 1 to 8;
when d+e=11, d is an integer from 2 to 10 and e is an integer from 1 to 9;
and EO/PO are alkoxy moieties, preferably selected from ethoxy, propoxy, and mixed ethoxy/propoxy groups, wherein m is at least about 1, preferably within the range of from about 3 to about 30, more preferably from about 5 to about 20, and most preferably from about 5 to about 15.

Preferred mono-methyl branched primary alkyl ethoxylates are selected from the group consisting of: 3-methyl pentadecanol ethoxylate, 4-methyl pentadecanol ethoxylate, 5-methyl pentadecanol ethoxylate, 6-methyl pentadecanol ethoxylate, 7-methyl pentadecanol ethoxylate, 8-methyl pentadecanol ethoxylate, 9-methyl pentadecanol ethoxylate, 10-methyl pentadecanol ethoxylate, 11-methyl pentadecanol ethoxylate, 12-methyl pentadecanol ethoxylate, 13-methyl pentadecanol ethoxylate, 3-methyl hexadecanol ethoxylate, 4-methyl hexadecanol ethoxylate, 5-methyl hexadecanol ethoxylate, 6-methyl hexadecanol ethoxylate, 7-methyl hexadecanol ethoxylate, 8-methyl hexadecanol ethoxylate, 9-methyl hexadecanol ethoxylate, 10-methyl hexadecanol ethoxylate, 11-methyl hexadecanol ethoxylate, 12-methyl hexadecanol ethoxylate, 13-methyl hexadecanol ethoxylate, 14-methyl hexadecanol ethoxylate, and mixtures thereof, wherein the compounds are ethoxylated with an average degree of ethoxylation of from about 5 to about 15.

Preferred di-methyl branched primary alkyl ethoxylates selected from the group consisting of: 2,3-methyl tetradecanol ethoxylate, 2,4-methyl tetradecanol ethoxylate, 2,5-methyl tetradecanol ethoxylate, 2,6-methyl tetradecanol ethoxylate, 2,7-methyl tetradecanol ethoxylate, 2,8-methyl tetradecanol ethoxylate, 2,9-methyl tetradecanol ethoxylate, 2,10-methyl tetradecanol ethoxylate, 2,11-methyl tetradecanol ethoxylate, 2,12-methyl tetradecanol ethoxylate, 2,3-methyl pentadecanol ethoxylate, 2,4-methyl pentadecanol ethoxylate, 2,5-methyl pentadecanol ethoxylate, 2,6-methyl pentadecanol ethoxylate, 2,7-methyl pentadecanol ethoxylate, 2,8-methyl pentadecanol ethoxylate, 2,9-methyl pentadecanol ethoxylate, 2,10-methyl pentadecanol ethoxylate, 2,11-methyl pentadecanol ethoxylate, 2,12-methyl pentadecanol ethoxylate, 2,13-methyl pentadecanol ethoxylate, and mixtures thereof, wherein the compounds are ethoxylated with an average degree of ethoxylation of from about 5 to about 15.

Preparation of Mid-chain Branched Polyoxyalkylenes

The following reaction scheme outlines a general approach to the preparation of the mid-chain branched primary alcohol useful for alkoxylating to prepare the mid-chain branched primary alkyl polyoxyalkylene surfactants of the present invention utilizing standard organic chemical reaction sequences familiar to those skilled in the art.

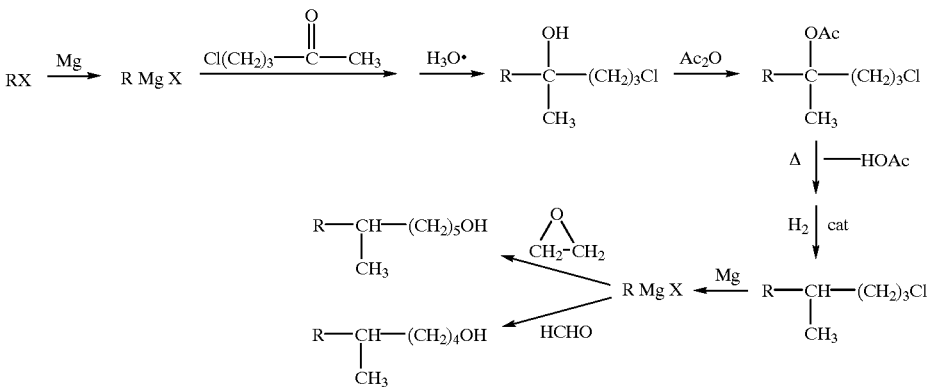

An alkyl halide is converted to a Grignard reagent and the Grignard is reacted with a haloketone. After conventional acid hydrolysis, acetylation and thermal elimination of acetic acid, an intermediate olefin is produced (not shown in the scheme) which is hydrogenated forthwith using any convenient hydrogenation catalyst such as Pd/C.

This route is favorable over others in that the branch, in this illustration a 5-methyl branch, is introduced early in the reaction sequence.

Formylation of the alkyl halide resulting from the first hydrogenation step yields alcohol product, as shown in the scheme. This can be alkoxylated using standard techniques to yield the final branched primary alkyl polyoxyalkylene surfactant. There is flexibility to extend the branching one additional carbon beyond that which is achieved by a single formylation. Such extension can, for example, be accomplished by reaction with ethylene oxide. See "Grignard Reactions of Nonmetallic Substances", M. S. Kharasch and O. Reinmuth, Prentice-Hall, N.Y., 1954; *J Org. Chem.,* J. Cason and W. R. Winans, Vol. 15 (1950), pp 139–147; *J. Org*

Chem., J. Cason et al., Vol. 13 (1948), pp 239–248; *J. Org Chem.*, J. Cason et al., Vol. 14 (1949), pp 147–154; and *J. Org Chem.*, J. Cason et al., Vol. 15 (1950), pp 135–138 all of which are incorporated herein by reference.

In variations of the above procedure, alternate haloketones or Grignard reagents may be used. PBr3 halogenation of the alcohol from formylation or ethoxylation can be used to accomplish an iterative chain extension.

The preferred mid-chained branched primary alkyl polyoxyalkylenes of the present invention can also be readily prepared as follows:

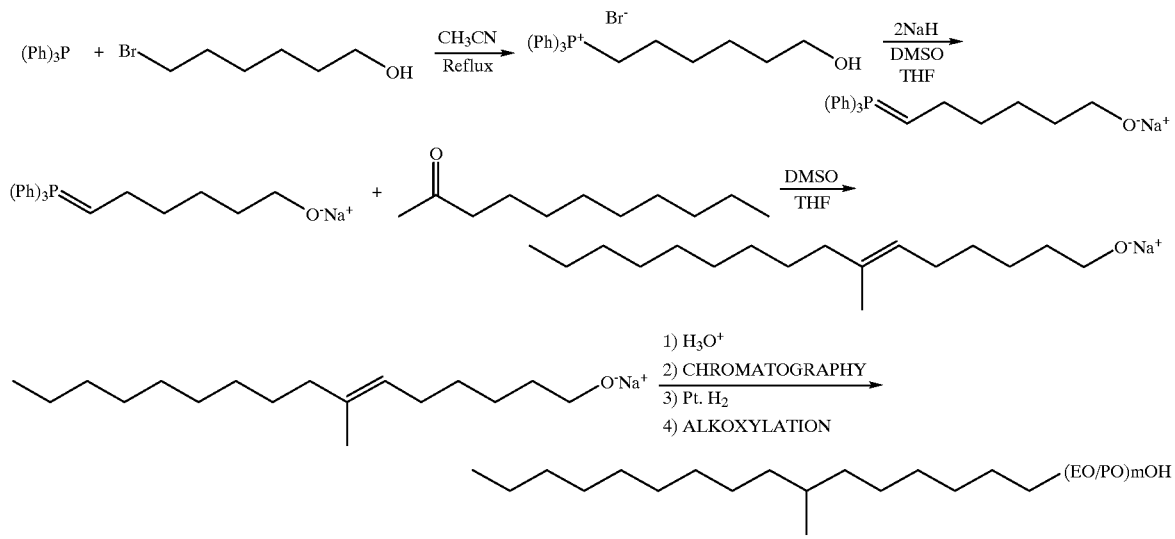

A conventional bromoalcohol is reacted with triphenylphosphine followed by sodium hydride, suitably in dimethylsulfoxide/tetrahydrofuran, to form a Wittig adduct. The Wittig adduct is reacted with an alpha methyl ketone, forming an internally unsaturated methyl-branched alcoholate. Hydrogenation followed by alkoxylation yields the desired mid-chain branched primary alkyl polyoxyalkylene. Although the Wittig approach does not allow the practitioner to extend the hydrocarbon chain, as in the Grignard sequence, the Wittig typically affords higher yields. See *Agricultural and Biological Chemistry*, M. Horiike et al., vol. 42 (1978), pp 1963–1965 included herein by reference.

Any alternative synthetic procedure in accordance with the invention may be used to prepare the branched primary alkyl polyoxyalkylenes. The mid-chain branched primary alkyl polyoxyalkylenes may, in addition be synthesized or formulated in the presence of the conventional homologs, for example any of those which may be formed in an industrial process which produces 2-alkyl branching as a result of hydroformylation. Mid-chain branched surfactant mixtures of the present invention are routinely added to other known commercial alkyl polyoxyalkylenes contained in the final laundry product formulation.

In certain preferred embodiments of the surfactant mixtures of the present invention, especially those derived from fossil fuel sources involving commercial processes, comprise at least 1 mid-chain branched primary alkyl polyoxyalkylene, preferably at least 2, more preferably at least 5, most preferably at least 8.

Particularly suitable for preparation of certain surfactant mixtures of the present invention are "oxo" reactions wherein a branched chain olefin is subjected to catalytic isomerization and hydroformylation prior to alkoxylation. The preferred processes resulting in such mixtures utilize fossil fuels as the starting material feedstock. Preferred processes utilize Oxo reaction on linear olefins (alpha or internal) with a limited amount of branching. Suitable olefins may be made by dimerization of linear alpha or internal olefins, by controlled oligomerization of low molecular weight linear olefins, by skeletal rearrangement of detergent range olefins, by dehydrogenation/skeletal rearrangement of detergent range paraffins, or by Fischer-Tropsch reaction, in any order. These reactions will in general be controlled to:

1) give a large proportion of olefins in the desired detergent range (while allowing for the addition of a carbon atom in the subsequent Oxo reaction),
2) produce a limited number of branches, preferably mid-chain,
3) produce $C_1$–$C_3$ branches, more preferably ethyl, most preferably methyl,
4) limit or eliminate gem dialkyl branching i.e. to avoid formation of quaternary carbon atoms. The suitable olefins can undergo Oxo reaction to give primary alcohols either directly or indirectly through the corresonding aldehydes. When an internal olefin is used, an Oxo catalyst is normally used which is capable of prior pre-isomerization of internal olefins primarily to alpha olefins. While a separately catalyzed (i.e. non-Oxo) internal to alpha isomerization could be effected, this is optional. On the other hand, if the olefin-forming step itself results directly in an alpha olefin (e.g. with high pressure Fischer-Tropsch olefins of detergent range), then use of a non-isomerizing Oxo catalyst is not only possible, but preferred.

The process described herein above gives the more preferred 5-methyl-hexadecyl polyoxyalkylene in higher yield than the less preferred 2,4-dimethylpentadecyl polyoxyalkylene. This mixture is desirable under the metes and bounds of the present invention in that each product comprises at total of 17 carbon atoms with linear alkyl chains having at least 13 carbon atoms.

The following examples provide methods for synthesizing various compounds useful in the present invention compositions.

19
EXAMPLE I

Preparation of 7-methylhexadecyl Ethoxylate (E2)

Synthesis of (6-hydroxyhexyl) Triphenylphosphonium Bromide

Into a 5 L, 3 neck round bottom flask fitted with nitrogen inlet, condenser, thermometer, mechanical stirring and nitrogen outlet is added 6-bromo-1-hexanol (500 g, 2.76 mol), triphenylphosphine (768 g, 2.9 mol) and acetonitrile (1800 ml) under nitrogen. The reaction mixture is heated to reflux for 72 hrs. The reaction mixture is cooled to room temperature and transferred into a 5 L beaker. The product is recrystallized from anhydrous ethyl ether (1.5 L) at 10° C. Vacuum filtration followed by washing with ethyl ether and drying in a vacuum oven at 50° C for 2 hrs. gives 1140 g of the desired product as white crystals.

Synthesis of 7-methylhexadecene-1-ol

Into a dried 5 L, 3 neck round bottom flask fitted with mechanical stirring, nitrogen inlet, dropping funnel, thermometer and nitrogen outlet is added 70.2 g of 60% sodium hydride (1.76 mol) in mineral oil. The mineral oil is removed by washing with hexanes. Anhydrous dimethyl sulfoxide (500 ml) is added to the flask and the mixture is heated to 70° C. until evolution of hydrogen stops. The reaction mixture is cooled to room temperature followed by addition of 1 L of anhydrous tetrahydrofuran. (6-hydroxyhexyl) triphenylphosphonium bromide (443.4 g, 1 mol) is slurried with warm anhydrous dimethyl sulfoxide (50° C., 500 ml) and slowly added to the reaction mixture through the dropping funnel while keeping it at 25–30° C. The mixture is stirred for 30 minutes at room temperature at which time 2-undecanone (187 g, 1.1 mol) is slowly added through a dropping funnel. Reaction is slightly exothermic and cooling is needed to maintain 25–30° C. The mixture is stirred for 18 hr. and then poured into a 5 L beaker containing 1 L purified water with stirring. The oil phase (top) is allowed to separate out in a separatory funnel and the water phase is removed. The water phase is washed with hexanes (500 ml) and the organic phase is separated and combined with the oil phase from the water wash. The organic mixture is then extracted with water 3 times (500 ml each) followed by vacuum distillation to collect the clear, oily product (132 g) at 140 C and 1 mm Hg.

Hydrogenation of 7-methylhexadecene-1-ol

Into a 3 L rocking autoclave liner is added 7-methylhexadecene-1-ol (130 g, 0.508 mol), methanol (300 ml) and platinum on carbon (10% by weight, 35 g). The mixture is hydrogenated at 180° C. under 1200 psig of hydrogen for 13 hrs., cooled and vacuum filtered thru Celite 545 with washing of the Celite 545, suitably with methylene chloride. If needed, the filtration can be repeated to eliminate traces of Pt catalyst, and magnesium sulfate can be used to dry the product. The solution of product is concentrated on a rotary evaporator to obtain a clear oil (124 g).

Alkoxylation of 7-methylhexadecanol

Into a dried 1 L 3 neck round bottom flask fitted with a nitrogen inlet, mechanical stirrer, and a y-tube fitted with a thermometer and a gas outlet is added the alcohol from the preceeding step. For purposes of removing trace amounts of moisture, the alcohol is sparged with nitrogen for about 30 minutes at 80–100° C. Continuing with a nitrogen sweep, sodium metal is added as the catalyst and allowed to melt with stirring at 120–140° C. With vigorous stirring, ethylene oxide gas is added in 140 minutes while keeping the reaction temperature at 120–140° C. After the correct weight (equal to two equivalents of ethylene oxide) has been added, nitrogen is swept through the apparatus for 20–30 minutes as the sample is allowed to cool. The desired 7-methylhexadecyl ethoxylate (average of 2 ethoxylates per molecule) product is then collected.

EXAMPLE II

Synthesis of 7-methylpentadecyl Ethoxylate (E8)

Synthesis of (6-hydroxyhexyl) Triphenylphosphonium Bromide

Into a 5 L, 3 neck round bottom flask fitted with nitrogen inlet, condenser, thermometer, mechanical stirring and nitrogen outlet is added 6-bromo-1-hexanol (500 g, 2.76 mol), triphenylphosphine (768 g, 2.9 mol) and acetonitrile (1800 ml) under nitrogen. The reaction mixture is heated to reflux for 72 hrs. The reaction mixture is cooled to room temperature and transferred into a 5 L beaker. The product is recrystallized from anhydrous ethyl ether (1.5 L) at 10° C. Vacuum filtration of the mixture followed by washing the white crystals with ethyl ether and drying in a vacuum oven at 50° C. for 2 hrs. gives 1140 g of the desired product.

Synthesis of 7-methylpentadecene-1-ol

Into a dried 5 L, 3 neck round bottom flask fitted with mechanical stirring, nitrogen inlet, dropping funnel, thermometer and nitrogen outlet is added 80 g of 60% sodium hydride (2.0 mol) in mineral oil. The mineral oil is removed by washing with hexanes. Anhydrous dimethyl sulfoxide (500 ml) is added to the flask and heated to 70° C. until evolution of hydrogen stops. The reaction mixture is cooled to room temperature followed by addition of 1 L of anhydrous tetrahydrofuran. (6-hydroxyhexyl) triphenylphosphonium bromide (443.4 g, 1 mol) is slurried with warm anhydrous dimethyl sulfoxide (50° C., 500 ml) and slowly added to the reaction mixture thru the dropping funnel while keeping the reaction at 25–30° C. The reaction is stirred for 30 minutes at room temperature at which time 2-decanone (171.9 g, 1.1 mol) is slowly added thru a dropping funnel. Reaction is slightly exothermic and cooling is needed to maintain 25–30° C. Mixture is stirred for 18 hrs. and then poured into a separatory funnel containing 600 ml of purified water and 300 ml of hexanes. After shaking the oil phase (top) is allowed to separate out and the water phase is removed. The extractions of the oil phase are continued using water until both phases are clear. The organic phase is collected, vacuum distilled and purified by liquid chromatography (90:10 hexanes:ethyl acetate, silica gel stationary phase) to obtain a clear, oily product (119.1 g).

Hydrogenation of 7-methylpentadecene-1-ol

Into a 3 L rocking autoclave glass liner (Autoclave Engineers) is added 7-Methylpentadecene-1-ol (122 g, 0.508 mol), methanol (300 ml) and platinum on carbon (10% by weight, 40 g). The mixture is hydrogenated at 180° C. under 1200 psig of hydrogen for 13 hrs., cooled and vacuum filtered thru Celite 545 with washing of Celite 545 with methylene chloride. The organic mixture is still dark from platinum catalyst so the filtration procedure is repeated with concentration on a rotary evaporator; dilution is carried out with methylene chloride (500 ml) and magnesium sulfate is aded to dry product. Vacuum filter thru Celite 545 and concentrate filtrate on a rotary evaporator to obtain a clear oil (119 g).

Alkoxylation of 7-methylpentadecanol

Into a dried 1 L 3 neck round bottom flask fitted with a nitrogen inlet, mechanical stirrer, and a y-tube fitted with a thermometer and a gas outlet is added the alcohol from the preceeding step. For purposes of removing trace amounts of moisture, the alcohol is sparged with nitrogen for about 30 minutes at 80–100° C. Continuing with a nitrogen sweep, sodium metal is added as the catalyst and allowed to melt with stirring at 120–140° C. With vigorous stirring, ethylene oxide gas is added in 140 minutes while keeping the reaction temperature at 120–140° C. After the correct weight (equal to eight equivalents of ethylene oxide) has been added, nitrogen is swept through the apparatus for 20–30 minutes as the sample is allowed to cool. The desired 7-methylpentadecyl ethoxylate (average of 8 ethoxylates per molecule) product is then collected.

EXAMPLE III

Synthesis of 7-methylheptadecyl Ethoxylate (E5)

Synthesis of (6-Hydroxyhexyl) Triphenylphosphonium Bromide

Into a 5 L, 3 neck round bottom flask fitted with nitrogen inlet, condenser, thermometer, mechanical stirring and nitrogen outlet is added 6-bromo-1-hexanol (500 g, 2.76 mol), triphenylphosphine (768 g, 2.9 mol) and acetonitrile (1800 ml) under nitrogen. The reaction mixture is heated to reflux for 72 hrs. The reaction mixture is cooled to room temperature and transferred into a 5 L beaker. The product is recrystallized from anhydrous ethyl ether (1.5 L) at 10° C. Vacuum filtration of the mixture followed by washing the white crystals with ethyl ether and drying in a vacuum oven at 50° C. for 2 hrs. gives 1140 g of the desired product.

Synthesis of 7-methylheptadecene-1-ol

Into a dried 5 L, 3 neck round bottom flask fitted with mechanical stirring, nitrogen inlet, dropping funnel, thermometer and nitrogen outlet is added 80 g of 60% sodium hydride (2.0 mol) in mineral oil. The mineral oil is removed by washing with hexanes. Anhydrous dimethyl sulfoxide (500 ml) is added to the flask and heated to 70° C. until evolution of hydrogen stops. The reaction mixture is cooled to room temperature followed by addition of 1 L of anhydrous tetrahydrofuran. (6-hydroxyhexyl) triphenylphosphonium bromide (443.4 g, 1 mol) is slurried with warm anhydrous dimethyl sulfoxide (50° C., 500 ml) and slowly added to the reaction mixture thru the dropping funnel while keeping the reaction at 25–30° C. The reaction is stirred for 30 minutes at room temperature at which time 2-dodecanone (184.3 g, 1.1 mol) is slowly added thru a dropping funnel. Reaction is slightly exothermic and cooling is needed to maintain 25–30° C. Mixture is stirred for 18 hrs. and then poured into a separatory funnel containing 600 ml of purified water and 300 ml of hexanes. After shaking the oil phase (top) is allowed to separate out and the water phase is removed which is cloudy. The extractions are continued using water until the water phase and the organic phase become clear. The organic phase is collected and purified by liquid chromatography (mobile phase-hexanes, stationary phase-silica gel ) to obtain a clear, oily product (116 g). HNMR of the final product (in deuterium oxide) indicates a $CH_2$—$OSO_3$— triplet at the 3.8 ppm resonance, $CH_2$—$CH_2$—$OSO_3$— multiplet at the 1.5 ppm resonance, $CH_2$ of the alkyl chain at the 0.9–1.3 ppm resonance and CH—$CH_3$ branch point overlapping the R—$CH_2CH_3$ terminal methyl group at the 0.8 ppm resonance.

Hydrogenation of 7-methylheptadecene-1-ol

Into a 3 L rocking autoclave glass liner (Autoclave Engineers) is added 7-Methylheptadecene-1-ol (116 g, 0.433 mol), methanol (300 ml) and platinum on carbon (10% by weight, 40 g). The mixture is hydrogenated at 180° C. under 1200 psig of hydrogen for 13 hrs., cooled and vacuum filtered thru Celite 545 with washing of Celite 545 with methylene chloride. Vacuum filter thru Celite 545 and concentrate filtrate on a rotary evaporator to obtain a clear oil (108 g).

Alkoxylation of 7-methylheptadecanol

Into a dried 1 L 3 neck round bottom flask fitted with a nitrogen inlet, mechanical stirrer, and a y-tube fitted with a thermometer and a gas outlet is added the alcohol from the preceeding step. For purposes of removing trace amounts of moisture, the alcohol is sparged with nitrogen for about 30 minutes at 80–100° C. Continuing with a nitrogen sweep, sodium metal is added as the catalyst and allowed to melt with stirring at 120–140° C. With vigorous stirring, ethylene oxide gas is added in 140 minutes while keeping the reaction temperature at 120–140° C. After the correct weight (equal to 5 equivalents of ethylene oxide) has been added, nitrogen is swept through the apparatus for 20–30 minutes as the sample is allowed to cool. The desired 7-methylheptadecyl ethoxylate (average of 5 ethoxylates per molecule) product is then collected.

EXAMPLE IV

7-Methylheptadecyl Ethoxylate (E9.0)

Into a dried 1 L 3 neck round bottom flask fitted with a nitrogen inlet, mechanical stirrer, and a y-tube fitted with a thermometer and a gas outlet is added the alcohol from the preceeding example. For purposes of removing trace amounts of moisture, the alcohol is sparged with nitrogen for about 30 minutes at 80–100° C. Continuing with a nitrogen sweep, sodium metal is added as the catalyst and allowed to melt with stirring at 120–140° C. With vigorous stirring, ethylene oxide gas is added in 140 minutes while keeping the reaction temperature at 120–140° C. After the correct weight (equal to 9.0 equivalents of ethylene oxide) has been added, nitrogen is swept through the apparatus for 20–30 minutes as the sample is allowed to cool. The desired 7-methylheptadecyl ethoxylate (average of 9.0 ethoxylates per molecule) product is then collected.

EXAMPLE V

The following Shell Research experimental test alcohol samples are ethoxylated (average ethoxylation of 2.5) by the following procedure.

| $^{13}$C-NMR Results For Branched Alcohols Prepared | | | |
|---|---|---|---|
| Total Number of Carbons | 16 | 17 | 18 |
| Avg. Number of Branches per Molecule | 2.0 | 1.7 | 2.1 |
| Average Branch Position Relative To Hydroxyl Carbon | | | |
| % at C4 and higher | 56% | 55% | 52% |
| % at C3 | 26% | 21% | 25% |
| % at C2 | 18% | 24% | 23% |

-continued

13C-NMR Results For Branched Alcohols Prepared

| Type of Branching | | | |
|---|---|---|---|
| % propyl and higher | 31% | 35% | 30% |
| % ethyl | 12% | 10% | 12% |
| % methyl | 57% | 55% | 58% |

Into a dried 250 ml 3 neck round bottom flask fitted with a nitrogen inlet, mechanical stirrer, and a y-tube fitted with a thermometer and a gas outlet is added the C 16 alcohol (48.4 g, 0.2 mol) above. For purposes of removing trace amounts of moisture, the alcohol is sparged with nitrogen for about 30 minutes at 80–100° C. Continuing with a nitrogen sweep, sodium metal (0.23 g, 0.01 mol) is added as the catalyst and allowed to melt with stirring at 120–140° C. With vigorous stirring, ethylene oxide gas (22 g, 0.5 mol) is added in 140 minutes while keeping the reaction temperature at 120–140° C. After the correct weight of ethylene oxide (average 2.5 ethoxylates per molecule) has been added, nitrogen is swept through the apparatus for 20–30 minutes as the sample is allowed to cool. The gold liquid product (69 g, 0.196 mol) is bottled under nitrogen.

The following two analytical methods for characterizing branching in the present invention surfactant compositions are useful:

1) Separation and Identification of Components in Fatty Alcohols prior to alkoxylation. The position and length of branching found in the precursor fatty alcohol materials is determined by GC/MS techniques [see: D. J. Harvey, Biomed, Environ. Mass Spectrum (1989). 18(9), 719–23; D. J. Harvey, J. M. Tiffany, J. Chromatogr. (1984), 301(1), 173–87; K. A. Karlsson, B. E. Samuelsson, G. O. Steen, Chem. Phys. Lipids (1973), 11(1), 17–38].

2) Identification of Separated Fatty Alcohol Components prior to alkoxylation by MS/MS techniques. The position and length of branching is also determinable by Ion Spray-MS/MS or FAB-MS/MS techniques on previously isolated fatty alcohol components.

Having identified isolated alcohol components, alkoxylation of the isolated alcohols yields standards useful for calibrating and interpreting GC chromatograms of mid-chain branched primary alkyl polyoxyalkylene surfactants.

The average total carbon atoms of the branched primary alkyl polyoxyalkylenes herein can be calculated from the hydroxyl value of the precursor fatty alcohol mix according to common procedures, such as outlined in "Bailey's Industrial Oil and Fat Products", Volume 2, Fourth Edition, edited by Daniel Swern, pp. 440–441.

INDUSTRIAL APPLICABILITY

Branched-chain primary polyoxyalkylene surfactants of the type herein can be used in all manner of cleaning compositions. The detergent compositions of the invention thus may also contain additional detergent components. The precise nature of these additional components, and levels of incorporation thereof will depend on the physical form of the composition, and the precise nature of the cleaning operation for which it is to be used. The longer-chain derivatives are more soluble than expected and the shorter-chain derivatives clean better than expected. Cleaning compositions herein include, but are not limited to: granular, bar-form and liquid laundry detergents; liquid hand dishwashing compositions; liquid, gel and bar-form personal cleansing products; shampoos; dentifrices; hard surface cleaners, and the like. Such compositions can contain a variety of conventional detersive ingredients.

The following listing of such ingredients is for the convenience of the formulator, and not by way of limitation of the types of ingredients which can be used with the branched-chain surfactants herein. The compositions of the invention preferably contain one or more additional detergent components selected from surfactants, builders, alkalinity system, organic polymeric compounds, suds suppressors, soil suspension and anti-redeposition agents and corrosion inhibitors.

Bleaching Compounds—Bleaching Agents and Bleach Activators—The detergent compositions herein preferably further contain bleaching agents or bleaching compositions containing a bleaching agent and one or more bleach activators. Bleaching agents will typically be at levels of from about 1% to about 30%, more typically from about 5% to about 20%, of the detergent composition, especially for fabric laundering. If present, the amount of bleach activators will typically be from about 0.1% to about 60%, more typically from about 0.5% to about 40% of the bleaching composition comprising the bleaching agent-plus-bleach activator.

The bleaching agents used herein can be any of the bleaching agents useful for detergent compositions in textile cleaning, hard surface cleaning, or other cleaning purposes that are now known or become known. These include oxygen bleaches as well as other bleaching agents. Perborate bleaches, e.g., sodium perborate (e.g., mono- or tetra-hydrate) can be used herein.

Another category of bleaching agent that can be used without restriction encompasses percarboxylic acid bleaching agents and salts thereof. Suitable examples of this class of agents include magnesium monoperoxyphthalate hexahydrate, the magnesium salt of metachloro perbenzoic acid, 4-nonylamino-4-oxoperoxybutyric acid and diperoxy-dodecanedioic acid. Such bleaching agents are disclosed in U.S. Pat. No. 4,483,781, Hartman, issued Nov. 20, 1984, U.S. Patent Application 740,446, Burns et al, filed Jun. 3, 1985, European Patent Application 0,133,354, Banks et al, published Feb. 20, 1985, and U.S. Pat. No. 4,412,934, Chung et al, issued Nov. 1, 1983. Highly preferred bleaching agents also include 6-nonylamino-6-oxoperoxycaproic acid as described in U.S. Pat. No. 4,634,551, issued Jan. 6, 1987 to Burns et al.

Peroxygen bleaching agents can also be used. Suitable peroxygen bleaching compounds include sodium carbonate peroxyhydrate and equivalent "percarbonate" bleaches, sodium pyrophosphate peroxyhydrate, urea peroxyhydrate, and sodium peroxide. Persulfate bleach (e.g., OXONE, manufactured commercially by DuPont) can also be used.

A preferred percarbonate bleach comprises dry particles having an average particle size in the range from about 500 micrometers to about 1,000 micrometers, not more than about 10% by weight of said particles being smaller than about 200 micrometers and not more than about 10% by weight of said particles being larger than about 1,250 micrometers. Optionally, the percarbonate can be coated with silicate, borate or water-soluble surfactants. Percarbonate is available from various commercial sources such as FMC, Solvay and Tokai Denka.

Mixtures of bleaching agents can also be used.

Peroxygen bleaching agents, the perborates, the percarbonates, etc., are preferably combined with bleach activators, which lead to the in situ production in aqueous solution (i.e., during the washing process) of the peroxy acid corresponding to the bleach activator. Various nonlimiting examples of activators are disclosed in U.S. Pat. No. 4,915, 854, issued Apr. 10, 1990 to Mao et al, and U.S. Pat. No. 4,412,934. The nonanoyloxybenzene sulfonate (NOBS) and tetraacetyl ethylene diamine (TAED) activators are typical, and mixtures thereof can also be used. See also U.S. Pat. No. 4,634,551 for other typical bleaches and activators useful herein.

Highly preferred amido-derived bleach activators are those of the formulae:

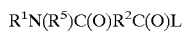

or

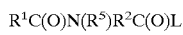

wherein $R^1$ is an alkyl group containing from about 6 to about 12 carbon atoms, $R^2$ is an alkylene containing from 1 to about 6 carbon atoms, $R^5$ is H or alkyl, aryl, or alkaryl containing from about 1 to about 10 carbon atoms, and L is any suitable leaving group. A leaving group is any group that is displaced from the bleach activator as a consequence of the nucleophilic attack on the bleach activator by the perhydrolysis anion. A preferred leaving group is phenyl sulfonate.

Preferred examples of bleach activators of the above formulae include (6-octanamido-caproyl) oxybenzenesulfonate, (6-nonanamidocaproyl) oxybenzenesulfonate, (6-decanamido-caproyl) oxybenzenesulfonate, and mixtures thereof as described in U.S. Pat. No. 4,634,551, incorporated herein by reference.

Another class of bleach activators comprises the benzoxazin-type activators disclosed by Hodge et al in U.S. Pat. No. 4,966,723, issued Oct. 30, 1990, incorporated herein by reference. A highly preferred activator of the benzoxazin-type is:

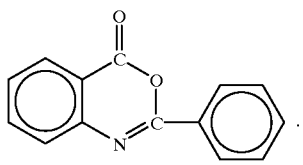

Still another class of preferred bleach activators includes the acyl lactam activators, especially acyl caprolactams and acyl valerolactams of the formulae:

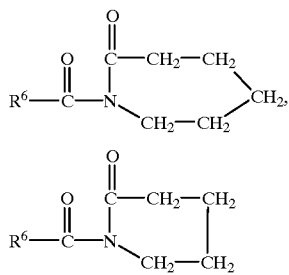

wherein $R^6$ is H or an alkyl, aryl, alkoxyaryl, or alkaryl group containing from 1 to about 12 carbon atoms. Highly preferred lactam activators include benzoyl caprolactam, octanoyl caprolactam, 3,5,5-trimethylhexanoyl caprolactam, nonanoyl caprolactam, decanoyl caprolactam, undecenoyl caprolactam, benzoyl valerolactam, octanoyl valerolactam, decanoyl valerolactam, undecenoyl valerolactam, nonanoyl valerolactam, 3,5,5-trimethylhexanoyl valerolactam and mixtures thereof. See also U.S. Pat. No. 4,545,784, issued to Sanderson, Oct. 8, 1985, incorporated herein by reference, which discloses acyl caprolactams, including benzoyl caprolactam, adsorbed into sodium perborate.

Bleaching agents other than oxygen bleaching agents are also known in the art and can be utilized herein. One type of non-oxygen bleaching agent of particular interest includes photoactivated bleaching agents such as the sulfonated zinc and/or aluminum phthalocyanines. See U.S. Pat. No. 4,033, 718, issued Jul. 5, 1977 to Holcombe et al. If used, detergent compositions will typically contain from about 0.025% to about 1.25%, by weight, of such bleaches, especially sulfonate zinc phthalocyanine.

If desired, the bleaching compounds can be catalyzed by means of a manganese compound. Such compounds are well known in the art and include, for example, the manganese-based catalysts disclosed in U.S. Pat. No. 5,246,621, U.S. Pat. No. 5,244,594; U.S. Pat. No. 5,194,416; U.S. Pat. No. 5,114,606; and European Pat. App. Pub. Nos. 549,271A1, 549,272A1, 544,440A2, and 544,490A1; Preferred examples of these catalysts include $Mn^{IV}{}_2(u\text{-}O)_3(1,4,7\text{-trimethyl-}1,4,7\text{-triazacyclononane})_2\text{-}(PF_6)_2$, $Mn^{III}{}_2(u\text{-}O)_1(u\text{-}OAc)_2(1,4,7\text{-trimethyl-}1,4,7\text{-triazacyclononane})_2(ClO_4)_2$, $Mn^{IV}{}_4(u\text{-}O)_6(1,4,7\text{-triazacyclononane})_4(ClO_4)_4$, $Mn^{III}Mn^{IV}{}_4(u\text{-}O)_1 (u\text{-}OAc)_2\text{-}(1,4,7\text{-trimethyl-}1,4,7\text{-triazacyclononane})_2(ClO_4)_3$, $Mn^{IV}(1,4,7\text{-trimethyl-}1,4,7\text{-triazacyclononane})\text{-}(OCH_3)_3(PF_6)$, and mixtures thereof. Other metal-based bleach catalysts include those disclosed in U.S. Pat. No. 4,430,243 and U.S. Pat. No. 5,114,611. The use of manganese with various complex ligands to enhance bleaching is also reported in the following U.S. Pat. Nos. 4,728,455; 5,284,944; 5,246,612; 5,256,779; 5,280,117; 5,274,147; 5,153,161; and 5,227,084.

As a practical matter, and not by way of limitation, the compositions and processes herein can be adjusted to provide on the order of at least one part per ten million of the active bleach catalyst species in the aqueous washing liquor, and will preferably provide from about 0.1 ppm to about 700 ppm, more preferably from about 1 ppm to about 500 ppm, of the catalyst species in the laundry liquor.

Cobalt bleach catalysts useful herein are known, and are described, for example, in M. L. Tobe, "Base Hydrolysis of Transition-Metal Complexes" Adv. Inorg. Bioinorg. Mech., (1983), 2, pages 1–94. The most preferred cobalt catalyst useful herein are cobalt pentaamine acetate salts having the formula $[Co(NH_3)_5OAc] T_y$, wherein "OAc" represents an acetate moiety and "$T_y$" is an anion, and especially cobalt pentaamine acetate chloride, $[Co(NH_3)_5OAc]Cl_2$; as well as $[Co(NH_3)_5OAc](OAc)_2$; $[Co(NH_3)_5OAc](PF_6)_2$; $[Co(NH_3)_5OAc](SO_4)$; $[Co(NH_3)_5OAc](BF_4)_2$; and $[Co(NH_3)_5OAc](NO_3)_2$ (herein "PAC").

These cobalt catalysts are readily prepared by known procedures, such as taught for example in the Tobe article and the references cited therein, in U.S. Pat. No. 4,810,410, to Diakun et al, issued Mar. 7, 1989, J. Chem. Ed. (1989), 66 (12). 1043–45; The Synthesis and Characterization of Inorganic Compounds, W. L. Jolly (Prentice-Hall; 1970), pp. 461–3; Inorg. Chem., 18, 1497–1502 (1979); Inorg. Chem., 21, 2881–2885 (1982); Inorg. Chem., 18, 2023–2025 (1979); Inorg. Synthesis, 173–176 (1960); and Journal of Physical Chemistry, 56, 22–25 (1952).

As a practical matter, and not by way of limitation, the compositions and cleaning processes herein can be adjusted to provide on the order of at least one part per hundred million of the active bleach catalyst species in the aqueous washing medium, and will preferably provide from about 0.01 ppm to about 25 ppm, more preferably from about 0.05 ppm to about 10 ppm, and most preferably from about 0.1 ppm to about 5 ppm, of the bleach catalyst species in the wash liquor. In order to obtain such levels in the wash liquor of an automatic washing process, typical compositions herein will comprise from about 0.0005% to about 0.2%, more preferably from about 0.004% to about 0.08%, of bleach catalyst, especially manganese or cobalt catalysts, by weight of the cleaning compositions.

Enzymes—Enzymes are preferably included in the present detergent compositions for a variety of purposes, including removal of protein-based, carbohydrate-based, or triglyceride-based stains from substrates, for the prevention of refugee dye transfer in fabric laundering, and for fabric restoration. Suitable enzymes include proteases, amylases, lipases, cellulases, peroxidases, and mixtures thereof of any suitable origin, such as vegetable, animal, bacterial, fungal and yeast origin. Preferred selections are influenced by factors such as pH-activity and/or stability optima, thermostability, and stability to active detergents, builders and the like. In this respect bacterial or fungal enzymes are preferred, such as bacterial amylases and proteases, and fungal cellulases.

"Detersive enzyme", as used herein, means any enzyme having a cleaning, stain removing or otherwise beneficial effect in a laundry, hard surface cleaning or personal care detergent composition. Preferred detersive enzymes are hydrolases such as proteases, amylases and lipases. Preferred enzymes for laundry purposes include, but are not limited to, proteases, cellulases, lipases and peroxidases. Highly preferred for automatic dishwashing are amylases and/or proteases, including both current commercially available types and improved types which, though more and more bleach compatible though successive improvements, have a remaining degree of bleach deactivation susceptibility.

Enzymes are normally incorporated into detergent or detergent additive compositions at levels sufficient to provide a "cleaning-effective amount". The term "cleaning effective amount" refers to any amount capable of producing a cleaning, stain removal, soil removal, whitening, deodorizing, or freshness improving effect on substrates such as fabrics, dishware and the like. In practical terms for current commercial preparations, typical amounts are up to about 5 mg by weight, more typically 0.01 mg to 3 mg, of active enzyme per gram of the detergent composition. Stated otherwise, the compositions herein will typically comprise from 0.001% to 5%, preferably 0.01%–1% by weight of a commercial enzyme preparation. Protease enzymes are usually present in such commercial preparations at levels sufficient to provide from 0.005 to 0.1 Anson units (AU) of activity per gram of composition. For certain detergents, such as in automatic dishwashing, it may be desirable to increase the active enzyme content of the commercial preparation in order to minimize the total amount of non-catalytically active materials and thereby improve spotting/filming or other end-results. Higher active levels may also be desirable in highly concentrated detergent formulations.

Suitable examples of proteases are the subtilisins which are obtained from particular strains of B. subtilis and B. licheniformis. One suitable protease is obtained from a strain of Bacillus, having maximum activity throughout the pH range of 8–12, developed and sold as ESPERASE® by Novo Industries A/S of Denmark, hereinafter "Novo". The preparation of this enzyme and analogous enzymes is described in GB 1,243,784 to Novo. Other suitable proteases include ALCALASE® and SAVINASE® from Novo and MAXATASE® from International Bio-Synthetics, Inc., The Netherlands; as well as Protease A as disclosed in EP 130,756 A, Jan. 9, 1985 and Protease B as disclosed in EP 303,761 A, Apr. 28, 1987 and EP 130,756 A, Jan. 9, 1985. See also a high pH protease from Bacillus sp. NCIMB 40338 described in WO 9318140 A to Novo. Enzymatic detergents comprising protease, one or more other enzymes, and a reversible protease inhibitor are described in WO 9203529 A to Novo. Other preferred proteases include those of WO 9510591 A to Procter & Gamble. When desired, a protease having decreased adsorption and increased hydrolysis is available as described in WO 9507791 to Procter & Gamble. A recombinant trypsin-like protease for detergents suitable herein is described in WO 9425583 to Novo.

In more detail, an especially preferred protease, referred to as "Protease D" is a carbonyl hydrolase variant having an amino acid sequence not found in nature, which is derived from a precursor carbonyl hydrolase by substituting a different amino acid for a plurality of amino acid residues at a position in said carbonyl hydrolase equivalent to position +76, preferably also in combination with one or more amino acid residue positions equivalent to those selected from the group consisting of +99, +101, +103, +104, +107, +123, +27, +105, +109, +126, +128, +135, +156, +166, +195, +197, +204, +206, +210, +216, +217, +218, +222, +260, +265, and/or +274 according to the numbering of Bacillus amyloliquefaciens subtilisin, as described in WO 95/10615 published Apr. 20, 1995 by Genencor International.

Useful proteases are also described in PCT publications: WO 95/30010 published Nov. 9, 1995 by The Procter & Gamble Company; WO 95/30011 published Nov. 9, 1995 by The Procter & Gamble Company; WO 95/29979 published Nov. 9, 1995 by The Procter & Gamble Company.

Amylases suitable herein, especially for, but not limited to automatic dishwashing purposes, include, for example, (x-amylases described in GB 1,296,839 to Novo; RAPIDASE®, International Bio-Synthetics, Inc. and TERMAMYL®, Novo. FUNGAMYL® from Novo is especially useful. Engineering of enzymes for improved stability, e.g., oxidative stability, is known. See, for example J. Biological Chem., Vol. 260, No. 11, June 1985, pp. 6518–6521. Certain preferred embodiments of the present compositions can make use of amylases having improved stability in detergents such as automatic dishwashing types, especially improved oxidative stability as measured against a reference-point of TERMAMYL® in commercial use in 1993. These preferred amylases herein share the characteristic of being "stability-enhanced" amylases, characterized, at a minimum, by a measurable improvement in one or more of: oxidative stability, e.g., to hydrogen peroxide/tetraacetylethylenediamine in buffered solution at pH 9–10; thermal stability, e.g., at common wash temperatures such as about 60° C.; or alkaline stability, e.g., at a pH from about 8 to about 11, measured versus the above-identified reference-point amylase. Stability can be measured using any of the art-disclosed technical tests. See, for example, references disclosed in WO 9402597. Stability-enhanced amylases can be obtained from Novo or from Genencor International. One class of highly preferred amylases herein have the commonality of being derived using site-directed mutagenesis from one or more of the Bacillus amylases, especially the Bacillus α-amylases, regardless of whether one, two or multiple amylase strains are the immediate precursors. Oxidative stability-enhanced amylases vs. the above-identified reference amylase are preferred for use, especially in bleaching, more preferably oxygen bleaching, as distinct from chlorine bleaching, detergent compositions herein. Such preferred amylases include (a) an amylase according to the hereinbefore incorporated WO 9402597, Novo, Feb. 3, 1994, as further illustrated by a mutant in which substitution is made, using alanine or threonine, preferably threonine, of the methionine residue located in position 197 of the *B. licheniformis* alpha-amylase, known as TERMAMYL®, or the homologous position variation of a similar parent amylase, such as *B. amyloliquefaciens, B. subtilis,* or *B. stearothermophilus*; (b) stability-enhanced amylases as described by Genencor International in a paper entitled "Oxidatively Resistant alpha-Amylases" presented at the 207th American Chemical Society National Meeting, Mar. 13–17 1994, by C. Mitchinson. Therein it was noted that bleaches in automatic dishwashing detergents inactivate alpha-amylases but that improved oxidative stability amylases have been made by Genencor from *B. licheniformis* NCIB8061. Methionine (Met) was identified as the most likely residue to be modified. Met was substituted, one at a time, in positions 8, 15, 197, 256, 304, 366 and 438 leading to specific mutants, particularly important being M197L and M197T with the M197T variant being the most stable expressed variant. Stability was measured in CASCADE® and SUNLIGHT®; (c) particularly preferred amylases herein include amylase variants having additional modification in the immediate parent as described in WO 9510603 A and are available from the assignee, Novo, as DURAMYL®. Other particularly preferred oxidative stability enhanced amylase include those described in WO 9418314 to Genencor International and WO 9402597 to Novo. Any other oxidative stability-enhanced amylase can be used, for example as derived by site-directed mutagenesis from known chimeric, hybrid or simple mutant parent forms of available amylases. Other preferred enzyme modifications are accessible. See WO 9509909 A to Novo.

Other amylase enzymes include those described in WO 95/26397 and in co-pending application by Novo Nordisk PCT/DK96/00056. Specific amylase enzymes for use in the detergent compositions of the present invention include α-amylases characterized by having a specific activity at least 25% higher than the specific activity of Termamyl® at a temperature range of 25° C. to 55° C. and at a pH value in the range of 8 to 10, measured by the Phadebas® α-amylase activity assay. (Such Phadebas® α-amylase activity assay is described at pages 9–10, WO 95/26397.) Also included herein are α-amylases which are at least 80% homologous with the amino acid sequences shown in the SEQ ID listings in the references. These enzymes are preferably incorporated into laundry detergent compositions at a level from 0.00018% to 0.060% pure enzyme by weight of the total composition, more preferably from 0.00024% to 0.048% pure enzyme by weight of the total-composition.

Cellulases usable herein include both bacterial and fungal types, preferably having a pH optimum between 5 and 9.5. U.S. Pat. No. 4,435,307, Barbesgoard et al, Mar. 6, 1984, discloses suitable fungal cellulases from *Humicola insolens* or Humicola strain DSM 1800 or a cellulase 212-producing fungus belonging to the genus Aeromonas, and cellulase extracted from the hepatopancreas of a marine mollusk, Dolabella Auricula Solander. Suitable cellulases are also disclosed in GB-A-2.075.028; GB-A-2.095.275 and DE-OS-2.247.832. CAREZYME® and CELLUZYME® (Novo) are especially useful. See also WO 9117243 to Novo.

Suitable lipase enzymes for detergent usage include those produced by microorganisms of the Pseudomonas group, such as *Pseudomonas stutzeri* ATCC 19.154, as disclosed in GB 1,372,034. See also lipases in Japanese Patent Application 53,20487, laid open Feb. 24, 1978. This lipase is available from Amano Pharmaceutical Co. Ltd., Nagoya, Japan, under the trade name Lipase P "Amano," or "Amano-P." Other suitable commercial lipases include Amano-CES, lipases ex *Chromobacter viscosum*, e.g. *Chromobacter viscosum* var. *lipolyticum* NRRLB 3673 from Toyo Jozo Co., Tagata, Japan; *Chromobacter viscosum* lipases from U.S. Biochemical Corp., U.S.A. and Disoynth Co., The Netherlands, and lipases ex Pseudomonas gladioli. LIPOLASE® enzyme derived from Humicola lanuginosa and commercially available from Novo, see also EP 341,947, is a preferred lipase for use herein. Lipase and amylase variants stabilized against peroxidase enzymes are described in WO 9414951 A to Novo. See also WO 9205249 and RD 94359044.

In spite of the large number of publications on lipase enzymes, only the lipase derived from *Humicola lanuginosa* and produced in *Aspergillus oryzae* as host has so far found widespread application as additive for fabric washing products. It is available from Novo Nordisk under the tradename Lipolase™, as noted above. In order to optimize the stain removal performance of Lipolase, Novo Nordisk have made a number of variants. As described in WO 92/05249, the D96L variant of the native *Humicola lanuginosa* lipase improves the lard stain removal efficiency by a factor 4.4 over the wild-type lipase (enzymes compared in an amount ranging from 0.075 to 2.5 mg protein per liter). Research Disclosure No. 35944 published on Mar. 10, 1994, by Novo Nordisk discloses that the lipase variant (D96L) may be added in an amount corresponding to 0.001–100-mg (5–500,000 LU/liter) lipase variant per liter of wash liquor. The present invention provides the benefit of improved whiteness maintenance on fabrics using low levels of D96L variant in detergent compositions containing the mid-chain branched primary alkyl polyoxyalkylene surfactants in the manner disclosed herein, especially when the D96L is used at levels in the range of about 50 LU to about 8500 LU per liter of wash solution.

Cutinase enzymes suitable for use herein are described in WO 8809367 A to Genencor.

Peroxidase enzymes may be used in combination with oxygen sources, e.g., percarbonate, perborate, hydrogen peroxide, etc., for "solution bleaching" or prevention of transfer of dyes or pigments removed from substrates during the wash to other substrates present in the wash solution. Known peroxidases include horseradish peroxidase, ligninase, and haloperoxidases such as chloro- or bromo-peroxidase. Peroxidase-containing detergent compositions are disclosed in WO 89099813 A, Oct. 19, 1989 to Novo and WO 8909813 A to Novo.

A range of enzyme materials and means for their incorporation into synthetic detergent compositions is also disclosed in WO 9307263 A and WO 9307260 A to Genencor International, WO 8908694 A to Novo, and U.S. Pat. No. 3,553,139, Jan. 5, 1971 to McCarty et al. Enzymes are further disclosed in U.S. Pat. No. 4,101,457, Place et al, Jul. 18, 1978, and in U.S. Pat. No. 4,507,219, Hughes, Mar. 26, 1985. Enzyme materials useful for liquid detergent formulations, and their incorporation into such formulations, are disclosed in U.S. Pat. No. 4,261,868, Hora et al, Apr. 14, 1981. Enzymes for use in detergents can be stabilised by various techniques. Enzyme stabilisation techniques are disclosed and exemplified in U.S. Pat. No. 3,600,319, Aug. 17, 1971, Gedge et al, EP 199,405 and EP 200,586, Oct. 29, 1986, Venegas. Enzyme stabilisation systems are also described, for example, in U.S. Pat. No. 3,519,570. A useful Bacillus, sp. AC13 giving proteases, xylanases and cellulases, is described in WO 9401532 A to Novo.

Enzyme Stabilizing System—The enzyme-containing compositions herein may optionally also comprise from about 0.001% to about 10%, preferably from about 0.005% to about 8%, most preferably from about 0.01% to about 6%, by weight of an enzyme stabilizing system. The enzyme stabilizing system can be any stabilizing system which is compatible with the detersive enzyme. Such a system may be inherently provided by other formulation actives, or be added separately, e.g., by the formulator or by a manufacturer of detergent-ready enzymes. Such stabilizing systems can, for example, comprise calcium ion, boric acid, propylene glycol, short chain carboxylic acids, boronic acids, and mixtures thereof, and are designed to address different stabilization problems depending on the type and physical form of the detergent composition.

One stabilizing approach is the use of water-soluble sources of calcium and/or magnesium ions in the finished compositions which provide such ions to the enzymes. Calcium ions are generally more effective than magnesium ions and are preferred herein if only one type of cation is being used. Typical detergent compositions, especially liquids, will comprise from about 1 to about 30, preferably from about 2 to about 20, more preferably from about 8 to about 12 millimoles of calcium ion per liter of finished detergent composition, though variation is possible depending on factors including the multiplicity, type and levels of enzymes incorporated. Preferably water-soluble calcium or magnesium salts are employed, including for example calcium chloride, calcium hydroxide, calcium formate, calcium malate, calcium maleate, calcium hydroxide and calcium acetate; more generally, calcium sulfate or magnesium salts corresponding to the exemplified calcium salts may be used. Further increased levels of Calcium and/or Magnesium may of course be useful, for example for promoting the greasecutting action of certain types of surfactant.

Another stabilizing approach is by use of borate species. See Severson, U.S. Pat. No. 4,537,706. Borate stabilizers, when used, may be at levels of up to 10% or more of the composition though more typically, levels of up to about 3% by weight of boric acid or other borate compounds such as borax or orthoborate are suitable for liquid detergent use. Substituted boric acids such as phenylboronic acid, butaneboronic acid, p-bromophenylboronic acid or the like can be used in place of boric acid and reduced levels of total boron in detergent compositions may be possible though the use of such substituted boron derivatives.

Stabilizing systems of certain cleaning compositions, for example automatic dishwashing compositions, may further comprise from 0 to about 10%, preferably from about 0.01% to about 6% by weight, of chlorine bleach scavengers, added to prevent chlorine bleach species present in many water supplies from attacking and inactivating the enzymes, especially under alkaline conditions. While chlorine levels in water may be small, typically in the range from about 0.5 ppm to about 1.75 ppm, the available chlorine in the total volume of water that comes in contact with the enzyme, for example during dish- or fabric-washing, can be relatively large; accordingly, enzyme stability to chlorine in-use is sometimes problematic. Since perborate or percarbonate, which have the ability to react with chlorine bleach, may present in certain of the instant compositions in amounts accounted for separately from the stabilizing system, the use of additional stabilizers against chlorine, may, most generally, not be essential, though improved results may be obtainable from their use. Suitable chlorine scavenger anions are widely known and readily available, and, if used, can be salts containing ammonium cations with sulfite, bisulfite, thiosulfite, thiosulfate, iodide, etc. Antioxidants such as carbamate, ascorbate, etc., organic amines such as ethylenediaminetetracetic acid (EDTA) or alkali metal salt thereof, monoethanolamine (MEA), and mixtures thereof can likewise be used. Likewise, special enzyme inhibition systems can be incorporated such that different enzymes have maximum compatibility. Other conventional scavengers such as bisulfate, nitrate, chloride, sources of hydrogen peroxide such as sodium perborate tetrahydrate, sodium perborate monohydrate and sodium percarbonate, as well as phosphate, condensed phosphate, acetate, benzoate, citrate, formate, lactate, malate, tartrate, salicylate, etc., and mixtures thereof can be used if desired. In general, since the chlorine scavenger function can be performed by ingredients separately listed under better recognized functions, (e.g., hydrogen peroxide sources), there is no absolute requirement to add a separate chlorine scavenger unless a compound performing that function to the desired extent is absent from an enzyme-containing embodiment of the invention; even then, the scavenger is added only for optimum results. Moreover, the formulator will exercise a chemist's normal skill in avoiding the use of any enzyme scavenger or stabilizer which is majorly incompatible, as formulated, with other reactive ingredients. In relation to the use of ammonium salts, such salts can be simply admixed with the detergent composition but are prone to adsorb water and/or liberate ammonia during storage. Accordingly, such materials, if present, are desirably protected in a particle such as that described in U.S. Pat. No. 4,652,392, Baginski et al.

Builders—Detergent builders selected from aluminosilicates and silicates are preferably included in the compositions herein, for example to assist in controlling mineral, especially Ca and/or Mg, hardness in wash water or to assist in the removal of particulate soils from surfaces.

Suitable silicate builders include water-soluble and hydrous solid types and including those having chain-, layer-, or three-dimensional- structure as well as amorphous-solid or non-structured-liquid types. Preferred are alkali metal silicates, particularly those liquids and solids having a $SiO_2:Na_2O$ ratio in the range 1.6:1 to 3.2:1, including, particularly for automatic dishwashing purposes, solid hydrous 2-ratio silicates marketed by PQ Corp. under the tradename BRITESIL®, e.g., BRITESIL H2O; and layered silicates, e.g., those described in U.S. Pat. No. 4,664,839, May 12, 1987, H. P. Rieck. NaSKS-6, sometimes abbreviated "SKS-6", is a crystalline layered aluminium-free $\delta$-$Na_2SiO_5$ morphology silicate marketed by Hoechst and is preferred especially in granular laundry compositions. See preparative methods in German DE-A-3,417,649 and DE-A-3,742,043. Other layered silicates, such as those having the general formula $NaMSi_xO_{2x+1} \cdot yH_2O$ wherein M is sodium or hydrogen, x is a number from 1.9 to 4, preferably 2, and y is a number from 0 to 20, preferably 0, can also or alternately be used herein. Layered silicates from Hoechst also include NaSKS-5, NaSKS-7 and NaSKS-11, as the $\alpha$, $\beta$ and $\gamma$ layer-silicate forms. Other silicates may also be useful, such as magnesium silicate, which can serve as a crispening agent in granules, as a stabilising agent for bleaches, and as a component of suds control systems.

Also suitable for use herein are synthesized crystalline ion exchange materials or hydrates thereof having chain structure and a composition represented by the following general formula in an anhydride form: $xM_2O \cdot ySiO_2 \cdot zM'O$ wherein M is Na and/or K, M' is Ca and/or Mg; y/x is 0.5 to 2.0 and z/x is 0.005 to 1.0 as taught in U.S. Pat. No. 5,427,711, Sakaguchi et al, Jun. 27, 1995.

Aluminosilicate builders are especially useful in granular detergents, but can also be incorporated in liquids, pastes or gels. Suitable for the present purposes are those having empirical formula: $[M_z(AlO_2)_z(SiO_2)_y].xH_2O$ wherein z and v are integers of at least 6, the molar ratio of z to v is in the range from 1.0 to 0.5, and x is an integer from 15 to 264. Aluminosilicates can be crystalline or amorphous, naturally-occurring or synthetically derived. An aluminosilicate production method is in U.S. Pat. No. 3,985,669, Krummel, et al, Oct. 12, 1976. Preferred synthetic crystalline aluminosilicate ion exchange materials are available as Zeolite A, Zeolite P (B), Zeolite X and, to whatever extent this differs from Zeolite P, the so-called Zeolite MAP. Natural types, including clinoptilolite, may be used. Zeolite A has the formula: $Na_{12}[(AlO_2)_{12}(SiO_2)_{12}].xH_2O$ wherein x is from 20 to 30, especially 27. Dehydrated zeolites (x=0–10) may also be used. Preferably, the aluminosilicate has a particle size of 0.1 –10 microns in diameter.

Detergent builders in place of or in addition to the silicates and aluminosilicates described hereinbefore can optionally be included in the compositions herein, for example to assist in controlling mineral, especially Ca and/or Mg, hardness in wash water or to assist in the removal of particulate soils from surfaces. Builders can operate via a variety of mechanisms including forming soluble or insoluble complexes with hardness ions, by ion exchange, and by offering a surface more favorable to the precipitation of hardness ions than are the surfaces of articles to be cleaned. Builder level can vary widely depending upon end use and physical form of the composition. Built detergents typically comprise at least about 1% builder. Liquid formulations typically comprise about 5% to about 50%, more typically 5% to 35% of builder. Granular formulations typically comprise from about 10% to about 80%, more typically 15% to 50% builder by weight of the detergent composition. Lower or higher levels of builders are not excluded. For example, certain detergent additive or high-surfactant formulations can be unbuilt.

Suitable builders herein can be selected from the group consisting of phosphates and polyphosphates, especially the sodium salts; carbonates, bicarbonates, sesquicarbonates and carbonate minerals other than sodium carbonate or sesquicarbonate; organic mono-, di-, tri-, and tetracarboxylates especially water-soluble nonsurfactant carboxylates in acid, sodium, potassium or alkanolammonium salt form, as well as oligomeric or water-soluble low molecular weight polymer carboxylates including aliphatic and aromatic types; and phytic acid. These may be complemented by borates, e.g., for pH-buffering purposes, or by sulfates, especially sodium sulfate and any other fillers or carriers which may be important to the engineering of stable surfactant and/or builder-containing detergent compositions.

Builder mixtures, sometimes termed "builder systems" can be used and typically comprise two or more conventional builders, optionally complemented by chelants, pH-buffers or fillers, though these latter materials are generally accounted for separately when describing quantities of materials herein. In terms of relative quantities of surfactant and builder in the present detergents, preferred builder systems are typically formulated at a weight ratio of surfactant to builder of from about 60:1 to about 1:80. Certain preferred laundry detergents have said ratio in the range 0.90:1.0 to 4.0:1.0, more preferably from 0.95:1.0 to 3.0:1.0.

P-containing detergent builders often preferred where permitted by legislation include, but are not limited to, the alkali metal, ammonium and alkanolammonium salts of polyphosphates exemplified by the tripolyphosphates, pyrophosphates, glassy polymeric meta-phosphates; and phosphonates.

Suitable carbonate builders include alkaline earth and alkali metal carbonates as disclosed in German Patent Application No. 2,321,001 published on Nov. 15, 1973, although sodium bicarbonate, sodium carbonate, sodium sesquicarbonate, and other carbonate minerals such as trona or any convenient multiple salts of sodium carbonate and calcium carbonate such as those having the composition $2Na_2CO_3.CaCO_3$ when anhydrous, and even calcium carbonates including calcite, aragonite and vaterite, especially forms having high surface areas relative to compact calcite may be useful, for example as seeds or for use in synthetic detergent bars.

Suitable organic detergent builders include polycarboxylate compounds, including water-soluble nonsurfactant dicarboxylates and tricarboxylates. More typically builder polycarboxylates have a plurality of carboxylate groups, preferably at least 3 carboxylates. Carboxylate builders can be formulated in acid, partially neutral, neutral or overbased form. When in salt form, alkali metals, such as sodium, potassium, and lithium, or alkanolammonium salts are preferred. Polycarboxylate builders include the ether polycarboxylates, such as oxydisuccinate, see Berg, U.S. Pat. No. 3,128,287, Apr. 7, 1964, and Lamberti et al, U.S. Pat. No. 3,635,830, Jan. 18, 1972; "TMS/TDS" builders of U.S. Pat. No. 4,663,071, Bush et al, May 5, 1987; and other ether carboxylates including cyclic and alicyclic compounds, such as those described in U.S. Pat. Nos. 3,923,679; 3,835,163; 4,158,635; 4,120,874 and 4,102,903.

Other suitable builders are the ether hydroxypolycarboxylates, copolymers of maleic anhydride with ethylene or vinyl methyl ether; 1,3,5-trihydroxy benzene-2, 4,6-trisulphonic acid; carboxymethyloxysuccinic acid; the various alkali metal, ammonium and substituted ammonium salts of polyacetic acids such as ethylenediamine tetraacetic acid and nitrilotriacetic acid; as well as mellitic acid, succinic acid, polymaleic acid, benzene 1,3, 5-tricarboxylic acid, carboxy-methyloxysuccinic acid, and soluble salts thereof.

Citrates, e.g., citric acid and soluble salts thereof are important carboxylate builders e.g., for heavy duty liquid detergents, due to availability from renewable resources and biodegradability. Citrates can also be used in granular compositions, especially in combination with zeolite and/or layered silicates. Oxydisuccinates are also especially useful in such compositions and combinations.

Where permitted, and especially in the formulation of bars used for hand-laundering operations, alkali metal phosphates such as sodium tripolyphosphates, sodium pyrophosphate and sodium orthophosphate can be used. Phosphonate builders such as ethane-1-hydroxy-1,1-diphosphonate and other known phosphonates, e.g., those of U.S. Pat. Nos. 3,159,581; 3,213,030; 3,422,021; 3,400,148 and 3,422,137 can also be used and may have desirable antiscaling properties.

Certain detersive surfactants or their short-chain homologs also have a builder action. For unambiguous formula accounting purposes, when they have surfactant capability, these materials are summed up as detersive surfactants. Preferred types for builder functionality are illustrated by: 3,3-dicarboxy-4-oxa-1,6-hexanedioates and the related compounds disclosed in U.S. Pat. No. 4,566,984, Bush, Jan. 28, 1986. Succinic acid builders include the $C_5$–$C_{20}$ alkyl and alkenyl succinic acids and salts thereof.

Succinate builders also include: laurylsuccinate, myristylsuccinate, palmitylsuccinate, 2-dodecenylsuccinate (preferred), 2-pentadecenylsuccinate, and the like. Laurylsuccinates are described in European Patent Application 86200690.5/0,200,263, published Nov. 5, 1986. Fatty acids, e.g., $C_{12}$–$C_{18}$ monocarboxylic acids, can also be incorporated into the compositions as surfactant/builder materials alone or in combination with the aforementioned builders, especially citrate and/or the succinate builders, to provide additional builder activity. Other suitable polycarboxylates are disclosed in U.S. Pat. No. 4,144,226, Crutchfield et al, Mar. 13, 1979 and in U.S. Pat. No. 3,308,067, Diehl, Mar. 7, 1967. See also Diehl, U.S. Pat. No. 3,723,322.

Other types of inorganic builder materials which can be used have the formula $(M_x)_i\ Ca_y(CO_3)_z$ wherein x and i are integers from 1 to 15, y is an integer from 1 to 10, z is an integer from 2 to 25, $M_i$ are cations, at least one of which is a water-soluble, and the equation $\Sigma_i = 1-15(x_i$ multiplied by the valence of $M_i) + 2y = 2z$ is satisfied such that the formula has a neutral or "balanced" charge. These builders are referred to herein as "Mineral Builders". Waters of hydration or anions other than carbonate may be added provided that the overall charge is balanced or neutral. The charge or valence effects of such anions should be added to the right side of the above equation. Preferably, there is present a water-soluble cation selected from the group consisting of hydrogen, water-soluble metals, hydrogen, boron, ammonium, silicon, and mixtures thereof, more preferably, sodium, potassium, hydrogen, lithium, ammonium and mixtures thereof, sodium and potassium being highly preferred. Nonlimiting examples of noncarbonate anions include those selected from the group consisting of chloride, sulfate, fluoride, oxygen, hydroxide, silicon dioxide, chromate, nitrate, borate and mixtures thereof. Preferred builders of this type in their simplest forms are selected from the group consisting of $Na_2Ca(CO_3)_2$, $K_2Ca(CO_3)_2$, $Na_2Ca_2(CO_3)_3$, $NaKCa(CO_3)_2$, $NaKCa_2(CO_3)_3$, $K_2Ca_2(CO_3)_3$, and combinations thereof. An especially preferred material for the builder described herein is $Na_2Ca(CO_3)_2$ in any of its crystalline modifications. Suitable builders of the above-defined type are further illustrated by, and include, the natural or synthetic forms of any one or combinations of the following minerals: Afghanite, Andersonite, AshcroftineY, Beyerite, Borcarite, Burbankite, Butschliite, Cancrinite, Carbocernaite, Carletonite, Davyne, DonnayiteY, Fairchildite, Ferrisurite, Franzinite, Gaudefroyite, Gaylussite, Girvasite, Gregoryite, Jouravskite, KamphaugiteY, Kettnerite, Khanneshite, LepersonniteGd, Liottite, MckelveyiteY, Microsommite, Mroseite, Natrofairchildite, Nyerereite, RemonditeCe, Sacrofanite, Schrockingerite, Shortite, Surite, Tunisite, Tuscanite, Tyrolite, Vishnevite, and Zemkorite. Preferred mineral forms include Nyererite, Fairchildite and Shortite.

Detersive Surfactants:

The detergent compositions according to the present invention preferably further comprise additional surfactants, herein also referred to as co-surfactants. It is to be understood that the branched-chain surfactants prepared in the manner of the present invention may be used singly in cleaning compositions or in combination with other detersive surfactants. Typically, fully-formulated cleaning compositions will contain a mixture of surfactant types in order to obtain broad-scale cleaning performance over a variety of soils and stains and under a variety of usage conditions. One advantage of the branched-chain surfactants herein is their ability to be readily formulated in combination with other known surfactant types. Nonlimiting examples of additional surfactants which may be used herein typically at levels from about 1% to about 55%, by weight, include the unsaturated sulfates such as oleyl sulfate, the $C_{10}$–$C_{18}$ alkyl alkoxy sulfates ("$AE_xS$"; especially EO 1–7 ethoxy sulfates), $C_{10}$–$C_{18}$ alkyl alkoxy carboxylates (especially the EO 1–5 ethoxycarboxylates), the $C_{10-18}$ glycerol ether sulfates, the $C_{10}$–$C_{18}$ alkyl polyglycosides and their corresponding sulfated polyglycosides, and $C_{12}$–$C_{18}$ alpha-sulfonated fatty acid esters. Nonionic surfactants such as the ethoxylated $C_{10}$–$C_{18}$ alcohols and alkyl phenols, (e.g., $C_{10}$–$C_{18}$ EO (1–10) can also be used. If desired, other conventional surfactants such as the $C_{12}$–$C_{18}$ betaines and sulfobetaines ("sultaines"), $C_{10}$–$C_{18}$ amine oxides, and the like, can also be included in the overall compositions. The $C_{10}$–$C_{18}$ N-alkyl polyhydroxy fatty acid amides can also be used. Typical examples include the $C_{12}$–$C_{18}$ N-methylglucamides. See WO 9,206,154. Other sugar-derived surfactants include the N-alkoxy polyhydroxy fatty acid amides, such as $C_{10}$–$C_{18}$ N-(3-methoxypropyl) glucamide. The N-propyl through N-hexyl $C_{12}$–$C_{18}$ glucamides can be used for low sudsing. $C_{10}$–$C_{20}$ conventional soaps may also be used. If high sudsing is desired, the branched-chain $C_{10}$–$C_{16}$ soaps may be used. $C_{10}$–$C_{14}$ alkyl benzene sulfonates (LAS), which are often used in laundry detergent compositions, can also be used with the branched surfactants herein.

A wide range of these co-surfactants can be used in the detergent compositions of the present invention. A typical listing of anionic, nonionic, ampholytic and zwitterionic classes, and species of these co-surfactants, is given in U.S. Pat. No. 3,664,961 issued to Norris on May 23, 1972. Amphoteric surfactants are also described in detail in "Amphoteric Surfactants, Second Edition", E. G. Lomax, Editor (published 1996, by Marcel Dekker, Inc.)

The laundry detergent compositions of the present invention typically comprise from about 0.1% to about 35%, preferably from about 0.5% to about 15%, by weight of co-surfactants. Selected co-surfactants are further identified as follows.

(1) Anionic Co-surfactants:

Nonlimiting examples of anionic co-surfactants useful herein, typically at levels. from about 0.1% to about 50%, by weight, include the conventional $C_{11}$–$C_{18}$ alkyl benzene sulfonates ("LAS") and primary, branched-chain and random $C_{10}$–$C_{20}$ alkyl sulfates ("AS"), the $C_{10}$–$C_{18}$ secondary (2,3) alkyl sulfates of the formula $CH_3(CH_2)_x(CHOSO_3^-M^+)CH_3$ and $CH_3(CH_2)_y(CHOSO_3^-M^+)CH_2CH_3$ where x and (y+1) are integers of at least about 7, preferably at least about 9, and M is a water-solubilizing cation, especially sodium, unsaturated sulfates such as oleyl sulfate, the $C_{10}$–$C_{18}$ alpha-sulfonated fatty acid esters, the $C_{10}$–$C_{18}$ sulfated alkyl polyglycosides, the $C_{10}$–$C_{18}$ alkyl alkoxy sulfates ("AEXS"; especially EO 1–7 ethoxy sulfates), and $C_{10}$–$C_{18}$ alkyl alkoxy carboxylates (especially the EO 1–5 ethoxycarboxylates). The $C_{12}$–$C_{18}$ betaines and sulfobetaines ("sultaines"), $C_{10}$–$C_{18}$ amine oxides, and the like, can also be included in the overall compositions. $C_{10}$–$C_{20}$ conventional soaps may also be used. If high sudsing is desired, the branched-chain $C_{10}$–$C_{16}$ soaps may be used. Other conventional useful anionic co-surfactants are listed in standard texts.

The alkyl alkoxy sulfate surfactants useful herein are preferably water soluble salts or acids of the formula $RO(A)_mSO_3M$ wherein R is an unsubstituted $C_{10}$–$C_{24}$ alkyl or hydroxyalkyl group having a $C_{10}$–$C_{24}$ alkyl component, preferably a $C_{12}$–$C_{18}$ alkyl or hydroxyalkyl, more preferably $C_{12}$–$C_{15}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include ethanol-, triethanol-, methyl-, dimethyl-, trimethyl-ammonium cations and quaternary ammonium cations such as tetramethyl-ammonium and dimethyl piperidinium cations and those derived from alkylamines such as ethylamine, diethylamine, triethylamine, mixtures thereof, and the like. Exemplary surfactants are $C_{12}$–$C_{15}$ alkyl polyethoxylate (1.0) sulfate ($C_{12}$–$C_{15}$E(1.0)M), $C_{12}$–$C_{15}$ alkyl polyethoxylate (2.25) sulfate ($C_{12}$–$C_{15}$E(2.25)M), $C_{12}$–$C_{15}$ alkyl polyethoxylate (3.0) sulfate ($C_{12}$–$C_{15}$E(3.0)M), and $C_{12}$–$C_{15}$ alkyl polyethoxylate (4.0) sulfate ($C_{12}$–$C_{15}$E(4.0)M), wherein M is conveniently selected from sodium and potassium.

The alkyl sulfate surfactants useful herein are preferably water soluble salts or acids of the formula $ROSO_3M$ wherein R preferably is a $C_{11}$–$C_{24}$ hydrocarbyl, preferably an alkyl or hydroxyalkyl having a $C_{10}$–$C_{18}$ alkyl component, more preferably a $C_{12}$–$C_{15}$ alkyl or hydroxyalkyl, and M is H or a cation, e.g., an alkali metal cation (e.g. sodium, potassium, lithium), or ammonium or substituted ammonium (e.g. methyl-, dimethyl-, and trimethyl ammonium cations and quaternary ammonium cations such as tetramethyl-ammonium and dimethyl piperidinium cations and quaternary ammonium cations derived from alkylamines such as ethylamine, diethylamine, triethylamine, and mixtures thereof, and the like).

Other suitable anionic surfactants that can be used are alkyl ester sulfonate surfactants including linear esters of $C_8$–$C_{20}$ carboxylic acids (i.e., fatty acids) which are sulfonated with gaseous $SO_3$ according to "The Journal of the American Oil Chemists Society", 52 (1975), pp. 323–329. Suitable starting materials would include natural fatty substances as derived from tallow, palm oil, etc.

The preferred alkyl ester sulfonate surfactant, especially for laundry applications, comprise alkyl ester sulfonate surfactants of the structural formula $R^3$—CH($SO_3M$)—C(O)—$OR^4$ wherein $R^3$ is a $C_8$–$C_{20}$ hydrocarbyl, preferably an alkyl, or combination thereof, $R^4$ is a $C_1$–$C_6$ hydrocarbyl, preferably an alkyl, or combination thereof, and M is a cation which forms a water soluble salt with the alkyl ester sulfonate. Suitable salt-forming cations include metals such as sodium, potassium, and lithium, and substituted or unsubstituted ammonium cations, such as monoethanolamine, diethanolamine, and triethanolamine. Preferably, $R^3$ is $C_{10}$–$C_{16}$ alkyl, and $R^4$ is methyl, ethyl or isopropyl. Especially preferred are the methyl ester sulfonates wherein $R^3$ is $C_{10}$–$C_{16}$ alkyl.

Other anionic co-surfactants useful for detersive purposes can also be included in the laundry detergent compositions of the present invention. These can include salts (including, for example, sodium, potassium, ammonium, and substituted ammonium salts such as mono-, di- and triethanolamine salts) of soap, $C_8$–$C_{22}$ primary or secondary alkanesulfonates, $C_8$–$C_{24}$ olefinsulfonates, sulfonated polycarboxylic acids prepared by sulfonation of the pyrolyzed product of alkaline earth metal citrates, e.g., as described in British patent specification No. 1,082,179, $C_8$–$C_{24}$ alkylpolyglycolethersulfates (containing up to 10 moles of ethylene oxide); alkyl glycerol sulfonates, fatty acyl glycerol sulfonates, fatty oleoyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinates (especially saturated and unsaturated $C_{12}$–$C_{18}$ monoesters) and diesters of sulfosuccinates (especially saturated and unsaturated $C_6$–$C_{12}$ diesters), sulfates of alkylpolysaccharides such as the sulfates of alkylpolyglucoside (the nonionic nonsulfated compounds being described below), and alkyl polyethoxy carboxylates such as those of the formula $RO(CH_2CH_2O)_k$—$CH_2COO$—M+ wherein R is a $C_8$–$C_{22}$ alkyl, k is an integer from 0 to 10, and M is a soluble salt-forming cation. Resin acids and hydrogenated resin acids are also suitable, such as rosin, hydrogenated rosin, and resin acids and hydrogenated resin acids present in or derived from tall oil. Further examples are described in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23 (herein incorporated by reference).

A preferred disulfate surfactant has the formula

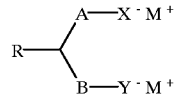

where R is an alkyl, substituted alkyl, alkenyl, aryl, alkaryl, ether, ester, amine or amide group of chain length $C_1$ to $C_{28}$, preferably $C_3$ to $C_{24}$, most preferably $C_8$ to $C_{20}$, or hydrogen; A and B are independently selected from alkyl, substituted alkyl, and alkenyl groups of chain length $C_1$ to $C_{28}$, preferably $C_1$ to $C_5$, most preferably $C_1$ or $C_2$, or a covalent bond, and A and B in total contain at least 2 atoms; A, B, and R in total contain from 4 to about 31 carbon atoms; X and Y are anionic groups selected from the group consisting of sulfate and sulfonate, provided that at least one of X or Y is a sulfate group; and M is a cationic moiety, preferably a substituted or unsubstituted ammonium ion, or an alkali or alkaline earth metal ion.

The most preferred disulfate surfactant has the formula as above where R is an alkyl group of chain length from $C_{10}$ to $C_{18}$, A and B are independently $C_1$ or $C_2$, both X and Y are sulfate groups, and M is a potassium, ammonium, or a sodium ion.

The disulfate surfactant is typically present at levels of incorporation of from about 0.1% to about 50%, preferably from about 0.1% to about 35%, most preferably from about 0.5% to about 15% by weight of the detergent composition.

Preferred disulfate surfactant herein include:
(a) 1,3 disulfate compounds, preferably 1,3 C7–C23 (i.e., the total number of carbons in the molecule) straight or branched chain alkyl or alkenyl disulfates, more preferably having the formula:

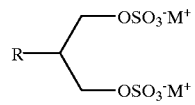

wherein R is a straight or branched chain alkyl or alkenyl group of chain length from about $C_4$ to about $C_{18}$;
(b) 1,4 disulfate compounds, preferably 1,4 C8–$C_{22}$ straight or branched chain alkyl or alkenyl disulfates, more preferably having the formula:

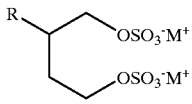

wherein R is a straight or branched chain alkyl or alkenyl group of chain length from about $C_4$ to about $C_{18}$; preferred R are selected from octanyl, nonanyl, decyl, dodecyl, tetradecyl, hexadecyl, octadecyl, and mixtures thereof, and
(c) 1,5 disulfate compounds, preferably 1,5 C9–C23 straight or branched chain alkyl or alkenyl disulfates, more preferably having the formula:

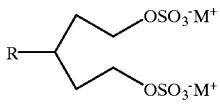

wherein R is a straight or branched chain alkyl or alkenyl group of chain length from about $C_4$ to about $C_{18}$.

Known syntheses of certain disulfated surfactants, in general, use an alkyl or alkenyl succinic anhydride as the principal starting material. This is initially subjected to a reduction step from which a diol is obtained. Subsequently the diol is subjected to a sulfation step to give the disulfated product. As an example, U.S. Pat. No. 3,634,269 describes 2-alkyl or alkenyl-1,4-butanediol disulfates prepared by the reduction of alkenyl succinic anhydrides with lithium aluminium hydride to produce either alkenyl or alkyl diols which are then sulfated. In addition, U.S. Pat. No. 3,959,334 and U.S. Pat. No. 4,000,081 describe 2-hydrocarbyl-1,4-butanediol disulfates also prepared using a method involving the reduction of alkenyl succinic anhydrides with lithium aluminium hydride to produce either alkenyl or alkyl diols which are then sulfated.

See also U.S. Pat. No. 3,832,408 and U.S. Pat. No. 3,860,625 which describe 2-alkyl or alkenyl-b 1,4-butanediol ethoxyl ate disulfates prepared by the reduction of alkenyl succinic anhydrides with lithium aluminium hydride to produce either alkenyl or alkyl diols which are then ethoxylated prior to sulfation.

These compounds may also be made by a method involving synthesis of the disulfate surfactant from a substituted cyclic anhydride having one or more carbon chain substituents having in total at least 5 carbon atoms comprising the following steps:
(i) reduction of said substituted cyclic anhydride to form a diol; and
(ii) sulfation of said diol to form a disulfate wherein said reduction step comprises hydrogenation under pressure in the presence of a transition metal-containing hydrogenation catalyst.

When included therein, the laundry detergent compositions of the present invention typically comprise from about 0.1% to about 50%, preferably from about 1% to about 40% by weight of an anionic surfactant.

(2) Nonionic Co-surfactants:

Nonlimiting examples of nonionic co-surfactants useful herein typically at levels from about 0.1% to about 50%, by weight include the alkoxylated alcohols 15 (AE's) and alkyl phenols, polyhydroxy fatty acid amides (PFAA's), alkyl polyglycosides (APG's), $C_{10}$–$C_{18}$ glycerol ethers, and the like.

More specifically, the condensation products of primary and secondary aliphatic alcohols with from about 1 to about 25 moles of ethylene oxide (AE) are suitable for use as the nonionic surfactant in the present invention. The alkyl chain of the aliphatic alcohol can either be straight or branched, primary or secondary, and generally contains from about 8 to about 22 carbon atoms. Preferred are the condensation products of alcohols having an alkyl group containing from about 8 to about 20 carbon atoms, more preferably from about 10 to about 18 carbon atoms, with from about 1 to about 10 moles, preferably 2 to 7, most preferably 2 to 5, of ethylene oxide per mole of alcohol. Especially preferred nonionic surfactants of this type are the $C_9$–$C_{15}$ primary alcohol ethoxylates containing 3–12 moles of ethylene oxide per mole of alcohol, particularly the $C_{12}$–$C_{15}$ primary alcohols containing 5–10 moles of ethylene oxide per mole of alcohol.

Examples of commercially available nonionic surfactants of this type include: Tergitol™ 15-S-9 (the condensation product of $C_{11}$–$C_{15}$ linear alcohol with 9 moles ethylene oxide) and Tergitol™ 24-L-6 NMW (the condensation product of $C_{12}$–$C_{14}$ primary alcohol with 6 moles ethylene oxide with a narrow molecular weight distribution), both marketed by Union Carbide Corporation; Neodol™ 45-9 (the condensation product of $C_{14}$–$C_{15}$ linear alcohol with 9 moles of ethylene oxide), Neodol™ 23-3 (the condensation product of $C_{12}$–$C_{13}$ linear alcohol with 3 moles of ethylene oxide), Neodol™ 45-7 (the condensation product of $C_{14}$–$C_{15}$ linear alcohol with 7 moles of ethylene oxide) and Neodol™ 45-5 (the condensation product of $C_{14}$–$C_{15}$ linear alcohol with 5 moles of ethylene oxide) marketed by Shell Chemical Company; Kyro™ EOB (the condensation product of $C_{13}$–$C_{15}$ alcohol with 9 moles ethylene oxide), marketed by The Procter & Gamble Company; and Genapol LA O3O or O5O (the condensation product of $C_{12}$–$C_{14}$ alcohol with 3 or 5 moles of ethylene oxide) marketed by Hoechst. The preferred range of HLB in these AE nonionic surfactants is from 8–17 and most preferred from 8–14. Condensates with propylene oxide and butylene oxides may also be used.

Another class of preferred nonionic co-surfactants for use herein are the polyhydroxy fatty acid amide surfactants of the formula.

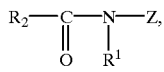

wherein $R^1$ is H, or $C_{1-4}$ hydrocarbyl, 2-hydroxy ethyl, 2-hydroxy propyl or a mixture thereof, $R^2$ is $C_{5-31}$ hydrocarbyl, and Z is a polyhydroxyhydrocarbyl having a linear hydrocarbyl chain with at least 3 hydroxyls directly connected to the chain, or an alkoxylated derivative thereof. Preferably, $R^1$ is methyl, $R^2$ is a straight $C_{11-15}$ alkyl or $C_{15-17}$ alkyl or alkenyl chain such as coconut alkyl or mixtures thereof, and Z is derived from a reducing sugar such as glucose, fructose, maltose, lactose, in a reductive amination reaction. Typical examples include the $C_{12}$–$C_{18}$ and $C_{12}$–$C_{14}$ N-methylglucamides. See U.S. Pat. No. 5,194, 639 and 5,298,636. N-alkoxy polyhydroxy fatty acid amides can also be used; see U.S. Pat. No. 5,489,393.

Also useful as a nonionic co-surfactant in the present invention are the alkylpolysaccharides such as those disclosed in U.S. Pat. No. 4,565,647, Llenado, issued Jan. 21, 1986, having a hydrophobic group containing from about 6 to about 30 carbon atoms, preferably from about 10 to about 16 carbon atoms, and a polysaccharide, e.g. a polyglycoside, hydrophilic group containing from about 1.3 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties (optionally the hydrophobic group is attached at the 2-, 3-, 4-, etc. positions thus giving a glucose or galactose as opposed to a glucoside or galactoside). The intersaccharide bonds can be, e.g., between the one position of the additional saccharide units and the 2-, 3-, 4-, and/or 6-positions on the preceding saccharide units.

Preferred alkylpolyglycosides have the formula $$R^2O(C_nH_{2n}O)_t(\text{glycosyl})_x$$

wherein $R^2$ is selected from the group consisting of alkyl, alkylphenyl, hydroxyalkyl, hydroxyalkylphenyl, and mixtures thereof in which the alkyl groups contain from about 10 to about 18, preferably from about 12 to about 14, carbon atoms; n is 2 or 3, preferably 2; t is from 0 to about 10, preferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominately the 2-position. Compounds of this type and their use in detergent are disclosed in EP-B 0 070 077, 0 075 996 and 0 094 118.

Polyethylene, polypropylene, and polybutylene oxide condensates of alkyl phenols are also suitable for use as the nonionic surfactant of the surfactant systems of the present invention, with the polyethylene oxide condensates being preferred.

These compounds include the condensation products of alkyl phenols having an alkyl group containing from about 6 to about 14 carbon atoms, preferably from about 8 to about 14 carbon atoms, in either a straight-chain or branched-chain configuration with the alkylene oxide. In a preferred embodiment, the ethylene oxide is present in an amount equal to from about 2 to about 25 moles, more preferably from about 3 to about 15 moles, of ethylene oxide per mole of alkyl phenol.

Commercially available nonionic surfactants of this type include Igepal™ CO-630, marketed by the GAF Corporation; and Triton™ X-45, X-114, X-100 and X-102, all marketed by the Rohm & Haas Company. These surfactants are commonly referred to as alkylphenol alkoxylates (e.g., alkyl phenol ethoxylates).

The condensation products of ethylene oxide with a hydrophobic base formed by the condensation of propylene oxide with propylene glycol are also suitable for use as the additional nonionic surfactant in the present invention. The hydrophobic portion of these compounds will preferably have a molecular weight of from about 1500 to about 1800 and will exhibit water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially-available Pluronic™ surfactants, marketed by BASF.

Also suitable for use as the nonionic surfactant of the nonionic surfactant system of the present invention, are the condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11,000. Examples of this type of nonionic surfactant include certain of the commercially available Tetronic™ compounds, marketed by BASF.

Also preferred nonionics are amine oxide surfactants. The compositions of the present invention may comprise amine oxide in accordance with the general formula I:

$$R^1(EO)_x(PO)_y(BO)_zN(O)(CH_2R')_2 \cdot qH_2O \qquad (I).$$

In general, it can be seen that the structure (I) provides one long-chain moiety $R^1(EO)_x(PO)_y(BO)_z$ and two short chain moieties, $CH_2R'$. R' is preferably selected from hydrogen, methyl and $—CH_2OH$. In general $R^1$ is a primary or branched hydrocarbyl moiety which can be saturated or unsaturated, preferably, $R^1$ is a primary alkyl moiety. When x+y+z=0, $R^1$ is a hydrocarbyl moiety having chainlength of from about 8 to about 18. When x+y+z is different from 0, $R^1$ may be somewhat longer, having a chainlength in the range $C_{12}$–$C_{24}$. The general formula also encompasses amine oxides wherein x+y+z =0, $R_1$=$C_8$–$C_{18}$, R'=H and q=0–2, preferably 2. These amine oxides are illustrated by $C_{12-14}$ alkyldimethyl amine oxide, hexadecyl dimethylamine oxide, octadecylamine oxide and their hydrates, especially the dihydrates as disclosed in U.S. Pat. Nos. 5,075,501 and 5,071,594, incorporated herein by reference.

The invention also encompasses amine oxides wherein x+y+z is different from zero, specifically x+y+z is from about 1 to about 10, $R^1$ is a primary alkyl group containing 8 to about 24 carbons, preferably from about 12 to about 16 carbon atoms; in these embodiments y+z is preferably 0 and x is preferably from about 1 to about 6, more preferably from about 2 to about 4; EO represents ethyleneoxy; PO represents propyleneoxy; and BO represents butyleneoxy. Such amine oxides can be prepared by conventional synthetic methods, e.g., by the reaction of alkylethoxysulfates with dimethylamine followed by oxidation of the ethoxylated amine with hydrogen peroxide.

Highly preferred amine oxides herein are solutions at ambient temperature. Amine oxides suitable for use herein are made commercially by a number of suppliers, including Akzo Chemie, Ethyl Corp., and Procter & Gamble. See McCutcheon's compilation and Kirk-Othmer review article for alternate amine oxide manufacturers.

Whereas in certain of the preferred embodiments R' is H, there is some latitude with respect to having R' slightly larger than H. Specifically, the invention further encompasses embodiments wherein R' is $CH_2OH$, such as hexadecylbis(2-hydroxyethyl)amineoxide, tallowbis(2-hydroxyethyl)amine oxide, stearylbis(2-hydroxyethyl) amine oxide and oleylbis(2-hydroxyethyl)amine oxide, dodecyldimethylamine oxide dihydrate.

(3) Cationic Co-surfactants:

Nonlimiting examples of cationic co-surfactants useful herein typically at levels from about 0.1% to about 50%, by weight include the choline ester-type quats and alkoxylated quaternary ammonium (AQA) surfactant compounds, and the like.

Cationic co-surfactants useful as a component of the surfactant system is a cationic choline ester-type quat surfactant which are preferably water dispersible compounds having surfactant properties and comprise at least one ester (i.e. —COO—) linkage and at least one cationically charged group. Suitable cationic ester surfactants, including choline ester surfactants, have for example been disclosed in U.S. Pat. Nos. 4,228,042, 4,239,660 and 4,260,529.

Preferred cationic ester surfactants are those having the formula:

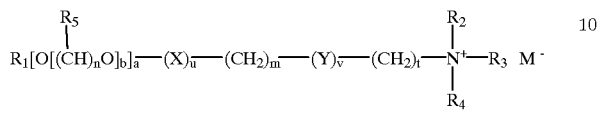

wherein $R_1$ is a $C_5$–$C_{31}$ linear or branched alkyl, alkenyl or alkaryl chain or $M^-.N^+(R_6R_7R_8)(CH_2)_s$; X and Y, independently, are selected from the group consisting of COO, OCO, O, CO, OCOO, CONH, NHCO, OCONH and NHCOO wherein at least one of X or Y is a COO, OCO, OCOO, OCONH or NHCOO group; $R_2$, $R_3$, $R_4$, $R_6$, $R_7$ and $R_8$ are independently selected from the group consisting of alkyl, alkenyl, hydroxyalkyl, hydroxyalkenyl and alkaryl groups having from 1 to 4 carbon atoms; and $R_5$ is independently H or a $C_1$–$C_3$ alkyl group; wherein the values of m, n, s and t independently lie in the range of from 0 to 8, the value of b lies in the range from 0 to 20, and the values of a, u and v independently are either 0 or 1 with the proviso that at least one of u or v must be 1; and wherein M is a counter anion.

Preferably $R_2$, $R_3$ and $R_4$ are independently selected from $CH_3$ and —$CH_2CH_2OH$.

Preferably M is selected from the group consisting of halide, methyl sulfate, sulfate, and nitrate, more preferably methyl sulfate, chloride, bromide or iodide.

Preferred water dispersible cationic ester surfactants are the choline esters having the formula:

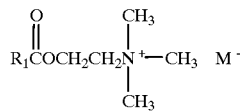

wherein $R_1$ is a $C_{11}$–$C_{19}$ linear or branched alkyl chain.

Particularly preferred choline esters of this type include the stearoyl choline ester quaternary methylammonium halides ($R^1=C_{17}$ alkyl), palmitoyl choline ester quaternary methylammonium halides ($R^1=C_{15}$ alkyl), myristoyl choline ester quaternary methylammonium halides ($R^1=C_{13}$ alkyl), lauroyl choline ester quaternary methylammonium halides ($R^1=C_{11}$ alkyl), cocoyl choline ester quaternary methylammonium halides ($R^1=C_{11}$–$C_{13}$ alkyl), tallowyl choline ester quaternary methylammonium halides ($R^1=C_{15}$–$C_{17}$ alkyl), and any mixtures thereof.

The particularly preferred choline esters, given above, may be prepared by the direct esterification of a fatty acid of the desired chain length with dimethylaminoethanol, in the presence of an acid catalyst. The reaction product is then quaternized with a methyl halide, preferably in the presence of a solvent such as ethanol, propylene glycol or preferably a fatty alcohol ethoxylate such as $C_{10}$–$C_{18}$ fatty alcohol ethoxylate having a degree of ethoxylation of from 3 to 50 ethoxy groups per mole forming the desired cationic material. They may also be prepared by the direct esterification of a long chain fatty acid of the desired chain length together with 2-haloethanol, in the presence of an acid catalyst material. The reaction product is then quaternized with trimethylamine, forming the desired cationic material.

Other suitable cationic ester surfactants have the structural formulas below, wherein d may be from 0 to 20.

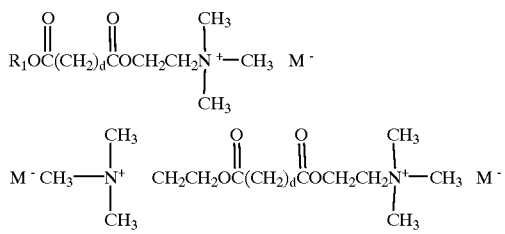

In a preferred aspect these cationic ester surfactant are hydrolysable under the conditions of a laundry wash method.

Cationic co-surfactants useful herein also include alkoxylated quaternary ammonium (AQA) surfactant compounds (referred to hereinafter as "AQA compounds") having the formula:

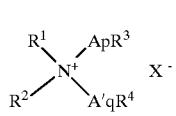

I wherein $R^1$ is a linear or branched alkyl or alkenyl moiety containing from about 8 to about 18 carbon atoms, preferably 10 to about 16 carbon atoms, most preferably from about 10 to about 14 carbon atoms; $R^2$ is an alkyl group containing from one to three carbon atoms, preferably methyl; $R^3$ and $R^4$ can vary independently and are selected from hydrogen (preferred), methyl and ethyl; $X^-$ is an anion such as chloride, bromide, methylsulfate, sulfate, or the like, sufficient to provide electrical neutrality. A and A' can vary independently and are each selected from $C_1$–$C_4$ alkoxy, especially ethoxy (i.e., —$CH_2CH_2O$—), propoxy, butoxy and mixed ethoxy/propoxy; p is from 0 to about 30, preferably 1 to about 4 and q is from 0 to about 30, preferably 1 to about 4, and most preferably to about 4; preferably both p and q are 1. See also: EP 2,084, published May 30, 1979, by The Procter & Gamble Company, which describes cationic co-surfactants of this type which are also useful herein.

AQA compounds wherein the hydrocarbyl substituent $R^1$ is $C_8$–$C_{11}$, especially $C_{10}$, enhance the rate of dissolution of laundry granules, especially under cold water conditions, as compared with the higher chain length materials. Accordingly, the $C_8$–$C_{11}$ AQA surfactants may be preferred by some formulators. The levels of the AQA surfactants used to prepare finished laundry detergent compositions can range from about 0.1% to about 5%, typically from about 0.45% to about 2.5%, by weight.

According to the foregoing, the following are nonlimiting, specific illustrations of AQA surfactants used herein. It is to be understood that the degree of alkoxylation noted herein for the AQA surfactants is reported as an average, following common practice for conventional ethoxylated nonionic surfactants. This is because the ethoxylation reactions typically yield mixtures of materials with differing degrees of ethoxylation. Thus, it is not uncommon to report total EO values other than as whole numbers, e.g., "EO2.5", "EO3.5", and the like.

| Designation | R$^1$ | R$^2$ | ApR$^3$ | A'qR$^4$ |
|---|---|---|---|---|
| AQA-1 (also referred to as Coco Methyl EO2) | C$_{12}$–C$_{14}$ | CH$_3$ | EO | EO |
| AQA-2 | C$_{12}$–C$_{16}$ | CH$_3$ | (EO)$_2$ | EO |
| AQA-3 (Coco Methyl EO4) | C$_{12}$–C$_{14}$ | CH$_3$ | (EO)$_2$ | (EO)$_2$ |
| AQA-4 | C$_{12}$ | CH$_3$ | EO | EO |
| AQA-5 | C$_{12}$–C$_{14}$ | CH$_3$ | (EO)$_2$ | (EO)$_3$ |
| AQA-6 | C$_{12}$–C$_{14}$ | CH$_3$ | (EO)$_2$ | (EO)$_3$ |
| AQA-7 | C$_8$–C$_{18}$ | CH$_3$ | (EO)$_3$ | (EO)$_2$ |
| AQA-8 | C$_{12}$–C$_{14}$ | CH$_3$ | (EO)$_4$ | (EO)$_4$ |
| AQA-9 | C$_{12}$–C$_{14}$ | C$_2$H$_5$ | (EO)$_3$ | (EO)$_3$ |
| AQA-10 | C$_{12}$–C$_{18}$ | C$_3$H$_7$ | (EO)$_3$ | (EO)$_4$ |
| AQA-11 | C$_{12}$–C$_{18}$ | CH$_3$ | (propoxy) | (EO)$_3$ |
| AQA-12 | C$_{10}$–C$_{18}$ | C$_2$H$_5$ | (iso-propoxy)$_2$ | (EO)$_3$ |
| AQA-13 | C$_{10}$–C$_{18}$ | CH$_3$ | (EO/PO)$_2$ | (EO)$_3$ |
| AQA-14 | C$_8$–C$_{18}$ | CH$_3$ | (EO)$_{15}$* | (EO)$_{15}$* |
| AQA-15 | C$_{10}$ | CH$_3$ | EO | EO |
| AQA-16 | C$_8$–C$_{12}$ | CH$_3$ | EO | EO |
| AQA-17 | C$_9$–C$_{11}$ | CH$_3$ | E0 3.5 Avg. | |
| AQA-18 | C$_{12}$ | CH$_3$ | E0 3.5 Avg. | |
| AQA-19 | C$_8$–C$_{14}$ | CH$_3$ | (EO)$_{10}$ | (EO)$_{10}$ |
| AQA-20 | C$_{10}$ | C$_2$H$_5$ | (EO)$_2$ | (EO)$_3$ |
| AQA-21 | C$_{12}$–C$_{14}$ | C$_2$H$_5$ | (EO)$_5$ | (EO)$_3$ |
| AQA-22 | C$_{12}$–C$_{18}$ | C$_3$H$_7$ | Bu | (EO)$_2$ |

*Ethoxy, optionally end-capped with methyl or ethyl.

The preferred bis-ethoxylated cationic surfactants herein are available under the trade name ETHOQUAD from Akzo Nobel Chemicals Company.

Highly preferred bis-AQA compounds for use herein are of the formula

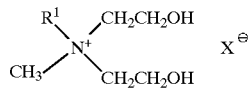

wherein R$^1$ is C$_{10}$–C$_{18}$ hydrocarbyl and mixtures thereof, preferably C$_{10}$, C$_{12}$, C$_{14}$ alkyl and mixtures thereof, and X is any convenient anion to provide charge balance, preferably chloride. With reference to the general AQA structure noted above, since in a preferred compound R$^1$ is derived from coconut (C$_{12}$–C$_{14}$ alkyl) fraction fatty acids, R$^2$ is methyl and ApR$^3$ and A'qR$^4$ are each monoethoxy, this preferred type of compound is referred to herein as "CocoMeEO2" or "AQA-1" in the above list.

Other preferred AQA compounds herein include compounds of the formula:

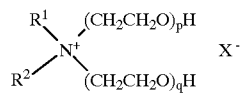

wherein RI is C$_{10}$–C$_{18}$ hydrocarbyl, preferably C$_{11}$–C$_{14}$ alkyl, independently p is 1 to about 3 and q is 1 to about 3, R$^2$ is C$_1$–C$_3$ alkyl, preferably methyl, and X is an anion, especially chloride.

Other compounds of the foregoing type include those wherein the ethoxy (CH$_2$CH$_2$O) units (EO) are replaced by butoxy (Bu), isopropoxy [CH(CH$_3$)CH$_2$O] and [CH$_2$CH(CH$_3$O] units (i-Pr) or n-propoxy units (Pr), or mixtures of EO and/or Pr and/or i-Pr units.

The following illustrates various other adjunct ingredients which may be used in the compositions of this invention, but is not intended to be limiting thereof. While the combination of the mid-chain branched primary alkyl polyoxyalkylene surfactants with such adjunct compositional ingredients can be provided as finished products in the form of liquids, gels, bars, or the like using conventional techniques, the manufacture of the granular laundry detergents herein requires some special processing techniques in order to achieve optimal performance. Accordingly, the manufacture of laundry granules will be described hereinafter separately in the Granules Manufacture section (below), for the convenience of the formulator.

Additional cationic co-surfactants are described, for example, in the "Surfactant Science Series, Volume 4, Cationic Surfactants" or in the "Industrial Surfactants Handbook". Classes of useful cationic surfactants described in these references include amide quats (i.e., Lexquat AMG & Schercoquat CAS), glycidyl ether quats (i.e., Cyostat 609), hydroxyalkyl quats (i.e., Dehyquart E), alkoxypropyl quats (i.e., Tomah Q-17-2), polypropoxy quats (Emcol CC-9), cyclic alkylammonium compounds (i.e., pyridinium or imidazolinium quats), and/or benzalkonium quats.

Polymeric Soil Release Agent—Known polymeric soil release agents, hereinafter "SRA" or "SRA's", can optionally be employed in the present detergent compositions. If utilized, SRA's will generally comprise from 0.01% to 10.0%, typically from 0.1% to 5%, preferably from 0.2% to 3.0% by weight, of the composition.

Preferred SRA's typically have hydrophilic segments to hydrophilize the surface of hydrophobic fibers such as polyester and nylon, and hydrophobic segments to deposit upon hydrophobic fibers and remain adhered thereto through completion of washing and rinsing cycles thereby serving as an anchor for the hydrophilic segments. This can enable stains occurring subsequent to treatment with SRA to be more easily cleaned in later washing procedures.

SRA's can include a variety of charged, e.g., anionic or even cationic (see U.S. Pat. No. 4,956,447), as well as noncharged monomer units and structures may be linear, branched or even star-shaped. They may include capping moieties which are especially effective in controlling molecular weight or altering the physical or surface-active properties. Structures and charge distributions may be tailored for application to different fiber or textile types and for varied detergent or detergent additive products.

Preferred SRA's include oligomeric terephthalate esters, typically prepared by processes involving at least one transesterification/oligomerization, often with a metal catalyst such as a titanium(IV) alkoxide. Such esters may be made using additional monomers capable of being incorporated into the ester structure through one, two, three, four or more positions, without of course forming a densely crosslinked overall structure.

Suitable SRA's include: a sulfonated product of a substantially linear ester oligomer comprised of an oligomeric ester backbone of terephthaloyl and oxyalkyleneoxy repeat units and allyl-derived sulfonated terminal moieties covalently attached to the backbone, for example as described in U.S. Pat. No. 4,968,451, Nov. 6, 1990 to J. J. Scheibel and E. P. Gosselink: such ester oligomers can be prepared by (a) ethoxylating allyl alcohol, (b) reacting the product of (a) with dimethyl terephthalate ("DMT") and 1,2-propylene glycol ("PG") in a two-stage transesterification/ oligomerization procedure and (c) reacting the product of (b) with sodium metabisulfite in water; the nonionic end-capped 1,2-propylene/polyoxyethylene terephthalate polyesters of U.S. Pat. No. 4,711,730, Dec. 8, 1987 to Gosselink et al, for example those produced by transesterification/oligomerization of poly(ethyleneglycol)

methyl ether, DMT, PG and poly(ethyleneglycol) ("PEG"); the partly- and fully- anionic-end-capped oligomeric esters of U.S. Pat. No. 4,721,580, Jan. 26, 1988 to Gosselink, such as oligomers from ethylene glycol ("EG"), PG, DMT and Na-3,6-dioxa-8-hydroxyoctanesulfonate; the nonionic-capped block polyester oligomeric compounds of U.S. Pat. No. 4,702,857, Oct. 27, 1987 to Gosselink, for example produced from DMT, Me-capped PEG and EG and/or PG, or a combination of DMT, EG and/or PG, Me-capped PEG and Na-dimethyl-5-sulfoisophthalate; and the anionic, especially sulfoaroyl, end-capped terephthalate esters of U.S. Pat. No. 4,877,896, Oct. 31, 1989 to Maldonado, Gosselink et al, the latter being typical of SRA's useful in both laundry and fabric conditioning products, an example being an ester composition made from m-sulfobenzoic acid monosodium salt, PG and DMT optionally but preferably further comprising added PEG, e.g., PEG 3400.

SRA's also include simple copolymeric blocks of ethylene terephthalate or propylene terephthalate with polyethylene oxide or polypropylene oxide terephthalate, see U.S. Pat. No. 3,959,230 to Hays, May 25, 1976 and U.S. Pat. No. 3,893,929 to Basadur, Jul. 8, 1975; cellulosic derivatives such as the hydroxyether cellulosic polymers available as METHOCEL from Dow; and the $C_1$–$C_4$ alkylcelluloses and $C_4$ hydroxyalkyl celluloses; see U.S. Pat. No. 4,000,093, Dec. 28, 1976 to Nicol, et al. Suitable SRA's characterised by poly(vinyl ester) hydrophobe segments include graft copolymers of poly(vinyl ester), e.g., $C_1$–$C_6$ vinyl esters, preferably poly(vinyl acetate), grafted onto polyalkylene oxide backbones. See European Patent Application 0 219 048, published Apr. 22, 1987 by Kud, et al. Commercially available examples include SOKALAN SRA's such as SOKALAN HP-22, available from BASF, Germany. Other SRA's are polyesters with repeat units containing 10–15% by weight of ethylene terephthalate together with 90–80% by weight of polyoxyethylene terephthalate, derived from a polyoxyethylene glycol of average molecular weight 300–5,000. Commercial examples include ZELCON 5126 from Dupont and MILEASE T from ICI.

Another preferred SRA is an oligomer having empirical formula $(CAP)_2(EG/PG)_5(T)_5(SIP)_1$ which comprises terephthaloyl (T), sulfoisophthaloyl (SIP), oxyethyleneoxy and oxy-1,2-propylene (EG/PG) units and which is preferably terminated with end-caps (CAP), preferably modified isethionates, as in an oligomer comprising one sulfoisophthaloyl unit, 5 terephthaloyl units, oxyethyleneoxy and oxy-1,2-propyleneoxy units in a defined ratio, preferably about 0.5:1 to about 10:1, and two end-cap units derived from sodium 2-(2-hydroxyethoxy)-ethanesulfonate. Said SRA preferably further comprises from 0.5% to 20%, by weight of the oligomer, of a crystallinity-reducing stabiliser, for example an anionic surfactant such as linear sodium dodecylbenzenesulfonate or a member selected from xylene-, cumene-, and toluene- sulfonates or mixtures thereof, these stabilizers or modifiers being introduced into the synthesis pot, all as taught in U.S. Pat. No. 5,415,807, Gosselink, Pan, Kellett and Hall, issued May 16, 1995. Suitable monomers for the above SRA include Na 2-(2-hydroxyethoxy)-ethanesulfonate, DMT, Na- dimethyl 5-sulfoisophthalate, EG and PG.

Yet another group of preferred SRA's are oligomeric esters comprising: (1) a backbone comprising (a) at least one unit selected from the group consisting of dihydroxysulfonates, polyhydroxy sulfonates, a unit which is at least trifunctional whereby ester linkages are formed resulting in a branched oligomer backbone, and combinations thereof; (b) at least one unit which is a terephthaloyl moiety; and (c) at least one unsulfonated unit which is a 1,2-oxyalkyleneoxy moiety; and (2) one or more capping units selected from nonionic capping units, anionic capping units such as alkoxylated, preferably ethoxylated, isethionates, alkoxylated propanesulfonates, alkoxylated propanedisulfonates, alkoxylated phenolsulfonates, sulfoaroyl derivatives and mixtures thereof. Preferred of such esters are those of empirical formula:

{(CAP)x(EG/PG)y'(DEG)y"(PEG)y'"(T)z(SIP)z'(SEG)q(B)m} wherein CAP, EG/PG, PEG, T and SIP are as defined hereinabove, (DEG) represents di(oxyethylene)oxy units; (SEG) represents units derived from the sulfoethyl ether of glycerin and related moiety units; (B) represents branching units which are at least trifunctional whereby ester linkages are formed resulting in a branched oligomer backbone; x is from about 1 to about 12; y' is from about 0.5 to about 25; y" is from 0 to about 12; y'" is from 0 to about 10; y'+y"+y'" totals from about 0.5 to about 25; z is from about 1.5 to about 25; z' is from 0 to about 12; z+z' totals from about 1.5 to about 25; q is from about 0.05 to about 12; m is from about 0.01 to about 10; and x, y', y", y'", z, z', q and m represent the average number of moles of the corresponding units per mole of said ester and said ester has a molecular weight ranging from about 500 to about 5,000.

Preferred SEG and CAP monomers for the above esters include Na-2-(2-,3-dihydroxypropoxy)ethanesulfonate ("SEG"), Na-2-{2-(2-hydroxyethoxy) ethoxy} ethanesulfonate ("SE3") and its homologs and mixtures thereof and the products of ethoxylating and sulfonating allyl alcohol. Preferred SRA esters in this class include the product of transesterifying and oligomerizing sodium 2-{2-(2-hydroxyethoxy)ethoxy}ethanesulfonate and/or sodium 2-[2-{2-(2-hydroxyethoxy}-ethoxy ethoxy]ethanesulfonate, DMT, sodium 2-(2,3-dihydroxypropoxy) ethane sulfonate, EG, and PG using an appropriate Ti(IV) catalyst and can be designated as (CAP)2(T)5(EG/PG)1.4(SEG)2.5(B)0.13 wherein CAP is $(Na+—O_3S[CH_2CH_2O]3.5)$— and B is a unit from glycerin and the mole ratio EG/PG is about 1.7:1 as measured by conventional gas chromatography after complete hydrolysis.

Additional classes of SRA's include (I) nonionic terephthalates using diisocyanate coupling agents to link up polymeric ester structures, see U.S. Pat. No. 4,201,824, Violland et al. and U.S. Pat. No. 4,240,918 Lagasse et al; (II) SRA's with carboxylate terminal groups made by adding trimellitic anhydride to known SRA's to convert terminal hydroxyl groups to trimellitate esters. With a proper selection of catalyst, the trimellitic anhydride forms linkages to the terminals of the polymer through an ester of the isolated carboxylic acid of trimellitic anhydride rather than by opening of the anhydride linkage. Either nonionic or anionic SRA's may be used as starting materials as long as they have hydroxyl terminal groups which may be esterified. See U.S. Pat. No. 4,525,524 Tung et al.; (III) anionic terephthalate-based SRA's of the urethane-linked variety, see U.S. Pat. No. 4,201,824, Violland et al; (IV) poly(vinyl caprolactam) and related co-polymers with monomers such as vinyl pyrrolidone and/or dimethylaminoethyl methacrylate, including both nonionic and cationic polymers, see U.S. Pat. No. 4,579,681, Ruppert et al.; (V) graft copolymers, in addition to the SOKALAN types from BASF made, by grafting acrylic monomers on to sulfonated polyesters; these SRA's assertedly have soil release and anti-redeposition activity similar to known cellulose ethers: see EP 279,134 A, 1988, to Rhone-Poulenc Chemie; (VI) grafts of vinyl monomers such as acrylic acid and vinyl acetate on to proteins such as caseins, see EP 457,205 A to BASF (1991); (VII) polyester-polyamide SRA's prepared by condensing adipic acid, caprolactam, and polyethylene glycol, especially for treating polyamide fabrics, see Bevan et al, DE 2,335,044 to Unilever N. V., 1974. Other useful SRA's are described in U.S. Pat. Nos. 4,240,918, 4,787,989, 4,525,524 and 4,877, 896.

Clay Soil Removal/Anti-redeposition Agents—The compositions of the present invention can also optionally contain water-soluble ethoxylated amines having clay soil removal and antiredeposition properties. Granular detergent compositions which contain these compounds typically contain from about 0.01% to about 10.0% by weight of the water-soluble ethoxylates amines; liquid detergent compositions typically contain about 0.01% to about 5%.

The most preferred soil release and anti-redeposition agent is ethoxylated tetraethylenepentamine. Exemplary ethoxylated amines are further described in U.S. Pat. No. 4,597,898, VanderMeer, issued Jul. 1, 1986. Another group of preferred clay soil removal-antiredeposition agents are the cationic compounds disclosed in European Patent Application 111,965, Oh and Gosselink, published Jun. 27, 1984. Other clay soil removal/antiredeposition agents which can be used include the ethoxylated amine polymers disclosed in European Patent Application 111,984, Gosselink, published Jun. 27, 1984; the zwitterionic polymers disclosed in European Patent Application 112,592, Gosselink, published Jul. 4, 1984; and the amine oxides disclosed in U.S. Pat. No. 4,548,744, Connor, issued Oct. 22, 1985. Other clay soil removal and/or anti redeposition agents known in the art can also be utilized in the compositions herein. See U.S. Pat. No. 4,891,160, VanderMeer, issued Jan. 2, 1990 and WO 95/32272, published Nov. 30, 1995. Another type of preferred antiredeposition agent includes the carboxy methyl cellulose (CMC) materials. These materials are well known in the art.

Polymeric Dispersing Agents—Polymeric dispersing agents can advantageously be utilized at levels from about 0.1% to about 7%, by weight, in the compositions herein, especially in the presence of zeolite and/or layered silicate builders. Suitable polymeric dispersing agents include polymeric polycarboxylates and polyethylene glycols, although others known in the art can also be used. It is believed, though it is not intended to be limited by theory, that polymeric dispersing agents enhance overall detergent builder performance, when used in combination with other builders (including lower molecular weight polycarboxylates) by crystal growth inhibition, particulate soil release peptization, and anti-redeposition.

Polymeric polycarboxylate materials can be prepared by polymerizing or copolymerizing suitable unsaturated monomers, preferably in their acid form. Unsaturated monomeric acids that can be polymerized to form suitable polymeric polycarboxylates include acrylic acid, maleic acid (or maleic anhydride), fumaric acid, itaconic acid, aconitic acid, mesaconic acid, citraconic acid and methylenemalonic acid. The presence in the polymeric polycarboxylates herein or monomeric segments, containing no carboxylate radicals such as vinylmethyl ether, styrene, ethylene, etc. is suitable provided that such segments do not constitute more than about 40% by weight.

Particularly suitable polymeric polycarboxylates can be derived from acrylic acid. Such acrylic acid-based polymers which are useful herein are the water-soluble salts of polymerized acrylic acid. The average molecular weight of such polymers in the acid form preferably ranges from about 2,000 to 10,000, more preferably from about 4,000 to 7,000 and most preferably from about 4,000 to 5,000. Water-soluble salts of such acrylic acid polymers can include, for example, the alkali metal, ammonium and substituted ammonium salts. Soluble polymers of this type are known materials. Use of polyacrylates of this type in detergent compositions has been disclosed, for example, in Diehl, U.S. Pat. No. 3,308,067, 30 issued Mar. 7, 1967.

Acrylic/maleic-based copolymers may also be used as a preferred component of the dispersing/anti-redeposition agent. Such materials include the water-soluble salts of copolymers of acrylic acid and maleic acid. The average molecular weight of such copolymers in the acid form preferably ranges from about 2,000 to 100,000, more preferably from about 5,000 to 75,000, most preferably from about 7,000 to 65,000. The ratio of acrylate to maleate segments in such copolymers will generally range from about 30:1 to about 1:1, more preferably from about 10:1 to 2:1. Water-soluble salts of such acrylic acid/maleic acid copolymers can include, for example, the alkali metal, ammonium and substituted ammonium salts. Soluble acrylate/maleate copolymers of this type are known materials which are described in European Patent Application No. 66915, published Dec. 15, 1982, as well as in EP 193,360, published Sep. 3, 1986, which also describes such polymers comprising hydroxypropylacrylate. Still other useful dispersing agents include the maleic/acrylic/vinyl alcohol terpolymers. Such materials are also disclosed in EP 193,360, including, for example, the 45/45/10 terpolymer of acrylic/maleic/vinyl alcohol.

Another polymeric material which can be included is polyethylene glycol (PEG). PEG can exhibit dispersing agent performance as well as act as a clay soil removal-antiredeposition agent. Typical molecular weight ranges for these purposes range from about 500 to about 100,000, preferably from about 1,000 to about 50,000, more preferably from about 1,500 to about 10,000.

Polyaspartate and polyglutamate dispersing agents may also be used, especially in conjunction with zeolite builders. Dispersing agents such as polyaspartate preferably have a molecular weight (avg.) of about 10,000.

Brightener—Any optical brighteners or other brightening or whitening agents known in the art can be incorporated at levels typically from about 0.011% to about 1.2%, by weight, into the detergent compositions herein. Commercial optical brighteners which may be useful in the present invention can be classified into subgroups, which include, but are not necessarily limited to, derivatives of stilbene, pyrazoline, coumarin, carboxylic acid, methinecyanines, dibenzothiophene-5,5-dioxide, azoles, 5- and 6-membered-ring heterocycles, and other miscellaneous agents. Examples of such brighteners are disclosed in "The Production and Application of Fluorescent Brightening Agents", M. Zahradnik, Published by John Wiley & Sons, New York (1982).

Specific examples of optical brighteners which are useful in the present compositions are those identified in U.S. Pat. No. 4,790,856, issued to Wixon on Dece. 13, 1988. These brighteners include the PHORWHITE series of brighteners from Verona. Other brighteners disclosed in this reference include: Tinopal UNPA, Tinopal CBS and Tinopal 5BM; available from Ciba-Geigy; Artic White CC and Artic White CWD, the 2-(4-styryl-phenyl)-2H-naptho[1,2-d]triazoles; 4,4'-bis-(1,2,3-triazol-2-yi)-stilbenes; 4,4'-bis(styryl) bisphenyls; and the amino-coumarins. Specific examples of these brighteners include 4-methyl-7-diethyl-amino coumarin; 1,2-bis(benzimidazol-2-yl)ethylene; 1,3-diphenyl-pyrazolines; 2,5-bis(benzoxazol-2-yl)thiophene; 2-styrylnaptho[1,2-d]oxazole; and 2-(stilben-4-yl)- 2H-naphtho[1,2-d]triazole. See also U.S. Pat. No. 3,646,015, issued Feb. 29, 1972 to Hamilton.

Dye Transfer Inhibiting Agents—The compositions of the present invention may also include one or more materials effective for inhibiting the transfer of dyes from one fabric to another during the cleaning process. Generally, such dye transfer inhibiting agents include polyvinyl pyrrolidone polymers, polyamine N-oxide polymers, copolymers of N-vinylpyrrolidone and N-vinylimidazole, manganese phthalocyanine, peroxidases, and mixtures thereof. If used, these agents typically comprise from about 0.01% to about 10% by weight of the composition, preferably from about 0.01% to about 5%, and more preferably from about 0.05% to about 2%.

More specifically, the polyamine N-oxide polymers preferred for use herein contain units having the following structural formula: R—$A_x$—P; wherein P is a polymerizable unit to which an N—O group can be attached or the N—O group can form part of the polymerizable unit or the N—O group can be attached to both units; A is one of the following structures: —NC(O)—, —C(O)O—, —S—, —O—, —N=; x is 0 or 1; and R is aliphatic, ethoxylated aliphatics, aromatics, heterocyclic or alicyclic groups or any combination thereof to which the nitrogen of the N—O group can be attached or the N—O group is part of these groups. Preferred polyamine N-oxides are those wherein R is a heterocyclic group such as pyridine, pyrrole, imidazole, pyrrolidine, piperidine and derivatives thereof.

The N—O group can be represented by the following general structures:

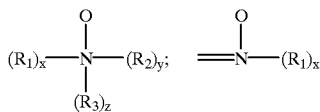

wherein $R_1$, $R_2$, $R_3$ are aliphatic, aromatic, heterocyclic or alicyclic groups or combinations thereof; x, y and z are 0 or 1; and the nitrogen of the N—O group can be attached or form part of any of the aforementioned groups. The amine oxide unit of the polyamine N-oxides has a pKa<10, preferably pKa<7, more preferred pKa<6.

Any polymer backbone can be used as long as the amine oxide polymer formed is water-soluble and has dye transfer inhibiting properties. Examples of suitable polymeric backbones are polyvinyls, polyalkylenes, polyesters, polyethers, polyamide, polyimides, polyacrylates and mixtures thereof These polymers include random or block copolymers where one monomer type is an amine N-oxide and the other monomer type is an N-oxide. The amine N-oxide polymers typically have a ratio of amine to the amine N-oxide of 10:1 to 1: 1,000,000. However, the number of amine oxide groups present in the polyamine oxide polymer can be varied by appropriate copolymerization or by an appropriate degree of N-oxidation. The polyamine oxides can be obtained in almost any degree of polymerization.

Typically, the average molecular weight is within the range of 500 to 1,000,000; more preferred 1,000 to 500,000; most preferred 5,000 to 100,000. This preferred class of materials can be referred to as "PVNO".

The most preferred polyamine N-oxide useful in the detergent compositions herein is poly(4-vinylpyridine-N-oxide) which as an average molecular weight of about 50,000 and an amine to amine N-oxide ratio of about 1:4.

Copolymers of N-vinylpyrrolidone and N-vinylimidazole polymers (referred to as a class as "PVPVI") are also preferred for use herein. Preferably the PVPVI has an average molecular weight range from 5,000 to 1,000,000, more preferably from 5,000 to 200,000, and most preferably from 10,000 to 20,000. (The average molecular weight range is determined by light scattering as described in Barth, et al., Chemical Analysis, Vol 113. "Modem Methods of Polymer Characterization", the disclosures of which are incorporated herein by reference.) The PVPVI copolymers typically have a molar ratio of N-vinylimidazole to N-vinylpyrrolidone from 1:1 to 0.2:1, more preferably from 0.8:1 to 0.3:1, most preferably from 0.6:1 to 0.4:1. These copolymers can be either linear or branched.

The present invention compositions also may employ a polyvinylpyrrolidone ("PVP") having an average molecular weight of from about 5,000 to about 400,000, preferably from about 5,000 to about 200,000, and more preferably from about 5,000 to about 50,000. PVP's are known to persons skilled in the detergent field; see, for example, EP-A-262,897 and EP-A-256,696, incorporated herein by reference. Compositions containing PVP can also contain polyethylene glycol ("PEG") having an average molecular weight from about 500 to about 100,000, preferably from about 1,000 to about 10,000. Preferably, the ratio of PEG to PVP on a ppm basis delivered in wash solutions is from about 2:1 to about 50:1, and more preferably from about 3:1 to about 10:1.

The detergent compositions herein may also optionally contain from about 0.005% to 5% by weight of certain types of hydrophilic optical brighteners which also provide a dye transfer inhibition action. If used, the compositions herein will preferably comprise from about 0.01% to 1% by weight of such optical brighteners.

The hydrophilic optical brighteners useful in the present invention are those having the structural formula:

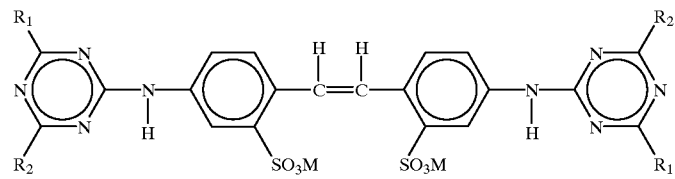

wherein $R_1$ is selected from anilino, N-2-bis-hydroxyethyl and NH-2-hydroxyethyl; $R_2$ is selected from N-2-bis-hydroxyethyl, N-2-hydroxyethyl-N-methylamino, morpholino, chloro and amino; and M is a salt-forming cation such as sodium or potassium.

When in the above formula, $R_1$ is anilino, $R_2$ is N-2-bis-hydroxyethyl and M is a cation such as sodium, the brightener is 4,4',-bis[(4-anilino-6-(N-2-bis-hydroxyethyl)-s-triazine-2-yl)amino]-2,2'-stilbenedisulfonic acid and disodium salt. This particular brightener species is commercially marketed under the tradename Tinopal-UNPA-GX by Ciba-Geigy Corporation. Tinopal-UNPA-GX is the preferred hydrophilic optical brightener useful in the detergent compositions herein.

When in the above formula, $R_1$ is anilino, $R_2$ is N-2-hydroxyethyl-N-2-methylamino and M is a cation such as sodium, the brightener is 4,4'-bis[(4-anilino-6-(N-2-hydroxyethyl-N-methylamino)-s-triazine-2-yl)amino]2,2'-stilbenedisulfonic acid disodium salt. This particular brightener species is commercially marketed under the tradename Tinopal 5BM-GX by Ciba-Geigy Corporation.

When in the above formula, $R_1$ is anilino, $R_2$ is morphilino and M is a cation such as sodium, the brightener is 4,4'-bis[(4-anilino-6-morphilino-s-triazine-2-yl)amino]2,2'-stilbenedisulfonic acid, sodium salt. This particular brightener species is commercially marketed under the tradename Tinopal AMS-GX by Ciba Geigy Corporation.

The specific optical brightener species selected for use in the present invention provide especially effective dye transfer inhibition performance benefits when used in combination with the selected polymeric dye transfer inhibiting agents hereinbefore described. The combination of such selected polymeric materials (e.g., PVNO and/or PVPVI) with such selected optical brighteners (e.g., Tinopal UNPA-GX, Tinopal 5BM-GX and/or Tinopal AMS-GX) provides significantly better dye transfer inhibition in aqueous wash solutions than does either of these two detergent composition components when used alone. Without being bound by theory, it is believed that such brighteners work this way because they have high affinity for fabrics in the wash solution and therefore deposit relatively quick on these fabrics. The extent to which brighteners deposit on fabrics in the wash solution can be defined by a parameter called the "exhaustion coefficient". The exhaustion coefficient is in general as the ratio of a) the brightener material deposited on fabric to b) the initial brightener concentration in the wash liquor. Brighteners with relatively high exhaustion coefficients are the most suitable for inhibiting dye transfer in the context of the present invention.

Of course, it will be appreciated that other, conventional optical brightener types of compounds can optionally be used in the present compositions to provide conventional fabric "brightness" benefits, rather than a true dye transfer inhibiting effect. Such usage is conventional and well-known to detergent formulations.

Chelating Agents—The detergent compositions herein may also optionally contain one or more iron and/or manganese chelating agents. Such chelating agents can be selected from the group consisting of amino carboxylates, amino phosphonates, polyfunctionally-substituted aromatic chelating agents and mixtures therein, all as hereinafter defined. Without intending to be bound by theory, it is believed that the benefit of these materials is due in part to their exceptional ability to remove iron and manganese ions from washing solutions by formation of soluble chelates.

Amino carboxylates useful as optional chelating agents include ethylenediaminetetracetates, N-hydroxyethylethylenediaminetriacetates, nitrilotriacetates, ethylenediamine tetraproprionates, triethylenetetraaminehexacetates, diethylenetriaminepentaacetates, and ethanoldiglycines, alkali metal. ammonium, and substituted ammonium salts therein and mixtures therein.

Amino phosphonates are also suitable for use as chelating agents in the compositions of the invention when at lease low levels of total phosphorus are permitted in detergent compositions, and include ethylenediaminetetrakis (methylenephosphonates) as DEQUEST. Preferred, these amino phosphonates to not contain alkyl or alkenyl groups with more than about 6 carbon atoms.

Polyfunctionally-substituted aromatic chelating agents are also useful in the compositions herein. See U.S. Pat. No. 3,812,044, issued May 21, 1974, to Connor et al. Preferred compounds of this type in acid form are dihydroxydisulfobenzenes such as 1,2-dihydroxy-3,5-disulfobenzene.

A preferred biodegradable chelator for use herein is ethylenediamine disuccinate ("EDDS"), especially the [S,S] isomer as described in U.S. Pat. No. 4,704,233, Nov. 3, 1987, to Hartman and Perkins.

The compositions herein may also contain water-soluble methyl glycine diacetic acid (MGDA) salts (or acid form) as a chelant or co-builder useful with, for example, insoluble builders such as zeolites, layered silicates and the like.

If utilized, these chelating agents will generally comprise from about 0.1% to about 15% by weight of the detergent compositions herein. More preferably, if utilized, the chelating agents will comprise from about 0.1% to about 3.0% by weight of such compositions.

Suds Suppressors—Compounds for reducing or suppressing the formation of suds can be incorporated into the compositions of the present invention. Suds suppression can be of particular importance in the so-called "high concentration cleaning process" as described in U.S. Pat. No. 4,489,455 and 4,489,574 and in front-loading European-style washing machines.

A wide variety of materials may be used as suds suppressors, and suds suppressors are well known to those skilled in the art. See, for example, Kirk Othmer Encyclopedia of Chemical Technology, Third Edition, Volume 7, pages 430–447 (John Wiley & Sons, Inc., 1979). One category of suds suppressor of particular interest encompasses monocarboxylic fatty acid and soluble salts therein. See U.S. Pat. No. 2,954,347, issued Sep. 27, 1960 to Wayne St. John. The monocarboxylic fatty acids and salts thereof used as suds suppressor typically have hydrocarbyl chains of 10 to about 24 carbon atoms, preferably 12 to 18 carbon atoms. Suitable salts include the alkali metal salts such as sodium, potassium, and lithium salts, and ammonium and alkanolammonium salts.

The detergent compositions herein may also contain non-surfactant suds suppressors. These include, for example: high molecular weight hydrocarbons such as paraffin, fatty acid esters (e.g., fatty acid triglycerides), fatty acid esters of monovalent alcohols, aliphatic $C_{18}$–$C_{40}$ ketones (e.g., stearone), etc. Other suds inhibitors include N-alkylated amino triazines such as tri- to hexa-alkylmelamines or di- to tetra-alkyldiamine chlortriazines formed as products of cyanuric chloride with two or three moles of a primary or secondary amine containing 1 to 24 carbon atoms, propylene oxide, and monostearyl phosphates such as monostearyl alcohol phosphate ester and monostearyl di-alkali metal (e.g., K, Na, and Li) phosphates and phosphate esters. The hydrocarbons such as paraffin and haloparaffin can be utilized in liquid form. The liquid hydrocarbons will be liquid at room temperature and atmospheric pressure, and will have a pour point in the range of about −40° C. and about 50° C., and a minimum boiling point not less than about 110° C. (atmospheric pressure). It is also known to utilize waxy hydrocarbons, preferably having a melting point below about 100° C. The hydrocarbons constitute a preferred category of suds suppressor for detergent compositions. Hydrocarbon suds suppressors are described, for example, in U.S. Pat. No. 4,265,779, issued May 5, 1981 to Gandolfo et al. The hydrocarbons, thus, include aliphatic, alicyclic, aromatic, and heterocyclic saturated or unsaturated hydrocarbons having from about 12 to about 70 carbon atoms. The term "paraffin," as used in this suds suppressor discussion, is intended to include mixtures of true paraffins and cyclic hydrocarbons.

Another preferred category of non-surfactant suds suppressors comprises silicone suds suppressors. This category includes the use of polyorganosiloxane oils, such as polydimethylsiloxane, dispersions or emulsions of polyorganosiloxane oils or resins, and combinations of polyorganosiloxane with silica particles wherein the polyorganosiloxane is chemisorbed or fused onto the silica. Silicone suds suppressors are well known in the art and are, for example, disclosed in U.S. Pat. No. 4,265,779, issued May 5, 1981 to Gandolfo et al and European Patent Application No. 89307851.9, published Feb. 7, 1990, by Starch, M. S.

Other silicone suds suppressors are disclosed in U.S. Pat. No. 3,455,839 which relates to compositions and processes for defoaming aqueous solutions by incorporating therein small amounts of polydimethylsiloxane fluids.

Mixtures of silicone and silanated silica are described, for instance, in German Patent Application DOS 2,124,526. Silicone defoamers and suds controlling agents in granular detergent compositions are disclosed in U.S. Pat. No. 3,933,672, Bartolotta et al, and in U.S. Pat. No. 4,652,392, Baginski et al, issued Mar. 24, 1987.

An exemplary silicone based suds suppressor for use herein is a suds suppressing amount of a suds controlling agent consisting essentially of:

(i) polydimethylsiloxane fluid having a viscosity of from about 20 cs. to about 1,500 cs. at 25° C.;

(ii) from about 5 to about 50 parts per 100 parts by weight of (i) of siloxane resin composed of $(CH_3)_3SiO_{1/2}$ units of $SiO_2$ units in a ratio of from $(CH_3)_3 Si_{1/2}$ units and to $SiO_2$ units of from about 0.6:1 to about 1.2:1; and (iii) from about 1 to about 20 parts per 100 parts by weight of (i) of a solid silica gel.

In the preferred silicone suds suppressor used herein, the solvent for a continuous phase is made up of certain polyethylene glycols or polyethylene-polypropylene glycol copolymers or mixtures thereof (preferred), or polypropylene glycol. The primary silicone suds suppressor is branched/crosslinked and preferably not linear.

To illustrate this point further, typical liquid laundry detergent compositions with controlled suds will optionally comprise from about 0.001 to about 1, preferably from about 0.01 to about 0.7, most preferably from about 0.05 to about 0.5, weight % of said silicone uds suppressor, which comprises (1) a nonaqueous emulsion of a primary antifoam agent which is a mixture of (a) a polyorganosiloxane, (b) a resinous siloxane or a silicone resin-producing silicone compound, (c) a finely divided filler material, and (d) a catalyst to promote the reaction of mixture components (a), (b) and (c), to form silanolates; (2) at least one nonionic silicone surfactant; and (3) polyethylene glycol or a copolymer of polyethylene-polypropylene glycol having a solubility in water at room temperature of more than about 2 weight %; and without polypropylene glycol. Similar amounts can be used in granular compositions, gels, etc. See also U.S. Pat. No. 4,978,471, Starch, issued Dec. 18, 1990, and U.S. Pat. No. 4,983,316, Starch, issued Jan. 8, 1991, U.S. Pat. No. 5,288,431, Huber et al., issued Feb. 22, 1994, and U.S. Pat. Nos. 4,639,489 and 4,749,740, Aizawa et al at column 1, line 46 through column 4, line 35.

The silicone suds suppressor herein preferably comprises polyethylene glycol and a copolymer of polyethylene glycol/polypropylene glycol, all having an average molecular weight of less than about 1,000, preferably between about 100 and 800. The polyethylene glycol and polyethylene/polypropylene copolymers herein have a solubility in water at room temperature of more than about 2 weight %, preferably more than about 5 weight %.

The preferred solvent herein is polyethylene glycol having an average molecular weight of less than about 1,000, more preferably between about 100 and 800, most preferably between 200 and 400, and a copolymer of polyethylene glycol/polypropylene glycol, preferably PPG 200/PEG 300. Preferred is a weight ratio of between about 1:1 and 1:10, most preferably between 1:3 and 1:6, of polyethylene glycol:copolymer of polyethylene-polypropylene glycol.

The preferred silicone suds suppressors used herein do not contain polypropylene glycol, particularly of 4,000 molecular weight. They also preferably do not contain block copolymers of ethylene oxide and propylene oxide, like PLURONIC L101.

Other suds suppressors useful herein comprise the secondary alcohols (e.g., 2-alkyl alkanols) and mixtures of such alcohols with silicone oils, such as the silicones disclosed in U.S. Pat. No. 4,798,679, 4,075,118 and EP 150,872. The secondary alcohols include the $C_6$–$C_{16}$ alkyl alcohols having a $C_1$–$C_{16}$ chain. A preferred alcohol is 2-butyl octanol, which is available from Condea under the trademark ISOFOL 12. Mixtures of secondary alcohols are available under the trademark ISALCHEM 123 from Enichem. Mixed suds suppressors typically comprise mixtures of alcohol+silicone at a weight ratio of 1:5 to 5:1.

For any detergent compositions to be used in automatic laundry washing machines, suds should not form to the extent that they overflow the washing machine. Suds suppressors, when utilized, are preferably present in a "suds suppressing amount." By "suds suppressing amount" is meant that the formulator of the composition can select an amount of this suds controlling agent that will sufficiently control the suds to result in a low-sudsing laundry detergent for use in automatic laundry washing machines.

The compositions herein will generally comprise from 0% to about 10% of suds suppressor. When utilized as suds suppressors, monocarboxylic fatty acids, and salts therein, will be present typically in amounts up to about 5%, by weight, of the detergent composition. Preferably, from about 0.5% to about 3% of fatty monocarboxylate suds suppressor is utilized. Silicone suds suppressors are typically utilized in amounts up to about 2.0%, by weight, of the detergent composition, although higher amounts may be used. This upper limit is practical in nature, due primarily to concern with keeping costs minimized and effectiveness of lower amounts for effectively controlling sudsing. Preferably from about 0.01% to about 1% of silicone suds suppressor is used, more preferably from about 0.25% to about 0.5%. As used herein, these weight percentage values include any silica that may be utilized in combination with polyorganosiloxane, as well as any adjunct materials that may be utilized. Monostearyl phosphate suds suppressors are generally utilized in amounts ranging from about 0.1% to about 2%, by weight, of the composition. Hydrocarbon suds suppressors are typically utilized in amounts ranging from about 0.01% to about 5.0%, although higher levels can be used. The alcohol suds suppressors are typically used at 0.2%–3% by weight of the finished compositions.

Alkoxylated Polycarboxylates—Alkoxylated polycarboxylates such as those prepared from polyacrylates are useful herein to provide additional grease removal performance. Such materials are described in WO 91/08281 and PCT 90/01815 at p. 4 et seq., incorporated herein by reference. Chemically, these materials comprise polyacrylates having one ethoxy side-chain per every 7–8 acrylate units. The side-chains are of the formula —$(CH_2CH_2O)_m(CH_2)_nCH_3$ wherein m is 2–3 and n is 6–12. The side-chains are ester-linked to the polyacrylate "backbone" to provide a "comb" polymer type structure. The molecular weight can vary, but is typically in he range of about 2000 to about 50,000. Such alkoxylated polycarboxylates can comprise from about 0.05% to about 10%, by weight, of the compositions herein.

Fabric Softeners—Various through-the-wash fabric softeners, especially the impalpable smectite clays of U.S. Pat. No. 4,062,647, Storm and Nirschl, issued Dec. 13, 1977, as well as other softener clays known in the art, can optionally be used typically at levels of from about 0.5% to about 10% by weight in the present compositions to provide fabric softener benefits concurrently with fabric cleaning. Clay softeners can be used in combination with amine and cationic softeners as disclosed, for example, in U.S. Pat. No. 4,375,416, Crisp et al, Mar. 1, 1983 and U.S. Pat. No. 4,291,071, Harris et al, issued Sep. 22, 1981.

Perfumes—Perfumes and perfumery ingredients useful in the present compositions and processes comprise a wide variety of natural and synthetic chemical ingredients, including, but not limited to, aldehydes, ketones, esters, and the like. Also included are various natural extracts and essences which can comprise complex mixtures of ingredients, such as orange oil, lemon oil, rose extract. lavender, musk, patchouli, balsamic essence, sandalwood oil, pine oil, cedar, and the like. Finished perfumes can comprise extremely complex mixtures of such ingredients. Finished perfumes typically comprise from about 0.01% to about 2%, by weight, of the detergent compositions herein, and individual perfumery ingredients can comprise from about 0.0001% to about 90% of a finished perfume composition.

Several perfume formulations are set forth in Example XXI, hereinafter. Non-limiting examples of perfume ingredients useful herein include: 7-acetyl-1,2,3,4,5,6,7,8-octahydro-1,1,6,7-tetramethyl naphthalene; ionone methyl; ionone gamma methyl; methyl cedrylone; methyl dihydro-jasmonate; methyl 1,6,10-trimethyl-2,5,9-cyclododecatrien-1-yl ketone; 7-acetyl-1,1,3,4,4,6-hexamethyl tetralin; 4-acetyl-6-tert-butyl-1,1-dimethyl indane; para-hydroxy-phenyl-butanone; benzophenone; methyl beta-naphthyl ketone; 6-acetyl-1,1,2,3,3,5-hexamethyl indane; 5-acetyl-3-isopropyl-1,1,2,6-tetramethyl indane; 1-dodecanal, 4-(4-hydroxy-4-methylpentyl)-3-cyclohexene-1-carboxaldehyde; 7-hydroxy-3,7-dimethyl ocatanal; 10-undecen-1-al; iso-hexenyl cyclohexyl carboxaldehyde; formyl tricyclodecane; condensation products of hydroxy-citronellal and methyl anthranilate, condensation products of hydroxycitronellal and indol, condensation products of phenyl acetaldehyde and indol; 2-methyl-3-(para-tert-butylphenyl)-propionaldehyde; ethyl vanillin; heliotropin; hexyl cinnamic aldehyde; amyl cinnamic aldehyde; 2-methyl-2-(para-iso-propylphenyl)-propionaldehyde; coumarin; decalactone gamma; cyclopentadecanolide; 16-hydroxy-9-hexadecenoic acid lactone; 1,3,4,6,7,8-hexahydro-4,6,6,7,8,8-hexamethylcyclopenta-gamma-2-benzopyrane; beta-naphthol methyl ether; ambroxane; dodecahydro-3a,6,6,9a-tetra-methylnaphtho[2,1b]furan; cedrol, 5-(2,2,3-trimethylcyclopent-3-enyl)-3-methylpentan-2-ol; 2-ethyl-4-(2,2,3-trimethyl-3-cyclopenten-1-yl)-2-buten-1-ol; caryophyllene alcohol; tricyclodecenyl propionate; tricyclodecenyl acetate; benzyl salicylate; cedryl acetate; and para-(tert-butyl) cyclohexyl acetate.

Particularly preferred perfume materials are those that provide the largest odor improvements in finished product compositions containing cellulases. These perfumes include but are not limited to: hexyl cinnamic aldehyde; 2-methyl-3-(para-tert-butylphenyl)-propionaldehyde; 7-acetyl-1,2,3, 4,5,6,7,8-octahydro-1,1,6,7-tetramethyl naphthalene; benzyl salicylate; 7-acetyl-1,1,3,4,4,6-hexamethyl tetralin; para-tert-butyl cyclohexyl acetate; methyl dihydro jasmonate; beta-napthol methyl ether; methyl beta-naphthyl ketone; 2-methyl-2-(para-iso-propylphenyl)-propionaldehyde; 1,3, 4,6,7,8-hexahydro-4,6,6,7,8,8-hexamethyl-cyclopenta-gamma-2-benzopyrane; dodecahydro-3a,6,6,9a-tetramethylnaphtho[2,1b] furan; anisaldehyde; coumarin; cedrol; vanillin; cyclopentadecanolide; tricyclodecenyl acetate; and tricyclodecenyl propionate.

Other perfume materials include essential oils, resinoids, and resins from a variety of sources including, but not limited to: Peru balsam, Olibanum resinoid, styrax, labdanum resin nutmeg, cassia oil, benzoin resin, coriander and lavandin. Still other perfume chemicals include phenyl ethyl alcohol, terpineol, linalool, linalyl acetate, geraniol, nerol, 2-(1,1-dimethylethyl)-cyclohexanol acetate, benzyl acetate, and eugenol. Carriers such as diethylphthalate can be used in the finished perfume compositions.

Other Ingredients—A wide variety of other ingredients useful in detergent compositions can be included in the compositions herein, including other active ingredients, carriers, hydrotropes, processing aids, dyes or pigments, solvents for liquid formulations, solid fillers for bar compositions, etc. If high sudsing is desired, suds boosters such as the $C_{10}$–$C_{16}$ alkanolamides can be incorporated into the compositions, typically at 1%–10% levels. The $C_{10}$–$C_{14}$ monoethanol and diethanol amides illustrate a typical class of such suds boosters. Use of such suds boosters with high sudsing adjunct surfactants such as the amine oxides, betaines and sultaines noted above is also advantageous. If desired, water-soluble magnesium and/or calcium salts such as $MgC_{12}$, $MgSO_4$, $CaC_{12}$, $CaSO_4$ and the like, can be added at levels of, typically, 0.1%–2%, to provide additional suds and to enhance grease removal performance.

Various detersive ingredients employed in the present compositions optionally can be further stabilized by absorbing said ingredients onto a porous hydrophobic substrate, then coating said substrate with a hydrophobic coating. Preferably, the detersive ingredient is admixed with a surfactant before being absorbed into the porous substrate. In use, the detersive ingredient is released from the substrate into the aqueous washing liquor, where it performs its intended detersive function.

To illustrate this technique in more detail, a porous hydrophobic silica (trademark SIPERNAT D10, DeGussa) is admixed with a proteolytic enzyme solution containing 3%–5% of $C_{13-15}$ ethoxylated alcohol (EO 7) nonionic surfactant. Typically, the enzyme/surfactant solution is 2.5× the weight of silica. The resulting powder is dispersed with stirring in silicone oil (various silicone oil viscosities in the range of 500–12,500 can be used). The resulting silicone oil dispersion is emulsified or otherwise added to the final detergent matrix. By this means, ingredients such as the aforementioned enzymes, bleaches, bleach activators, bleach catalysts, photoactivators, dyes, fluorescers, fabric conditioners and hydrolyzable surfactants can be "protected" for use in detergents, including liquid laundry detergent compositions.

Liquid detergent compositions can contain water and other solvents as carriers. Low molecular weight primary or secondary alcohols exemplified by methanol, ethanol, propanol, and isopropanol are suitable. Monohydric alcohols are preferred for solubilizing surfactant, but polyols such as those containing from 2 to about 6 carbon atoms and from 2 to about 6 hydroxy groups (e.g., 1,3-propanediol, ethylene glycol, glycerine, and 1,2-propanediol) can also be used. The compositions may contain from 5% to 90%, typically 10% to 50% of such carriers.

The detergent compositions herein will preferably be formulated such that, during use in aqueous cleaning operations, the wash water will have a pH of between about 6.5 and about 11, preferably between about 7.5 and 10.5. Liquid dishwashing product formulations preferably have a pH between about 6.8 and about 9.0. Laundry products are typically at pH 9–11. Techniques for controlling pH at recommended usage levels include the use of buffers, alkalis, acids, etc., and are well known to those skilled in the art.

Form of the compositions

The compositions in accordance with the invention can take a variety of physical forms including granular, tablet, bar and liquid forms. The compositions are particularly the so-called concentrated granular detergent compositions adapted to be added to a washing machine by means of a dispensing device placed in the machine drum with the soiled fabric load.

The mean particle size of the components of granular compositions in accordance with the invention should preferably be such that no more that 5% of particles are greater than 1.7 mm in diameter and not more than 5% of particles are less than 0.5 mm in diameter.

The term mean particle size as defined herein is calculated by sieving a sample of the composition into a number of fractions (typically 5 fractions) on a series of Tyler sieves. The weight fractions thereby obtained are plotted against the aperture size of the sieves. The mean particle size is taken to be the aperture size through which 50% by weight of the sample would pass.

The bulk density of granular detergent compositions in accordance with the present invention typically have a bulk density of at least 600 g/liter, more preferably from 650 g/liter to 1200 g/liter.Bulk density is measured by means of a simple funnel and cup device consisting of a conical funnel moulded rigidly on a base and provided with a flap valve at its lower extremity to allow the contents of the funnel to be emptied into an axially aligned cylindrical cup disposed below the funnel. The funnel is 130 mm high and has internal diameters of 130 mm and 40 mm at its respective upper and lower extremities. It is mounted so that the lower extremity is 140 mm above the upper surface of the base. The cup has an overall height of 90 mm, an internal height of 87 mm and an internal diameter of 84 mm. Its nominal volume is 500 ml.

To carry out a measurement, the funnel is filled with powder by hand pouring, the flap valve is opened and powder allowed to overfill the cup. The filled cup is removed from the frame and excess powder removed from the cup by passing a straight edged implement eg; a knife, across its upper edge. The filled cup is then weighed and the value obtained for the weight of powder doubled to provide a bulk density in g/liter. Replicate measurements are made as required.

Mid-chain branched primary alkyl 1olyoxyalkylene agglomerate particles

The mid-chain branched primary alkyl polyoxyalkylene system herein is preferably present in granular compositions in the form of mid-chain branched primary alkyl polyoxyalkylene agglomerate particles, which may take the form of flakes, prills, marumes, noodles, ribbons, but preferably take the form of granules. The most preferred way to process the particles is by agglomerating powders (e.g. aluminosilicate, carbonate) with high active mid-chain branched primary alkyl polyoxyalkylene pastes and to control the particle size of the resultant agglomerates within specified limits. Such a process involves mixing an effective amount of powder with a high active mid-chain branched primary alkyl polyoxyalkylene paste in one or more agglomerators such as a pan agglomerator, a Z-blade mixer or more preferably an in-line mixer such as those manufactured by Schugi (Holland) BV, 29 Chroomstraat 8211 AS, Lelystad, Netherlands, and Gebruder Lodige Maschinenbau GmbH, D-4790 Paderborn 1, Elsenerstrasse 7-9, Postfach 2050, Germany. Most preferably a high shear mixer is used, such as a Lodige CB (Trade Name).

A high active mid-chain branched primary alkyl polyoxyalkylene paste comprising from 50% by weight to 95% by weight, preferably 70% by weight to 85% by weight of mid-chain branched primary alkyl polyoxyalkylene is typically used. The paste may be pumped into the agglomerator at a temperature high enough to maintain a pumpable viscosity, but low enough to avoid degradation of the surfactants used. An operating temperature of the paste of 50° C. to 80° C. is typical.

Laundry washing method

Machine laundry methods herein typically comprise treating soiled laundry with an aqueous wash solution in a washing machine having dissolved or dispensed therein an effective amount of a machine laundry detergent composition in accord with the invention. By an effective amount of the detergent composition it is meant from 20 g to 300 g of product dissolved or dispersed in a wash solution of volume from 5 to 65 liters, as are typical product dosages and wash solution volumes commonly employed in conventional machine laundry methods.

As noted, the mid-chain branched primary alkyl polyoxyalkylene surfactants are used herein in detergent compositions, preferably in combination with other detersive surfactants, at levels which are effective for achieving at least a directional improvement in cleaning performance. In the context of a fabric laundry composition, such "usage levels" can vary depending not only on the type and severity of the soils and stains, but also on the wash water temperature, the volume of wash water and the type of washing machine.

For example, in a top-loading, vertical axis U.S.-type automatic washing machine using about 45 to 83 liters of water in the wash bath, a wash cycle of about 10 to about 14 minutes and a wash water temperature of about 10° C. to about 50° C., it is preferred to include from about 2 ppm to about 625 ppm, preferably from about 2 ppm to about 550 ppm, more preferably from about 10 ppm to about 235 ppm, of the mid-chain branched primary alkyl polyoxyalkylene surfactant in the wash liquor. On the basis of usage rates of from about 50 ml to about 150 ml per wash load, this translates into an in-product concentration (wt.) of the mid-chain branched primary alkyl polyoxyalkylene surfactant of from about 0.1% to about 40%, preferably about 0.1% to about 35%, more preferably from about 0.5% to about 15%, for a heavy-duty liquid laundry detergent. On the basis of usage rates of from about 30 g to about 950 g per wash load, for dense ("compact") granular laundry detergents (density above about 650 g/l) this translates into an in-product concentration (wt.) of the mid-chain branched primary alkyl polyoxyalkylene surfactant of from about 0.1% to about 50%, preferably from about 0.1% to about 35%, and more preferably from about 0.5% to about 15%. On the basis of usage rates of from about 80 g to about 100 g per load for spray-dried granules (i.e., "fluffy"; density below about 650 g/l), this translates into an in-product concentration (wt.) of the mid-chain branched primary alkyl polyoxyalkylene surfactant of from about 0.07% to about 35%, preferably from about 0.07 to about 25%, and more preferably from about 0.35% to about 11%.

For example, in a front-loading, horizontal-axis European-type automatic washing machine using about 8 to 15 liters of water in the wash bath, a wash cycle of about 10 to about 60 minutes and a wash water temperature of about 30° C. to about 95° C., it is preferred to include from about 3 ppm to about 14,000 ppm, preferably from about 3 ppm to about 10,000 ppm, more preferably from about 15 ppm to about 4200 ppm, of the mid-chain branched primary alkyl polyoxyalkylene surfactant in the wash liquor. On the basis of usage rates of from about 45 ml to about 270 ml per wash load, this translates into an in-product concentration (wt.) of the mid-chain branched primary alkyl polyoxyalkylene surfactant of from about 0.1% to about 50%, preferably about 0.1% to about 35%, more preferably from about 0.5% to about 15%, for a heavy-duty liquid laundry detergent. On the basis of usage rates of from about 40 g to about 210 g per wash load, for dense ("compact") granular laundry detergents (density above about 650 g/l) this translates into an in-product concentration (wt.) of the mid-chain branched primary alkyl polyoxyalkylene surfactant of from about 0.12% to about 53%, preferably from about 0.12% to about 46%, and more preferably from about 0.6% to about 20%. On the basis of usage rates of from about 140 g to about 400 g per load for spray-dried granules (i.e., "fluffy"; density below about 650 g/l), this translates into an in-product concentration (wt.) of the mid-chain branched primary alkyl polyoxyalkylene surfactant of from about 0.03% to about 34%, preferably from about 0.03% to about 24%, and more preferably from about 0.15% to about 10%.

For example, in a top-loading, vertical-axis Japanese-type automatic washing machine using about 26 to 52 liters of water in the wash bath, a wash cycle of about 8 to about 15 minutes and a wash water temperature of about 5° C. to about 25° C., it is preferred to include from about 0.67 ppm to about 270 ppm, preferably from about 0.67 ppm to about 236 ppm, more preferably from about 3.4 ppm to about 100 ppm, of the mid-chain branched primary alkyl polyoxyalkylene surfactant in the wash liquor. On the basis of usage rates of from about 20 ml to about 30 ml per wash load, this translates into an in-product concentration (wt.) of the mid-chain branched primary alkyl polyoxyalkylene surfactant of from about 0.1% to about 40%, preferably about 0.1% to about 35%, more preferably from about 0.5% to about 15%, for a heavy-duty liquid laundry detergent. On the basis of usage rates of from about 18 g to about 35 g per wash load, for dense ("compact") granular laundry detergents (density above about 650 g/l) this translates into an in-product concentration (wt.) of the mid-chain branched primary alkyl polyoxyalkylene surfactant of from about 0.1% to about 50%, preferably from about 0.1% to about 35%, and more preferably from about 0.5% to about 15%. On the basis of usage rates of from about 30 g to about 40 g per load for spray-dried granules (i.e., "fluffy"; density below about 650 g/l), this translates into an in-product concentration (wt.) of the mid-chain branched primary alkyl polyoxyalkylene surfactant of from about 0.06% to about 44%, preferably from about 0.06% to about 30%, and more preferably from about 0.3% to about 13%.

As can be seen from the foregoing, the amount of mid-chain branched primary alkyl polyoxyalkylene surfactant used in a machine-wash laundering context can vary, depending on the habits and practices of the user, the type of washing machine, and the like. In this context, however, one heretofore unappreciated advantage of the mid-chain branched primary alkyl polyoxyalkylene surfactants is their ability to provide at least directional improvements in performance over a spectrum of soils and stains even when used at relatively low levels with respect to the other surfactants (generally anionics or anionic/nonionic mixtures) in the finished compositions.

In a preferred use aspect a dispensing device is employed in the washing method. The dispensing device is charged with the detergent product, and is used to introduce the product directly into the drum of the washing machine before the commencement of the wash cycle. Its volume capacity should be such as to be able to contain sufficient detergent product as would normally be used in the washing method.

Once the washing machine has been loaded with laundry the dispensing device containing the detergent product is placed inside the drum. At the commencement of the wash cycle of the washing machine water is introduced into the drum and the drum periodically rotates. The design of the dispensing device should be such that it permits containment of the dry detergent product but then allows release of this product during the wash cycle in response to its agitation as the drum rotates and also as a result of its contact with the wash water.

To allow for release of the detergent product during the wash the device may possess a number of openings through which the product may pass. Alternatively, the device may be made of a material which is permeable to liquid but impermeable to the solid product, which will allow release of dissolved product. Preferably, the detergent product will be rapidly released at the start of the wash cycle thereby providing transient localised high concentrations of product in the drum of the washing machine at this stage of the wash cycle.

Preferred dispensing devices are reusable and are designed in such a way that container integrity is maintained in both the dry state and during the wash cycle. Especially preferred dispensing devices for use with the composition of the invention have been described in the following patents; GB-B-2, 157, 717, GB-B-2, 157, 718, EP-A-0201376, EP-A-0288345 and EP-A-0288346. An article by J. Bland published in Manufacturing Chemist, Nov. 1989, pages 41–46 also describes especially preferred dispensing devices for use with granular laundry products which are of a type commonly know as the "granulette". Another preferred dispensing device for use with the compositions of this invention is disclosed in PCT Patent Application No. WO94/11562.

Especially preferred dispensing devices are disclosed in European Patent Application Publication Nos. 0343069 & 0343070. The latter Application discloses a device comprising a flexible sheath in the form of a bag extending from a support ring defining an orifice, the orifice being adapted to admit to the bag sufficient product for one washing cycle in a washing process. A portion of the washing medium flows through the orifice into the bag, dissolves the product, and the solution then passes outwardly through the orifice into the washing medium. The support ring is provided with a masking arrangemnt to prevent egress of wetted, undissolved, product, this arrangement typically comprising radially extending walls extending from a central boss in a spoked wheel configuration, or a similar structure in which the walls have a helical form.

Alternatively, the dispensing device may be a flexible container, such as a bag or pouch. The bag may be of fibrous construction coated with a water impermeable protective material so as to retain the contents, such as is disclosed in European published Patent Application No. 0018678. Alternatively it may be formed of a water-insoluble synthetic polymeric material provided with an edge seal or closure designed to rupture in aqueous media as disclosed in European published Patent Application Nos. 0011500, 0011501, 0011502, and 0011968. A convenient form of water frangible closure comprises a water soluble adhesive disposed along and sealing one edge of a pouch formed of a water impermeable polymeric film such as polyethylene or polypropylene.

Machine dishwashing method

Any suitable methods for machine washing or cleaning soiled tableware, particularly soiled silverware are envisaged.

A preferred machine dishwashing method comprises treating soiled articles selected from crockery, glassware, hollowware, silverware and cutlery and mixtures thereof, with an aqueous liquid having dissolved or dispensed therein an effective amount of a machine dishwashing composition in accord with the invention. By an effective amount of the machine dishwashing composition it is meant from 8 g to 60 g of product dissolved or dispersed in a wash solution of volume from 3 to 10 liters, as are typical product dosages and wash solution volumes commonly employed in conventional machine dishwashing methods.

Packaging for the compositions

Commercially marketed executions of the bleaching compositions can be packaged in any suitable container including those constructed from paper, cardboard, plastic materials and any suitable laminates. A preferred packaging execution is described in European Application No. 94921505.7.

In the following Examples, the abbreviations for the various ingredients used for the compositions have the following meanings.

| | |
|---|---|
| LAS | Sodium linear alkyl benzene sulfonate |
| MBxAEy | Mid-chain branched primary alkyl (average total carbons = x) ethoxylate (average EO = y) |
| Endolase | Endoglunase enzyme of activity 3000 CEVU/g sold by NOVO Industries A/S |
| MEA | Monoethanolamine |
| PG | Propanediol |
| BPP | Butoxy-propoxy-propanol |
| EtOH | Ethanol |
| NaOH | Solution of sodium hydroxide |
| NaTS | Sodium toluene sulfonate |
| Citric acid | Anhydrous citric acid |
| CxyFA | $C_{1x}$—$C_{1y}$ fatty acid |
| CxyEz | A $C_{1x-1y}$ branched primary alcohol condensed with an average of z moles of ethylene oxide |
| *CxyEz | A $C_{xy}$ branched primary alcohol condensed with an average of z moles of ethylene oxide |
| Carbonate | Anhydrous sodium carbonate with a partice size between 200 μm and 900 μm |
| Citrate | Tri-sodium citrate dihydrate of activity 86.4% with a particle size distribution between 425 μm and 850 μm |
| TFAA | C16–18 alkyl N-methyl glucamide |
| LMFAA | C12–14 alkyl N-methyl glucamide |
| APA | C8–C10 amido propyl dimethyl amine |
| Fatty Acid (C12/14) | C12—C14 fatty acid |
| Fatty Acid (TPK) | Topped palm kernel fatty acid |
| Fatty Acid (RPS) | Rapeseed fatty acid |
| Borax | Na tetraborate decahydrate |
| PAA | Polyacrylic Acid (mw = 4500) |
| PEG | Polyethylene glycol (mw = 4600) |
| MES | Alkyl methyl ester sulfonate |
| SAS | Secondary alkyl sulfate |
| NaPS | Sodium paraffin sulfonate |
| C45AS | Sodium C14—C15 linear alkyl sulfate |
| CxyAS | Sodium $C_{1x}$—$C_{1y}$ alkyl sulfate (or other salt if specified) |
| CxyEzS | Sodium $C_{1x}$—$C_{1y}$ alkyl sulfate condensed with z moles of ethylene oxide (or other salt if specified) |
| Soap | C12–18 alkyl carboxylate, sodium salt |
| SCS | Sodium cumene sulfonate |
| AQA | $R_2.N^+(CH_3)_x((C_2H_4O)yH)z$ with $R_2 = C_8$—$C_{18\ x\ +\ z\ -\ 3}$, $x = 0$ to 3, $z = 0$ to 3, $y = 1$ to 15. |
| STPP | Anhydrous sodium tripolyphosphate |
| Zeolite A | Hydrated Sodium Aluminosilicate of formula $Na_{12}(A1O_2SiO_2)_{12}.27H_2O$ having a primary particle size in the range from 0.1 to 10 micrometers |
| NaSKS-6 | Crystalline layered silicate of formula δ -$Na_2Si_2O_5$ |
| Carbonate | Anhydrous sodium carbonate with a particle size between 200 μm and 900 μm |
| Bicarbonate | Anhydrous sodium bicarbonate with a particle size distribution between 400 μm and 1200 μm |
| Silicate | Amorphous Sodium Silicate ($SiO_2:Na_2O$; 2.0 ratio) |
| Sulfate | Anhydrous sodium sulfate |
| PAE | ethoxylated (15–18) tetraethylene pentamine |
| PIE | ethoxylated polyethylene imine |
| PAEC | methyl quaternized ethoxylated dihexylene triamine |
| MA/AA | Copolymer of 1:4 maleic/acrylic acid, average molecular weight about 70,000. |
| CMC | Sodium carboxymethyl cellulose |
| Protease | Proteolytic enzyme of activity 4 KNPU/g sold by NOVO Industries A/S under the tradename Savinase |
| Cellulase | Cellulytic enzyme of activity 1000 CEVU/g sold by NOVO Industries A/S under the tradename Carezyme |
| Amylase | Amylolytic enzyme of activity 60 KNU/g sold by NOVO Industries A/S under the tradename Termamyl 60T |
| Lipase | Lipolytic enzyme of activity 100 kLU/g sold by NOVO Industries A/S under the tradename Lipolase |
| PB4 | Sodium perborate tetrahydrate of nominal formula $NaBO_2\ 3H_2O\ H_2O_2$ |
| PB1 | Anhydrous sodium perborate bleach of nominal formula $NaBO_2.H_2O_2$ |
| Percarbonate | Sodium Percarbonate of nominal formula $2Na_2CO_3.3H_2O_2$ |
| NaDCC | Sodium dichloroisocyanurate |
| NOBS | Nonanoyloxybenzene sulfonate, sodium salt |
| EDDS | ethylenediamine disuccinate |
| TAED | Tetraacetylethylenediamine sulfosuccinate disodium lauryl sulfosuccinate |
| DTPMP | Diethylene triamine penta (methylene phosphonate), marketed by Monsanto under Trade name Dequest 2060 |
| Photoactivated bleach | Sulfonated Zinc Phthalocyanine bleach encapsulated in dextrin soluble polymer |
| Brightener 1 | Disodium 4,4'-bis(2-sulphostyryl)biphenyl |
| Brightener 2 | Disodium 4,4'-bis(4-anilino-6-morpholino-1.3.5-triazin-2-yl)amino) stilbene-2:2'-disulfonate. |
| HEDP | 1,1-hydroxyethane diphosphonic acid |
| SRP 1 | Sulfobenzoyl end capped esters with oxyethylene oxy and terephthaloyl backbone |
| SRP 2 | sulfonated ethoxylated terephthalate polymer |
| SRP 3 | methyl capped ethoxylated terephthalate polymer |
| Silicone antifoam | Polydimethylsiloxane foam controller with siloxane-oxyalkylene copolymer as dispersing agent with a ratio of said foam controller to said dispersing agent of 10:1 to 100:1. |
| Isofol 16 | Condea trademark for C16 (average) Guerbet alcohols |
| CaCl2 | Calcium chloride |
| MgCl2 | Magnesium chloride |
| DTPA | Diethylene triamine pentaacetic acid |

In the following Examples all levels are quoted as % by weight of the composition. The following examples are illustrative of the present invention, but are not meant to limit or otherwise define its scope. All parts, percentages and ratios used herein are expressed as percent weight unless otherwise specified.

EXAMPLE 1

The following laundry detergent compositions A to I are prepared in accord with the invention:

|  | A | B | C | D | E | F | G | H | I |
|---|---|---|---|---|---|---|---|---|---|
| LAS | 10 | 10 | 10 | 20 | 20 | 20 | 0 | 0 | 0 |
| C45 AS | 10 | 10 | 10 | 0 | 0 | 0 | 20 | 20 | 20 |
| $MB_{15}AE_7$ | 1 | 2.5 | 5 | 1 | 2.5 | 5 | 1 | 2.5 | 5 |
| Zeolite A | 28 | 28 | 28 | 28 | 28 | 28 | 28 | 28 | 28 |
| PAA | 2 | 2 | 2 | 2 | 2 | 2 | 2 | 2 | 2 |
| Carbonate | 27 | 27 | 27 | 27 | 27 | 27 | 27 | 27 | 27 |
| Silicate | 0.6 | 0.6 | 0.6 | 0.6 | 0.6 | 0.6 | 0.6 | 0.6 | 0.6 |
| Perborate | 1.0 | 1.0 | 1.0 | 1.0 | 1.0 | 1.0 | 1.0 | 1.0 | 1.0 |
| Protease | 0.3 | 0.3 | 0.3 | 0.3 | 0.3 | 0.3 | 0.3 | 0.3 | 0.3 |
| Carezyme | 0.3 | 0.3 | 0.3 | 0.3 | 0.3 | 0.3 | 0.3 | 0.3 | 0.3 |
| SRP1 | 0.4 | 0.4 | 0.4 | 0.4 | 0.4 | 0.4 | 0.4 | 0.4 | 0.4 |
| Brightener | 0.2 | 0.2 | 0.2 | 0.2 | 0.2 | 0.2 | 0.2 | 0.2 | 0.2 |
| PEG | 1.6 | 1.6 | 1.6 | 1.6 | 1.6 | 1.6 | 1.6 | 1.6 | 1.6 |
| Sulfate | 5.5 | 5.5 | 5.5 | 5.5 | 5.5 | 5.5 | 5.5 | 5.5 | 5.5 |
| Silicone Antifoam | 0.42 | 0.42 | 0.42 | 0.42 | 0.42 | 0.42 | 0.42 | 0.42 | 0.42 |
| Moisture & Minors |  |  |  |  | Balance |  |  |  |  |

EXAMPLE 2

The following laundry detergent compositions J to N are prepared in accord with the invention:

|  | J | K | L | M | N |
|---|---|---|---|---|---|
| C45 AS | 8 | 5 | 0 | 8 | 8 |
| LAS | 0 | 12 | 17 | 0 | 8 |
| $MB_{15}AE_7$ | 7 | 6 | 5 | 4 | 8 |
| Soap | 0 | 0.5 | 0 | 0 | 0 |
| C23E6.5 | 0 | 0 | 0 | 0 | 1 |
| C45E5 | 0 | 0 | 0 | 3 | 0 |
| Zeolite A | 15 | 25 | 15 | 15 | 23 |
| Citric | 3 | 0 | 3 | 3 | 0 |
| NaSKS-6 | 11 | 6 | 11 | 11 | 0 |
| Carbonate | 8.5 | 8.5 | 8.5 | 8.5 | 17 |
| Silicate | 0 | 2 | 0 | 0 | 0.7 |
| Sulfate | 2.3 | 3 | 3 | 3 | 16 |
| MA/AA | 4.3 | 4.3 | 4.3 | 4.3 | 0 |
| CMC | 0.4 | 0 | 0 | 0 | 0 |
| PAA | 0 | 0 | 0 | 0 | 2 |
| SRP1 | 0.2 | 0 | 0.2 | 0.2 | 0.3 |
| Protease | 0.9 | 0.5 | 0.5 | 0.5 | 0.1 |
| Lipase | 0.2 | 0 | 0 | 0 | 0 |
| Carezyme | 0.3 | 0.3 | 0.3 | 0.3 | 0.2 |
| Amylase | 0.4 | 0 | 0 | 0 | 0 |
| Percarbonate | 21 | 21 | 21 | 0 | 0 |
| TAED | 5 | 5 | 5 | 0 | 0 |
| Perborate | 0 | 0 | 0 | 0 | 2.7 |
| NOBS | 0 | 0 | 0 | 0 | 4.7 |
| HEDP | 0.5 | 0 | 0 | 0 | 0.5 |
| Brightener | 0.2 | 0.2 | 0.2 | 0.2 | 0.2 |
| Suds Suppressor | 0.4 | 0.4 | 0.4 | 0.4 | 0.4 |
| Moisture & Minors |  |  | Balance |  |  |

EXAMPLE 3

The following laundry detergent compositions O to S are prepared in accord with the invention:

|  | O | P | Q | R | S |
|---|---|---|---|---|---|
| Anionic Surfactant | 0 | 0 | 0 | 1 | 1 |
| $MB_{15}AE_9$ | 20 | 17 | 12 | 20 | 20 |
| Soap | 12 | 0 | 0 | 0 | 0 |
| Zeolite A | 20 | 4 | 0 | 15 | 15 |
| STPP | 0 | 50 | 40 | 0 | 0 |
| PAA | 3.5 | 0 | 2 | 5 | 5 |
| Carbonate | 0 | 10 | 5 | 15 | 15 |
| Silicate | 20 | 5.5 | 24 | 2 | 2 |
| NOBS | 0 | 0 | 0 | 0 | 5 |
| Perborate | 0 | 0 | 0 | 0 | 3 |
| Protease | 0.8 | 0.5 | 0.5 | 0.5 | 0.5 |
| Carezyme | 0 | 0.3 | 0 | 0.3 | 0.3 |
| SRP1 | 0 | 0.2 | 0.3 | 0.3 | 0.3 |
| Brightener | 0.5 | 0.5 | 0.2 | 0.3 | 0.3 |
| PEG | 1 | 0 | 0 | 2.5 | 2.5 |
| Sulfate | 5 | 0 | 0 | 5 | 5 |
| Silicone Antifoam | 0.2 | 0.2 | 0 | 0 | 0.3 |
| Moisture & Minors |  |  | Balance |  |  |

EXAMPLE 4

The following high density detergent formulations T to V, according to the present invention, are prepared:

|  | T | U | V |
|---|---|---|---|
| Nonionic Agglomerate |  |  |  |
| $MB_{16}AE_9$ | 9.0 | 4.5 | 9.0 |
| C45E7 | 0 | 4.5 | 0 |
| C45AS | 2.0 | 2.0 | 2.0 |
| Zeolite A | 1.1 | 1.1 | 1.1 |
| Citrate | 1.8 | 1.8 | 1.8 |
| PEG | 1.4 | 1.4 | 1.4 |
| Carbonate | 3.0 | 3.0 | 3.0 |
| Anionic Agglomerate |  |  |  |
| C45E0.3S | 20.3 | 20.3 | 20.3 |
| Zeolite A | 11.3 | 11.3 | 11.3 |
| Carbonate | 3.9 | 3.9 | 3.9 |
| CMC | 0.7 | 0.7 | 0.7 |

-continued

|  | T | U | V |
|---|---|---|---|
| Dry-Add |  |  |  |
| Zeolite A | 4.5 | 4.5 | 4.5 |
| NaSKS-6 | 10.8 | 10.8 | 10.8 |
| MA/AA | 5.9 | 5.9 | 5.9 |
| Perborate | 5.3 | 5.3 | 10 |
| TAED | 0 | 0 | 5 |
| HEDP | 0.4 | 0.4 | 0.4 |
| Protease | 0.5 | 0.5 | 0 |
| Suds Suppressor | 0.4 | 0.4 | 0 |
| Brighteners | 0.2 | 0.2 | 0 |
| Moisture & Minors |  | Balance |  |

EXAMPLE 5

The following liquid laundry detergent compositions W to Z are prepared in accord with the invention:

|  | W | X | Y | Z |
|---|---|---|---|---|
| $MB_{15}AE_7$ | 0.5–5 | 4–6 | 10–15 | 20–25 |
| Any combination of: | 21.5 | 19 | 5–15 | 1–6 |
| C25 ExS*Na |  |  |  |  |
| (x = 1.8–2.5) |  |  |  |  |
| C25 AS (linear to |  |  |  |  |
| high 2-alkyl) |  |  |  |  |
| C14–17 NaPS |  |  |  |  |
| C12–16 SAS |  |  |  |  |
| C18 1,4 disulfate |  |  |  |  |
| C11.3 LAS |  |  |  |  |
| C12–16 MES |  |  |  |  |
| LMFAA | 2.5–5.5 | 2.5–5.5 | 0–3 | 0–3 |
| Any combination of: | 0–1.5 | 0–1.5 | 0–2 | 0–3 |
| APA |  |  |  |  |
| AQA |  |  |  |  |
| C12–14 trimethyl |  |  |  |  |
| ammonium halide |  |  |  |  |
| Citric Acid | 3 | 1 | 1 | 1 |
| Fatty Acid (TPK, C12/14 | 2 | 10.6 | 0–5 | 0–5 |
| or Rapeseed) |  |  |  |  |
| EtOH | 3.4 | 1.8 | 4 | 5.5 |
| PG | 6.4 | 9.4 | 6 | 4 |
| MEA | 1 | 6.5 | 3 | 1.5 |
| NaOH | 3 | 1.5 | 1.5 | 1 |
| Na toluene sulfonate | 2.3 | 0–2 | 2–4 | 2–4 |
| Borax | 2–2.5 | 2–2.5 | 2–2.5 | 2–2.5 |
| CaCl2 | 0.02 | 0.02 | 0.02 | 0.02 |
| Protease | 0.9 | 0.48–0.6 | 0.6–0.9 | 0.9 |
| Lipase | 0.04–0.08 | 0.06–0.14 | 0.08 | 0.08 |
| Amylase | 0.15 | 0.06–0.14 | 0.1 | 0.1 |
| Cellulase | 0.05 | 0.03 | 0.03 | 0.03 |
| PAE | 1.2 | 0.2–0.7 | 0.7–1.2 | 1.2 |
| SRP 2 or 3 | 0.1–0.2 | 0.1–0.2 | 0.1–0.2 | 0.1–0.2 |
| Brightener 1 or 2 | 0.1–0.2 | 0.15 | 0.15–0.3 | 0.3 |
| Silicone antifoam | 0.12 | 0.2–0.25 | 0–0.12 | 0–0.12 |
| Isofol 16 | 0–2 | 0–2 | 0–2 | — |
| Fumed Silica | 0.0015 | 0.0015 | — | — |
| Perfume | 0.5 | 0.5 | 0.3–0.5 | 0.3–0.5 |
| Dye | 0.0013 | 0.0013 | 0.0013 | 0.0013 |
| Water and Minors |  | Balance |  |  |
| Product pH (10% in DI water) | 7.6 | 7.6 | 6–8 | 6–8 |

EXAMPLE 6

A glass cleaning composition according to the present invention is prepared as follows:

| $MB_{15}AE_7$ | 1% |
|---|---|
| Methanol | 30% |
| Water | Balance |

EXAMPLE 7

Branched ethoxylated surfactants are made by reaction of the appropriate branched alcohols with ethylene oxide. The branched alcohols are made from linear olefins (alpha and/or internal olefins) that have been molecularly re-arranged by exposure to appropriate catalysts. No additional carbons are added in this re-arrangement, but the starting olefin is isomerized so that it now contains one or more alkyl branches along the main alkyl chain. As the olefin moiety stays intact throughout this molecular re-arrangement, a -$CH_2OH$ group is then added via hydrofornylation chemistry. The following Shell Research experimental test alcohol samples are ethoxylated (average ethoxylation of 7).

| $^{13}$C-NMR Results For Branched Alcohols Prepared | | | |
|---|---|---|---|
| Total Number of Carbons | 16 | 17 | 18 |
| Avg. Number of Branches per Molecule | 2.0 | 1.7 | 2.1 |
| Average Branch Position Relative To Hydroxyl Carbon | | | |
| % at C4 and higher | 56% | 55% | 52% |
| % at C3 | 26% | 21% | 25% |
| % at C2 | 18% | 24% | 23% |
| Type of Branching | | | |
| % propyl and higher | 31% | 35% | 30% |
| % ethyl | 12% | 10% | 12% |
| % methyl | 57% | 55% | 58% |

Solutions of laundry prototype formulas are prepared as shown below.

| PPM Ingredients In The Wash Solution | | | | | |
|---|---|---|---|---|---|
|  | A | B | C | D | E |
| C11.9 LAS | 92 | — | — | — | — |
| C45AS | 110 | 212 | 106 | 106 | 106 |
| C45E3S | 10 | — | — | — | — |
| C23E6.5 | 15 | 15 | 15 | 15 | 15 |
| $MB_{16}AE_7$ | 50 | — | 106 | — | — |
| $MB_{17}AE_7$ | 50 | 50 | — | 106 | — |
| $MB_{18}AE_7$ | — | 50 | — | — | 106 |
| Zeolite A | 271 | 271 | 271 | 271 | 271 |
| Carbonate | 50 | 50 | 50 | 50 | 50 |
| Sulfate | 52 | 52 | 52 | 52 | 52 |
| Perborate | 10 | 10 | 10 | 10 | 10 |
| PAA | 22 | 22 | 22 | 22 | 22 |
| PEG | 9 | 9 | 9 | 9 | 9 |
| Silicate | 6 | 6 | 6 | 6 | 6 |

EXAMPLE 8

Solutions of laundry prototype formulas are prepared as shown below.

| PPM Ingredients In The Wash Solution | | | |
|---|---|---|---|
| | F | G | H |
| C11.9 LAS | 144 | 144 | 144 |
| C45AS | 24 | 24 | 24 |
| C45E3S | 9 | 9 | 9 |
| C23E6.5 | 15 | 15 | 15 |
| $MB_{16}AE_7$ | 73 | — | — |
| $MB_{17}AE_7$ | — | 73 | — |
| $MB_{18}AE_7$ | — | — | 73 |
| Zeolite A | 260 | 260 | 260 |
| Carbonate | 193 | 193 | 193 |
| Sulfate | 52 | 52 | 52 |
| Perborate | 10 | 10 | 10 |
| PAA | 22 | 22 | 22 |
| PEG | 9 | 9 | 9 |
| Silicate | 6 | 6 | 6 |

The manufacture of heavy duty liquid detergent compositions, especially those designed for fabric laundering, which comprise a non-aqueous carrier medium can be conducted in the manner disclosed in more detail hereinafter. In an alternate mode, such non-aqueous compositions can be prepared according to the disclosures of U.S. Pat. Nos. 4,753,570; 4,767,558; 4,772,413; 4,889,652; 4,892,673; GB-A-2,158,838; GB-A-2,195,125; GB-A-2,195,649; U.S. Pat. No. 4,988,462; U.S. Pat. No. 5,266,233; EP-A-225,654 (6/16/87); EP-A-510,762 (10/28/92); EP-A-540,089 (5/5/93); EP-A-540,090 (5/5/93); U.S. Pat. No. 4,615,820; EP-A-565,017 (10/13/93); EP-A-030,096 (6/10/81), incorporated herein by reference. Such compositions can contain various particulate detersive ingredients (including the bleaching agents, as disclosed hereinabove) stably suspended therein. Such non-aqueous compositions thus comprise a LIQUID PHASE and, optionally but preferably, a SOLID PHASE, all as described in more detail hereinafter and in the cited references. The mid-chain branched primary alkyl polyoxyalkylene is incorporated in the compositions at the levels and in the manner described hereinabove for the manufacture of other laundry detergent compositions.

Liquid Phase

The liquid phase will generally comprise from about 35% to 99% by weight of the detergent compositions herein. More preferably, the liquid phase will comprise from about 50% to 95% by weight of the compositions. Most preferably, the liquid phase will comprise from about 45% to 75% by weight of the compositions herein. The liquid phase of the detergent compositions herein essentially contains relatively high concentrations of a certain type anionic surfactant combined with a certain type of nonaqueous, liquid diluent.

(A) Essential Anionic Surfactant

The anionic surfactant essentially utilized as an essential component of the nonaqueous liquid phase is one selected from the alkali metal salts of alkylbenzene sulfonic acids in which the alkyl group contains from about 10 to 16 carbon atoms, in straight chain or branched chain configuration. (See U.S. Pat. Nos. 2,220,099 and 2,477,383, incorporated herein by reference.) Especially preferred are the sodium and potassium linear straight chain alkylbenzene sulfonates (LAS) in which the average number of carbon atoms in the alkyl group is from about 11 to 14. Sodum $C_{11}$–$C_{14}$ LAS is especially preferred.

The alkylbenzene sulfonate anionic surfactant will be dissolved in the nonaqueous liquid diluent which makes up the second essential component of the nonaqueous phase. To form the structured liquid phase required for suitable phase stability and acceptable rheology, the alkylbenzene sulfonate anionic surfactant is generally present to the extent of from about 30% to 65% by weight of the liquid phase. More preferably, the alkylbenzene sulfonate anionic surfactant will comprise from about 35% to 50% by weight of the nonaqueous liquid phase of the compositions herein. Utilization of this anionic surfactant in these concentrations corresponds to an anionic surfactant concentration in the total composition of from about 15% to 60% by weight, more preferably from about 20% to 40% by weight, of the composition.

(B) Nonaqueous Liquid Diluent

To form the liquid phase of the detergent compositions, the hereinbefore described alkylbenzene sulfonate anionic surfactant is combined with a nonaqueous liquid diluent which contains two essential components. These two components are a liquid alcohol alkoxylate material and a nonaqueous, low-polarity organic solvent.

i) Alcohol Alkoxylates

One essential component of the liquid diluent used to form the compositions herein comprises an alkoxylated fatty alcohol material. Such materials are themselves also nonionic surfactants. Such materials correspond to the general formula:

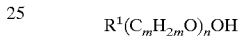

$$R^1(C_mH_{2m}O)_nOH$$

wherein $R^1$ is a $C_8$–$C_{16}$ alkyl group, m is from 2 to 4, and n ranges from about 2 to 12. Preferably $R^1$ is an alkyl group, which may be primary or secondary, that contains from about 9 to 15 carbon atoms, more preferably from about 10 to 14 carbon atoms. Preferably also the alkoxylated fatty alcohols will be ethoxylated materials that contain from about 2 to 12 ethylene oxide moieties per molecule, more preferably from about 3 to 10 ethylene oxide moieties per molecule.

The alkoxylated fatty alcohol component of the liquid diluent will frequently have a hydrophilic-lipophilic balance (HLB) which ranges from about 3 to 17. More preferably, the HLB of this material will range from about 6 to 15, most preferably from about 8 to 15.

Examples of fatty alcohol alkoxylates useful as one of the essential components of the nonaqueous liquid diluent in the compositions herein will include those which are made from alcohols of 12 to 15 carbon atoms and which contain about 7 moles of ethylene oxide. Such materials have been commercially marketed under the trade names Neodol 25-7 and Neodol 23-6.5 by Shell Chemical Company. Other useful Neodols include Neodol 1-5, an ethoxylated fatty alcohol averaging 11 carbon atoms in its alkyl chain with about 5 moles of ethylene oxide; Neodol 23-9, an ethoxylated primary $C_{12}$-$C_{13}$ alcohol having about 9 moles of ethylene oxide and Neodol 91-10, an ethoxylated $C_9$–$C_{11}$ primary alcohol having about 10 moles of ethylene oxide. Alcohol ethoxylates of this type have also been marketed by Shell Chemical Company under the Dobanol tradename. Dobanol 91-5 is an ethoxylated $C_9$–$C_{11}$ fatty alcohol with an average of 5 moles ethylene oxide and Dobanol 25-7 is an ethoxylated $C_{12}$–$C_{15}$ fatty alcohol with an average of 7 moles of ethylene oxide per mole of fatty alcohol.

Other examples of suitable ethoxylated alcohols include Tergitol 15-S-7 and Tergitol 15-S-9 both of which are linear secondary alcohol ethoxylates that have been commercially marketed by Union Carbide Corporation. The former is a mixed ethoxylation product of $C_{11}$ to $C_{15}$ linear secondary alkanol with 7 moles of ethylene oxide and the latter is a similar product but with 9 moles of ethylene oxide being reacted.

Other types of alcohol ethoxylates useful in the present compositions are higher molecular weight nonionics, such as Neodol 45-11, which are similar ethylene oxide condensation products of higher fatty alcohols, with the higher fatty alcohol being of 14–15 carbon atoms and the number of ethylene oxide groups per mole being about 11. Such products have also been commercially marketed by Shell Chemical Company.

The alcohol alkoxylate component which is essentially utilized as part of the liquid diluent in the nonaqueous compositions herein will generally be present to the extent of from about 1% to 60% of the liquid phase composition. More preferably, the alcohol alkoxylate component will comprise about 5% to 40% of the liquid phase. Most preferably, the essentially utilized alcohol alkoxylate component will comprise from about 5% to 30% of the detergent composition liquid phase. Utilization of alcohol alkoxylate in these concentrations in the liquid phase corresponds to an alcohol alkoxylate concentration in the total composition of from about 1% to 60% by weight, more preferably from about 2% to 40% by weight, and most preferably from about 5% to 25% by weight, of the composition.

ii) Nonaqueous Low-Polarity Organic Solvent

A second essential component of the liquid diluent which forms part of the liquid phase of the detergent compositions herein comprises nonaqueous, low-polarity organic solvent (s). The term "solvent" is used herein to connote the non-surface active carrier or diluent portion of the liquid phase of the composition.

While some of the essential and/or optional components of the compositions herein may actually dissolve in the "solvent"-containing liquid phase, other components will be present as particulate material dispersed within the "solvent"-containing liquid phase. Thus the term "solvent" is not meant to require that the solvent material be capable of actually dissolving all of the detergent composition components added thereto.

The nonaqueous organic materials which are employed as solvents herein are those which are liquids of low polarity. For purposes of this invention, "low-polarity" liquids are those which have little, if any, tendency to dissolve one of the preferred types of particulate material used in the compositions herein, i.e., the peroxygen bleaching agents, sodium perborate or sodium percarbonate. Thus relatively polar solvents such as ethanol should not be utilized. Suitable types of low-polarity solvents useful in the nonaqueous liquid detergent compositions herein do include non-vicinal $C_4$–$C_8$ alkylene glycols, alkylene glycol mono lower alkyl ethers, lower molecular weight polyethylene glycols, lower molecular weight methyl esters and amides, and the like.

A preferred type of nonaqueous, low-polarity solvent for use in the compositions herein comprises the non-vicinal $C_4$–$C_8$ branched or straight chain alkylene glycols. Materials of this type include hexylene glycol (4-methyl-2,4-pentanediol), 1,6-hexanediol, 1,3-butylene glycol and 1,4-butylene glycol. Hexylene glycol is the most preferred.

Another preferred type of nonaqueous, low-polarity solvent for use herein comprises the mono-, di-, tri-, or tetra-$C_2$–$C_3$ alkylene glycol mono $C_2$–$C_6$ alkyl ethers. The specific examples of such compounds include diethylene glycol monobutyl ether, tetraethylene glycol monobutyl ether, dipropylene glycol monoethyl ether, and dipropylene glycol monobutyl ether. Diethylene glycol monobutyl ether and dipropylene glycol monobutyl ether are especially preferred. Compounds of the type have been commercially marketed under the tradenames Dowanol, Carbitol, and Cellosolve.

Another preferred type of nonaqueous, low-polarity organic solvent useful herein comprises the lower molecular weight polyethylene glycols (PEGs). Such materials are those having molecular weights of at least about 150. PEGs of molecular weight ranging from about 200 to 600 are most preferred.

Yet another preferred type of non-polar, nonaqueous solvent comprises lower molecular weight methyl esters. Such materials are those of the general formula: $R^1$—C(O)—OCH$_3$ wherein $R^1$ ranges from 1 to about 18. Examples of suitable lower molecular weight methyl esters include methyl acetate, methyl propionate, methyl octanoate, and methyl dodecanoate.

The nonaqueous, low-polarity organic solvent(s) employed should, of course, be compatible and non-reactive with other composition components, e.g., bleach and/or activators, used in the liquid detergent compositions herein. Such a solvent component will generally be utilized in an amount of from about 1% to 70% by weight of the liquid phase. More preferably, the nonaqueous, low-polarity organic solvent will comprise from about 10% to 60% by weight of the liquid phase, most preferably from about 20% to 50% by weight, of the liquid phase of the composition. Utilization of this organic solvent in these concentrations in the liquid phase corresponds to a solvent concentration in the total composition of from about 1% to 50% by weight, more preferably from about 5% to 40% by weight, and most preferably from about 10% to 30% by weight, of the composition.

iii) Alcohol Alkoxylate To Solvent Ratio

The ratio of alcohol alkoxylate to organic solvent within the liquid diluent can be used to vary the rheological properties of the detergent compositions eventually formed. Generally, the weight ratio of alcohol alkoxylate to organic solvent will range from about 50:1 to 1:50. More preferably, this ratio will range from about 3:1 to 1:3.

iv) Liquid Diluent Concentration

As with the concentration of the alkylbenzene sulfonate anionic surfactant mixture, the amount of total liquid diluent in the nonaqueous liquid phase herein will be determined by the type and amounts of other composition components and by the desired composition properties. Generally, the liquid diluent will comprise from about 35% to 70% of the nonaqueous liquid phase of the compositions herein. More preferably, the liquid diluent will comprise from about 50% to 65% of the nonaqueous liquid phase. This corresponds to a nonaqueous liquid diluent concentration in the total composition of from about 15% to 70% by weight, more preferably from about 20% to 50% by weight, of the composition.

Solid Phase

The nonaqueous detergent compositions herein also essentially comprise from about 1% to 65% by weight, more preferably from about 5% to 50% by weight, of a solid phase of particulate material which is dispersed and suspended within the liquid phase. Generally such particulate material will range in size from about 0.1 to 1500 microns. More preferably such material will range in size from about 5 to 200 microns.

The particulate material utilized herein can comprise one or more types of detergent composition components which in particulate form are substantially insoluble in the nonaqueous liquid phase of the composition. The types of particulate materials which can be utilized are described in detail as follows:

Composition Preparation and Use

The nonaqueous liquid detergent compositions herein can be prepared by combining the essential and optional components thereof in any convenient order and by mixing, e.g., agitating, the resulting component combination to form the phase stable compositions herein. In a typical process for preparing such compositions, essential and certain preferred optional components will be combined in a particular order and under certain conditions.

In the first step of such a typical preparation process, an admixture of the alkylbenzene sulfonate anionic surfactant and the two essential components of the nonaqueous diluent is formed by heating a combination of these materials to a temperature from about 30° C. to 100° C.

In a second process step, the heated admixture formed as hereinbefore described is maintained under shear agitation at a temperature from about 40° C. to 100C for a period of from about 2 minutes to 20 hours. Optionally, a vacuum can be applied to the admixture at this point. This second process step serves to completely dissolve the anionic surfactant in the nonaqueous liquid phase.

In a third process step, this liquid phase combination of materials is cooled to a temperature of from about 0° C. to 35° C. This cooling step serves to form a structured, surfactant-containing liquid base into which the particulate material of the detergent compositions herein can be added and dispersed.

Particulate material is added in a fourth process step by combining the particulate material with the liquid base which is maintained under conditions of shear agitation. When more than one type of particulate material is to be added, it is preferred that a certain order of addition be observed. For example, while shear agitation is maintained, essentially all of any optional surfactants in solid particulate form can be added in the form of particles ranging in size from about 0.2 to 1,000 microns. After addition of any optional surfactant particles, particles of substantially all of an organic builder, e.g., citrate and/or fatty acid, and/or an alkalinity source, e.g., sodium carbonate, can be added while continuing to maintain this admixture of composition components under shear agitation. Other solid form optional ingredients can then be added to the composition at this point. Agitation of the mixture is continued, and if necessary, can be increased at this point to form a uniform dispersion of insoluble solid phase particulates within the liquid phase.

After some or all of the foregoing solid materials have been added to this agitated mixture, the particles of the bleaching agent can be added to the composition, again while the mixture is maintained under shear agitation. By adding the bleaching agent material last, or after all or most of the other components, and especially after alkalinity source particles, have been added, desirable stability benefits for the bleach can be realized. If enzyme prills are incorporated, they are preferably added to the nonaqueous liquid matrix last.

As a final process step, after addition of all of the particulate material, agitation of the mixture is continued for a period of time sufficient to form compositions having the requisite viscosity and phase stability characteristics. Frequently this will involve agitation for a period of from about 1 to 30 minutes.

As a variation of the composition preparation procedure hereinbefore described, one or more of the solid components may be added to the agitated mixture as a slurry of particles premixed with a minor portion of one or more of the liquid components. Thus a premix of a small fraction of the alcohol alkoxylate and/or nonaqueous, low-polarity solvent with particles of the organic builder material and/or the particles of the inorganic alkalinity source and/or particles of a bleach activator may be separately formed and added as a slurry to the agitated mixture of composition components. Addition of such slurry premixes should precede addition of bleaching agent and/or enzyme particles which may themselves be part of a premix slurry formed in analogous fashion.

The compositions of this invention, prepared as hereinbefore described, can be used to form aqueous washing solutions for use in the laundering and bleaching of fabrics. Generally, an effective amount of such compositions is added to water, preferably in a conventional fabric laundering automatic washing machine, to form such aqueous laundering/bleaching solutions. The aqueous washing/bleaching solution so formed is then contacted, preferably under agitation, with the fabrics to be laundered and bleached therewith.

An effective amount of the liquid detergent compositions herein added to water to form aqueous laundering/bleaching solutions can comprise amounts sufficient to form from about 500 to 7,000 ppm of composition in aqueous solution. More preferably, from about 800 to 3,000 ppm of the detergent compositions herein will be provided in aqueous washing/bleaching solution.

EXAMPLE 9

Preparation of LAS Powder for Use as a Structurant

Sodium $C_{12}$ linear alkyl benzene sulfonate (NaLAS) is processed into a powder containing two phases. One of these phases is soluble in the non-aqueous liquid detergent compositions herein and the other phase is insoluble. It is the insoluble fraction which serves to add structure and particle suspending capability to the non-aqueous phase of the compositions herein.

NaLAS powder is produced by taking a slurry of NaLAS in water (approximately 40–50% active) combined with dissolved sodium sulfate (3–15%) and hydrotrope, sodium sulfosuccinate (1–3%). The hydrotrope and sulfate are used to improve the characteristics of the dry powder. A drum dryer is used to dry the slurry into a flake. When the NaLAS is dried with the sodium sulfate, two distinct phases are created within the flake. The insoluble phase creates a network structure of aggregate small particles (0.4–2 um) which allows the finished non-aqueous detergent product to stably suspend solids.

The NaLAS powder prepared according to this example has the following makeup shown in Table I.

TABLE I

| Component | Wt. % |
|---|---|
| LAS Powder | |
| NaLAS | 85% |
| Sulfate | 11% |
| Sulfosuccinate | 2% |
| Water | 2.5% |
| Unreacted, etc. | balance to 100% |
| % insoluble LAS | 17% |
| # of phase (via X-ray diffraction) | 2 |

TABLE II

Non-aqueous based heavy duty liquid laundry detergent compositions (A to E) which comprise the mid-chain branched surfactants of the present invention are presented below.

Non-Aqueous Liquid Detergent Composition with Bleach

| Component | Wt % A | Wt % B | Wt % C | Wt % D | Wt % E |
|---|---|---|---|---|---|
| LAS, From Above | 16 | 13 | 8 | 8 | 2 |
| MB16AE7 | 22 | 25 | 28 | 30 | 34 |
| BPP | 19 | 19 | 19 | 19 | 19 |
| Citrate | 3 | 3 | 3 | 3 | 3 |
| Bleach activator | 5.9 | 5.9 | 5.9 | 5.9 | 5.9 |
| Carbonate | 9 | 9 | 9 | 9 | 9 |
| MA/AA | 3 | 3 | 3 | 3 | 3 |
| Colored speckles | 0.4 | 0.4 | 0.4 | 0.4 | 0.4 |
| EDDS | 1 | 1 | 1 | 1 | 1 |
| Cellulase Prills | 0.1 | 0.1 | 0.1 | 0.1 | 0.1 |
| Amylase Prills | 0.4 | 0.4 | 0.4 | 0.4 | 0.4 |
| Ethoxylated diamine quat | 1.3 | 1.3 | 1.3 | 1.3 | 1.3 |
| Perborate | 15 | 15 | 15 | 15 | 15 |
| Optionals including: brightener, colorant, perfume, thickener, suds suppressor, colored speckles etc. | balance | balance | balance | balance | balance |
| | 100% | 100% | 100% | 100% | 100% |

The resulting Table II composition is a stable, anhydrous heavy-duty liquid laundry detergent which provides excellent stain and soil removal performance when used in normal fabric laundering operations.

The following Example further illustrates the invention herein with respect to a hand dishwashing liquid.

Example 10

| Ingredient | % (wt.) | Range (% wt.) |
|---|---|---|
| $MB_{16.5}AE_{10}$ | 2.0 | 0.15–15 |
| C23AS | 7.0 | 2–35 |
| C23E1S | 20.5 | 5–35 |
| Coconut amine oxide | 2.6 | 2–5 |
| Betaine/Tetronic 704 ®** | 0.87–0.10 | 0–2 (mix) |
| $C_8E_{11}$ | 5.0 | 2–10 |
| Sodium xylene sulfonate | 4.0 | 1–6 |
| EtOH | 4.0 | 0–7 |
| Ciitrate | 0.06 | 0–1.0 |
| MgCl2 | 3.3 | 0–4.0 |
| $CaCl_2$ | 2.5 | 0–4.0 |
| Ammonium sulfate | 0.08 | 0–4.0 |
| Hydrogen peroxide | 200 ppm | 10–300 ppm |
| Perfume | 0.18 | 0–0.5 |
| Maxatase ® protease | 0.50 | 0–1.0 |
| Water and minors | Balance | |

**Cocoalkyl betaine.

The following Examples further illustrate the invention herein with respect to a granular phosphate-containing automatic dishwashing detergent.

Example 11

| INGREDIENTS | % by weight of active material | |
|---|---|---|
| | A | B |
| STPP | 31 | 26 |
| $MB_{16.5}AE_7$ | 1 | 1 |
| Carbonate | 22 | 32 |
| Silicate | 9 | 7 |
| Surfactant (nonionic) | 3 | 1.5 |
| NaDCC | 2 | — |
| Perborate | — | 5 |
| TAED | — | 1.5 |
| Savinase (Au/g) | — | 0.04 |
| Termamyl (Amu/g) | | 425 |
| Sulfate | 25 | 25 |
| Perfume/Minors | to 100% | to 100% |

The hard surface cleaning compositions of the present invention may further comprise one or more optional components known for use in hard surface cleaning compositions provided that the optional components are physically and chemically compatible with the essential component described herein, or do not otherwise unduly impair product stability, aesthetics or performance. Concentrations of such optional components typically range from about 0.001% to about 30% by weight of the hard surface cleaning compositions, when present.

Optional components include dyes, diluents, antimicrobial agents, antifungal agents, anti mould agents, antimildue agents, insect repellant, suds suppressors, enzymes, thickeners, thinners, reheology agents (i.e. agents which change or stabilize the rehology of a composition), thixotropic agents, foam boosters, perfumes, preservatives, antioxidants; and aesthetic components such as fragrances, colorings, and the like. This list of optional components is not meant to be exclusive, and other optional components can be used.

Packaging form of the hard surface cleaner compositions

The compositions herein may be packaged in a variety of suitable detergent packaging known to those skilled in the art. The liquid compositions are preferably packaged in conventional detergent plastic bottles.

In one embodiment the compositions herein may be packaged in manually operated spray dispensing containers, which are usually made of synthetic organic polymeric plastic materials. Accordingly, the present invention also encompasses liquid cleaning compositions of the invention packaged in a spray dispenser, preferably in a trigger spray dispenser or pump spray dispenser.

Indeed, said spray-type dispensers allow to uniformly apply to a relatively large area of a surface to be cleaned the liquid cleaning compositions suitable for use according to the present invention. Such spray-type dispensers are particularly suitable to clean vertical surfaces.

Suitable spray-type dispensers to be used according to the present invention include manually operated foam trigger-type dispensers sold for example by Specialty Packaging Products, Inc. or Continental Sprayers, Inc. These types of dispensers are disclosed, for instance, in U.S. Pat. No. 4,701,311 to Dunning et al. and U.S. Pat. No. 4,646,973 and U.S. Pat. No. 4,538,745 both to Focarracci. Particularly preferred to be used herein are spray-type dispensers such as T 8500® commercially available from Continental Spray International or T 8100® commercially available from Canyon, Northern Ireland. In such a dispenser the liquid composition is divided in fine liquid droplets resulting in a spray that is directed onto the surface to be treated. Indeed, in such a spray-type dispenser the composition contained in the body of said dispenser is directed through the spray-type dispenser head via energy communicated to a pumping mechanism by the user as said user activates said pumping mechanism. More particularly, in said spray-type dispenser head the composition is forced against an obstacle, e.g. a grid or a cone or the like, thereby providing shocks to help atomize the liquid composition, i.e. to help the formation of liquid droplets.

EXAMPLE 12

The following compositions are made by mixing the listed ingredients in the listed proportions. These compositions are used neat to clean marble and dilute to clean lacquered wooden floors. Excellent cleaning and surface safety performance are observed.

|  | A | B | C | D | E | F | G | H |
|---|---|---|---|---|---|---|---|---|
| MB15AE7 | 3.0 | 3.0 | 5.0 | 3.2 | 3.2 | 3.2 | 8.0 | 8.0 |
| C23E3 | 1.0 | 1.0 | 1.5 | 1.3 | 1.3 | 1.5 | 3.0 | 3.5 |
| C24E21 | 2.0 | 2.0 | 2.5 | 1.9 | 1.9 | 2.0 | 5.0 | 6.0 |
| NaPS | 2.0 | 1.5 | 1.2 | 1.2 | 1.0 | 1.7 | 3.0 | 2.5 |
| SCS | 1.2 | 3.0 | 2.2 | 2.0 | 2.0 | 1.5 | 4.0 | 5.0 |
| MgSO4 | 0.20 | 0.9 | 0.30 | 0.50 | 1.3 | 2.0 | 1.0 | 3.0 |
| Citrate | 0.3 | 1.0 | 0.5 | 0.75 | 1.8 | 3.0 | 1.5 | 6.0 |
| Bicarbonate | 0.06 | 0.1 | — | 0.1 | — | 0.2 | — | — |
| Na2HPO4 | — | — | 0.1 | — | 0.3 | — | — | — |
| Na2H2P2O7 | — | — | — | — | — | — | 0.2 | 0.5 |
| pH | 8.0 | 7.5 | 7.0 | 7.25 | 8.0 | 7.4 | 7.5 | 7.2 |
| Water and Minors | q.s. to 100% | | | | | | | |

EXAMPLE 13

The following compositions are made by mixing the listed ingredients in the listed proportions. All proportions are % by weight of the total composition.

Excellent first and next-time cleaning performance and good gloss are delivered to the hard-surfaces cleaned with these compositions both under neat and diluted conditions, e.g. at a dilution level of 50:1 to 200:1 (water:composition).

|  | T | U | V | W | X | Y |
|---|---|---|---|---|---|---|
| Nonionic surfactants | | | | | | |
| MB15AE7 | 2.4 | 1.9 | 2.5 | 2 | 2 | 2.5 |
| C24 E5 | 3.6 | 2.9 | 2.5 | 2.5 | 3.2 | 2.5 |
| C23E3 | — | — | — | — | 1.3 | — |
| C24E21 | 1.0 | 0.8 | 4.0 | — | 1.9 | 2.0 |
| Anionic surfactants | | | | | | |
| NaPS | — | — | — | — | — | — |
| LAS | — | — | — | — | 0.9 | 0.8 |
| SCS | 1.5 | 2.6 | — | 2.3 | 1.2 | 1.5 |
| Isalchem ® AS | 0.6 | 0.6 | — | 2 | 2 | — |
| Buffer | | | | | | |
| Carbonate | 0.6 | 0.13 | 0.6 | 1.0 | 1.0 | 0.1 |
| Citrate | 0.5 | 0.56 | 0.5 | — | — | 0.6 |
| Caustic | 0.3 | 0.33 | 0.3 | — | — | 0.3 |
| Suds control | | | | | | |
| Fatty Acid | 0.6 | 0.3 | 0.5 | 0.4 | 0.4 | 0.5 |
| Isofol 12 ® | 0.3 | 0.3 | — | 0.3 | 0.3 | 0.3 |

-continued

|  | T | U | V | W | X | Y |
|---|---|---|---|---|---|---|
| Polymers | | | | | | |
| PEG DME-2000 ® | 0.4 | — | 0.3 | — | — | 0.35 |
| Jeffamine ® ED-2001 | — | 0.4 | — | — | — | — |
| Polyglycol AM ® 1100 | — | — | — | 0.5 | — | — |
| PVP K60 ® | — | 0.4 | 0.6 | 0.3 | — | 0.3 |
| PEG (2000) | — | — | — | — | 0.5 | — |
| Minors and water | up to 100% | | | | | |
| pH | 9.5 | 7.4 | 9.5 | 10.5 | 10.75 | 7.5 |

PVP K60® is a vinylpyrrolidone homopolymer (average molecular weight of 160,000), commercially available from ISP Corporation, New York, N.Y. and Montreal, Canada.

PEG DME-2000® is dimethyl polyethylene glycol (MW 2000) commercially available from Hoescht. Jeffamine® ED-2001 is a capped polyethylene glycol commercially available from Huntsman.

PEG (2000) is polyethylene glycol (MW 2000).

Isofol 12(® is 2-butyl octanol

Isalchem® AS is a branched alcohol alkyl sulphate commercially available from Enichem.

EXAMPLE 14

The following compositions are tested for their cleaning performance when used diluted on greasy soil.

The following compositions are made by mixing the listed ingredients in the listed proportions:

| | Weight % | | |
|---|---|---|---|
| Ingredients | NN | OO | PP |
| NaPS | 1.0 | 3 | 3 |
| C23E7 | 4 | — | — |
| C24 E21 | 1 | 3 | 2 |
| MB15AE7 | 5 | 1 | 2 |
| Citrate | 3 | 3 | 3 |
| Butylcarbitol R | 4 | 4 | 4 |
| Triethanolamine | 1 | 1 | 1 |
| water & minors | up to 100% | | |

EXAMPLE 15

|  | QQ | RR | SS | TT | UU |
|---|---|---|---|---|---|
| N-2-ethylhexyl sulfosuccinamate | 3.0 | — | 3.0 | — | 3.0 |
| N-2-propylheptyl sulfosuccinamate | — | 3.0 | — | 3.0 | — |
| *C$_{11}$E$_5$ | 7.0 | 14.0 | 14.0 | — | — |
| *C$_{11}$E$_7$ | — | — | — | 7.0 | 7.0 |
| *C$_{10}$E$_7$ | 7.0 | — | — | 7.0 | 7.0 |
| MB15AE7 | 3.0 | 3.0 | 3.0 | 3.0 | 3.0 |
| Citrate | 1.0 | 1.0 | — | 1.0 | 1.0 |
| Potassium carbonate | 0.2 | 0.2 | 0.2 | 0.2 | 0.2 |
| Triethanol amine | — | — | 1.0 | — | — |
| MA/AA | — | — | 0.25 | — | — |
| Perfume | 1.0 | 1.0 | 1.0 | 1.0 | 1.0 |
| Alkalinity adjusted to pH | 10.5 | 10.5 | 7.4 | 10.5 | 10.5 |
| Water, salts, fillers | balance | balance | balance | balance | balance |

EXAMPLE 16

| Ingredient | JJJ | KKK | LLL |
|---|---|---|---|
| 3-(N-dodecyl-N,N-dimethyl)-2-hydroxy-propane-1-sulfonate | 2.0 | — | — |
| MB16AE7 | 2.0 | 2.0 | 2.0 |
| *$C_{9-11}E6$ | 2.0 | — | — |
| *$C_{8-10}E6$ | — | 2.0 | 2.0 |
| Cocoamido propyl betaine | — | 2.0 | — |
| N-(Coconutamidoethylene)-N-(hydroxyethyl)-glycine[4] | — | — | 2.0 |
| BPP | 8.0 | 8.0 | 8.0 |
| Citric Acid | 6.0 | 6.0 | 6.0 |
| SCS | 1.6 | 1.6 | 1.6 |
| Water, Buffering Agents, and Minors | q.s. to 100 | | |
| pH | 2.97 | 2.97 | 2.97 |

What is claimed is:

1. A bleaching detergent composition comprising from about 0.001% to about 99%, by weight, of one or more mid-chain branched primary alkyl polyoxyalkylenes having the formula:

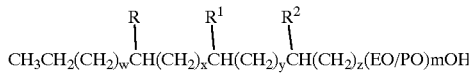

wherein the total number of carbon atoms in the branched primary alkyl moiety of this formula, including the R, $R^1$, and $R^2$ branching, but not including the carbon atoms in the EO/PO alkoxy moiety, is from 14 to 20, and wherein further the average total number of carbon atoms in the branched primary alkyl moieties having the above formula is within the range of greater than 14.5 to about 17.5; R, $R^1$, and $R^2$ are each independently selected from the group consisting of hydrogen and $C_1$–$C_3$ alkyl, provided R, $R^1$, and $R^2$ are not all hydrogen and, when z is 1, at least R or $R^1$ is not hydrogen; w is an integer from 0 to 13; x is an integer from 0 to 13; y is an integer from 0 to 13; z is an integer of at least 1; w+x+y+z is from 8 to 14; and EO/PO are alkoxy moieties selected from the group consisting of ethoxy, propoxy, and mixed ethoxy/propoxy groups, wherein m is at least about 1; and from about 1% to about 99.999%, by weight, of one or more detergent adjunct ingredients, said composition having a pH of 9 to 11 in use in an aqueous cleaning operation.

2. A composition according to either of claim 1 wherein R, $R^1$, and $R^2$ are each independently selected from the group consisting of hydrogen and methyl.

3. A composition according to claim 1 comprising at least 2% of one or more mid-chain branched primary alkyl polyoxyalkylenes wherein z is at least 2.

4. A composition according to claim 1 comprising at least 20% of one or more mid-chain branched primary alkyl polyoxyalkylenes wherein z is at least 2.

5. A composition according to claim 1 comprising at least 5% of mid-chain branched primary alkyl polyoxyalkylenes wherein m is within the range of from about 3 to about 30.

6. A composition according to claim 1 comprising at least 20% of mid-chain branched primary alkyl polyoxyalkylenes wherein m is within the range of from about 5 to about 20.

7. A composition according to claim 1 comprising at least about 5% one or more mid-chain branched primary alkyl polyoxyalkylenes having the formula

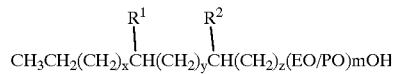

wherein $R^1$ and $R^2$ are each independently hydrogen or $C_1$–$C_3$ alkyl; x is from 0 to 12; y is from 0 to 12; z is at least 2; x+y+z is from 11 to 14; and EO/PO are alkoxy moieties selected from the group consisting of ethoxy, propoxy, and mixed ethoxy/propoxy groups, wherein m is within the range of from about 3 to about 30; provided $R^1$ and $R^2$ are not both hydrogen.

8. A composition according to claim 1 comprising a mixture of branched primary alkyl polyoxyalkylenes having the formula

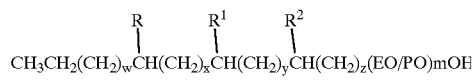

wherein the total number of carbon atoms per molecule, including branching, is from 14 to 20, and wherein further for this surfactant mixture the average total number of carbon atoms in the branched primary alkyl moieties having the above formula is within the range of greater than 14.5 to about 17.5; R, $R^1$, and $R^2$ are each independently selected from the group consisting of hydrogen and $C_1$–$C_3$ alkyl, provided R, $R^1$, and $R^2$ are not all hydrogen; w is an integer from 0 to 13; x is an integer from 0 to 13; y is an integer from 0 to 13; z is an integer of at least 1; w+x+y+z is from 8 to 14; EO/PO are alkoxy moieties selected from the group consisting of ethoxy, propoxy, and mixed ethoxy/propoxy groups, wherein m is within the range of from about 3 to about 30; provided that when $R^2$ is $C_1$–$C_3$ alkyl the weight ratio of surfactants having z equal to 2 or greater to surfactants having z of 1 is at least about 1:1.

9. A detergent composition according to claim 1 comprising
(a) from about 0.001% to about 99% of one or more mid-chain branched primary alkyl polyoxyalkylene surfactants having the formula:

(I)
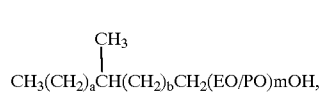

(II)
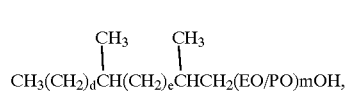

and mixtures thereof; wherein a, b, d, and e are integers, a+b is from 10 to 16, d+e is from 8 to 14 and wherein further when a+b=10, a is an integer from 2 to 9 and b is an integer from 1 to 8;
when a+b=11, a is an integer from 2 to 10 and b is an integer from 1 to 9;
when a+b=12, a is an integer from 2 to 11 and b is an integer from 1 to 10;
when a+b=13, a is an integer from 2 to 12 and b is an integer from 1 to 11;
when a+b=14, a is an integer from 2 to 13 and b is an integer from 1 to 12;
when a+b=15, a is an integer from 2 to 14 and b is an integer from 1 to 13;
when a+b=16, a is an integer from 2 to 15 and b is an integer from 1 to 14;

when d+e=8, d is an integer from 2 to 7 and e is an integer from 1 to 6;
when d+e=9, d is an integer from 2 to 8 and e is an integer from 1 to 7;
when d+e=10, d is an integer from 2 to 9 and e is an integer from 1 to 8;
when d+e=11, d is an integer from 2 to 10 and e is an integer from 1 to 9;
when d+e=12, d is an integer from 2 to 11 and e is an integer from 1 to 10;
when d+e=13, d is an integer from 2 to 12 and e is an integer from 1 to 11;
when d+e=14, d is an integer from 2 to 13 and e is an integer from 1 to 12;
wherein for this surfactant mixture the average total number of carbon atoms in the branched primary alkyl moieties having the above formulas is within the range of greater than 14.5 to about 17.5; and
wherein EO/PO are alkoxy moieties selected from the group consisting of ethoxy, propoxy, and mixed ethoxy/propoxy groups, wherein m is from about 5 to about 20.

10. A composition according to claim 1, comprising mid-chain branched primary alkyl polyoxyalkylene surfactants having the formula

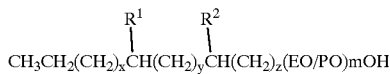

wherein $R^1$ and $R^2$ are each independently hydrogen or methyl; x is from 0 to 12; y is from 0 to 12; z is at least 2; x+y+z is from 11 to 14; and EO/PO are alkoxy moieties selected from the group consisting of ethoxy, propoxy, and mixed ethoxy/propoxy groups, wherein m is from about 5 to about 15; provided $R^1$ and $R^2$ are not both hydrogen.

11. A composition according to claim 1, comprising a mid-chain branched alkyl polyoxyalkylene compound of formula:

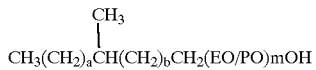

wherein: a is an integer from 2 to 11, b is an integer from 1 to 10, and a+b is 12 or 13; and EO/PO are alkoxy moieties selected from the group consisting of ethoxy, propoxy, and mixed ethoxy/propoxy groups, wherein m is within the range of from about 3 to about 30.

12. A composition according to claim 1 comprising: mono-methyl branched primary alkyl ethoxylates selected from the group consisting of: 3-methyl pentadecanol ethoxylate, 4-methyl pentadecanol ethoxylate, 5-methyl pentadecanol ethoxylate, 6-methyl pentadecanol ethoxylate, 7-methyl pentadecanol ethoxylate, 8-methyl pentadecanol ethoxylate, 9-methyl pentadecanol ethoxylate, 10-methyl pentadecanol ethoxylate, 11-methyl pentadecanol ethoxylate, 12-methyl pentadecanol ethoxylate, 13-methyl pentadecanol ethoxylate, 3-methyl hexadecanol ethoxylate, 4-methyl hexadecanol ethoxylate, 5-methyl hexadecanol ethoxylate, 6-methyl hexadecanol ethoxylate, 7-methyl hexadecanol ethoxylate, 8-methyl hexadecanol ethoxylate, 9-methyl hexadecanol ethoxylate, 10-methyl hexadecanol ethoxylate, 11-methyl hexadecanol ethoxylate, 12-methyl hexadecanol ethoxylate, 13-methyl hexadecanol ethoxylate, 14-methyl hexadecanol ethoxylate, and mixtures thereof, wherein the mono-methyl branched primary ethoxylates have an average degree of ethoxylation of from about 5 to about 15.

13. A detergent composition according to claim 1 comprising a member selected from the group consisting of builders, alkalinity systems, organic polymeric compounds, suds suppressors, soil suspension and anti-redeposition agents, corrosion inhibitors, bleaches, bleach activators, enzymes, anionic surfactants, and mixtures thereof, and a nonionic surfactant which is a member selected from the group consisting of: 3-methyl pentadecanol ethoxylate, 4-methyl pentadecanol ethoxylate, 5-methyl pentadecanol ethoxylate, 6-methyl pentadecanol ethoxylate, 7-methyl pentadecanol ethoxylate, 8-methyl pentadecanol ethoxylate, 9-methyl pentadecanol ethoxylate, 10-methyl pentadecanol ethoxylate, 11-methyl pentadecanol ethoxylate, 12-methyl pentadecanol ethoxylate, 13-methyl pentadecanol ethoxylate, 3-methyl hexadecanol ethoxylate, 4-methyl hexadecanol ethoxylate, 5-methyl hexadecanol ethoxylate, 6-methyl hexadecanol ethoxylate, 7-methyl hexadecanol ethoxylate, 8-methyl hexadecanol ethoxylate, 9-methyl hexadecanol ethoxylate, 10-methyl hexadecanol ethoxylate, 11-methyl hexadecanol ethoxylate, 12-methyl hexadecanol ethoxylate, 13-methyl hexadecanol ethoxylate, 14-methyl hexadecanol ethoxylate, and mixtures thereof, ethoxylated with an average degree of ethoxylation of from about 5 to about 15.

14. A detergent composition comprising a member selected from the group consisting of builders, alkalinity systems, organic polymeric compounds, suds suppressors, soil suspension and anti-redeposition agents, corrosion inhibitors, bleaches, bleach activators, enzymes, anionic surfactants, and mixtures thereof, and a nonionic surfactant which is a member selected from the group consisting of : 2,3-dimethyl tetradecanol ethoxylate, 2,4-dimethyl tetradecanol ethoxylate, 2,5-dimethyl tetradecanol ethoxylate, 2,6-dimethyl tetradecanol ethoxylate, 2,7-dimethyl tetradecanol ethoxylate, 2,8-dimethyl tetradecanol ethoxylate, 2,9-dimethyl tetradecanol ethoxylate, 2,10-dimethyl tetradecanol ethoxylate, 2,11-dimethyl tetradecanol ethoxylate, 2,12-dimethyl tetradecanol ethoxylate, 2,3-dimethyl pentadecanol ethoxylate, 2,4-dimethyl pentadecanol ethoxylate, 2,5-dimethyl pentadecanol ethoxylate, 2,6-dimethyl pentadecanol ethoxylate, 2,7-dimethyl pentadecanol ethoxylate, 2,8-dimethyl pentadecanol ethoxylate, 2,9-dimethyl pentadecanol ethoxylate, 2,10-dimethyl pentadecanol ethoxylate, 2,11-dimethyl pentadecanol ethoxylate, 2,12-dimethyl pentadecanol ethoxylate, and 2,13-dimethyl pentadecanol ethoxylate, and mixtures thereof, ethoxylated with an average degree of ethoxylation of from about 5 to about 15.

* * * * *